(12) United States Patent
Antonacci et al.

(10) Patent No.: US 12,193,711 B2
(45) Date of Patent: Jan. 14, 2025

(54) METHOD FOR IMPROVED SPINAL CORRECTION SURGERY IMPLEMENTING NON-FUSION ANTERIOR SCOLIOSIS CORRECTION TECHNIQUES

(71) Applicant: Institute for Spine & Scoliosis, P.A., Lawrenceville, NJ (US)

(72) Inventors: M Darryl Antonacci, Skillman, NJ (US); Randal R Betz, Bradenton, FL (US); Laury Cuddihy, New York, NY (US)

(73) Assignee: MD ANTONACCI FAMILY TRUST, Sheridan, WY (US)

( * ) Notice: Subject to any disclaimer, the term of this patent is extended or adjusted under 35 U.S.C. 154(b) by 6 days.

(21) Appl. No.: 18/213,745

(22) Filed: Jun. 23, 2023

(65) Prior Publication Data
US 2023/0329757 A1 Oct. 19, 2023

Related U.S. Application Data

(63) Continuation-in-part of application No. 18/103,732, filed on Jan. 31, 2023, now Pat. No. 11,737,788, which is a continuation of application No. 17/124,840, filed on Dec. 17, 2020, now Pat. No. 11,602,376.

(51) Int. Cl.
| | | |
|---|---|---|
| *A61B 17/70* | (2006.01) | |
| *A61B 6/50* | (2024.01) | |
| *A61B 17/02* | (2006.01) | |
| *A61B 34/20* | (2016.01) | |
| *A61B 90/00* | (2016.01) | |
| *A61B 17/3211* | (2006.01) | |
| *A61B 17/56* | (2006.01) | |
| *A61B 17/68* | (2006.01) | |

(52) U.S. Cl.
CPC .......... *A61B 17/7032* (2013.01); *A61B 6/505* (2013.01); *A61B 17/0218* (2013.01); *A61B 17/025* (2013.01); *A61B 17/7001* (2013.01); *A61B 17/7014* (2013.01); *A61B 17/7022* (2013.01); *A61B 34/20* (2016.02); *A61B 90/37* (2016.02); *A61B 2017/0256* (2013.01); *A61B 17/3211* (2013.01); *A61B 2017/565* (2013.01); *A61B 2017/681* (2013.01); *A61B 17/7044* (2013.01); *A61B 2034/2068* (2016.02); *A61B 2090/376* (2016.02)

(58) Field of Classification Search
CPC ............ A61B 17/7022; A61B 17/7014; A61B 17/7029; A61B 17/7031
See application file for complete search history.

(56) References Cited

U.S. PATENT DOCUMENTS

| | | | | |
|---|---|---|---|---|
| 4,041,939 A | * | 8/1977 | Hall ................... | A61B 17/7022 411/378 |
| 4,047,524 A | * | 9/1977 | Hall ................... | A61B 17/7044 411/920 |

(Continued)

*Primary Examiner* — Lynnsy M Summitt
(74) *Attorney, Agent, or Firm* — Sutton Magidoff Barkume LLP

(57) ABSTRACT

Spinal correction surgical techniques and methodologies for correction of scoliosis using non fusion anterior scoliosis correction, including soft tissue releases, unique correction techniques such as de-rotation, and unique single and dual anchor screw/cord applications.

6 Claims, 36 Drawing Sheets

(56) References Cited

U.S. PATENT DOCUMENTS

| | | | | |
|---|---|---|---|---|
| 4,078,559 | A * | 3/1978 | Nissinen | A61B 17/7053 606/263 |
| 4,697,582 | A * | 10/1987 | William | A61B 17/7044 606/254 |
| 5,030,220 | A * | 7/1991 | Howland | A61B 17/705 606/264 |
| 5,199,146 | A * | 4/1993 | Grover | B25B 23/0092 29/280 |
| 5,282,863 | A * | 2/1994 | Burton | A61B 17/7007 623/17.11 |
| 5,387,213 | A * | 2/1995 | Breard | A61F 2/0811 606/256 |
| 5,478,340 | A * | 12/1995 | Kluger | A61B 17/7038 606/259 |
| 5,672,175 | A * | 9/1997 | Martin | A61B 17/7044 606/279 |
| 5,702,395 | A * | 12/1997 | Hopf | A61B 17/7044 606/265 |
| 5,725,582 | A * | 3/1998 | Bevan | A61B 17/842 623/13.12 |
| 6,015,409 | A * | 1/2000 | Jackson | A61B 17/7041 606/278 |
| 6,096,026 | A * | 8/2000 | Schultz | A61B 17/68 606/1 |
| 6,248,106 | B1 * | 6/2001 | Ferree | A61B 17/7022 606/328 |
| 6,296,643 | B1 * | 10/2001 | Hopf | A61B 17/0642 606/308 |
| 6,299,613 | B1 * | 10/2001 | Ogilvie | A61B 17/0642 606/279 |
| 6,325,805 | B1 * | 12/2001 | Ogilvie | A61B 17/0642 606/911 |
| 6,423,065 | B2 * | 7/2002 | Ferree | A61B 17/7058 606/308 |
| 6,551,320 | B2 * | 4/2003 | Lieberman | A61B 17/701 606/86 R |
| 6,626,909 | B2 * | 9/2003 | Chin | A61B 17/7059 606/279 |
| 7,008,431 | B2 * | 3/2006 | Simonson | A61B 17/3421 606/86 R |
| 7,166,073 | B2 * | 1/2007 | Ritland | A61B 17/02 600/210 |
| 7,285,121 | B2 * | 10/2007 | Braun | A61B 17/864 606/279 |
| 7,670,358 | B2 * | 3/2010 | Barry | A61B 17/7077 606/279 |
| 7,909,826 | B2 * | 3/2011 | Serhan | A61B 17/8877 606/75 |
| 7,909,857 | B2 * | 3/2011 | Ogilvie | A61B 17/7005 606/279 |
| 7,976,568 | B2 * | 7/2011 | Cheung | A61B 17/7031 606/279 |
| 8,034,085 | B2 * | 10/2011 | Slivka | A61B 17/7044 606/270 |
| 8,057,472 | B2 * | 11/2011 | Walker | A61B 17/7216 600/12 |
| 8,118,841 | B2 * | 2/2012 | Schwab | A61B 17/7044 606/257 |
| 8,147,524 | B2 * | 4/2012 | Piza Vallespir | A61B 17/7085 606/279 |
| 8,177,810 | B2 * | 5/2012 | Ferree | A61B 17/8861 606/264 |
| 8,182,513 | B2 * | 5/2012 | Calvosa | A61B 17/7031 606/301 |
| 8,202,216 | B2 * | 6/2012 | Melkent | A61B 17/025 600/215 |
| 8,206,421 | B2 * | 6/2012 | Erickson | A61B 17/7083 606/279 |
| 8,211,151 | B2 * | 7/2012 | Schwab | A61B 17/7022 606/264 |
| 8,216,274 | B2 * | 7/2012 | Matthis | A61B 17/701 606/264 |
| 8,262,571 | B2 * | 9/2012 | Ritland | A61B 17/2812 600/220 |
| 8,292,930 | B2 * | 10/2012 | Allard | A61B 17/7031 606/246 |
| 8,328,849 | B2 * | 12/2012 | Nydegger | A61B 17/7022 606/255 |
| 8,337,528 | B2 * | 12/2012 | Ferree | A61B 17/7053 606/279 |
| 8,394,124 | B2 * | 3/2013 | Biyani | A61B 17/7022 606/300 |
| 8,442,621 | B2 * | 5/2013 | Gorek | A61B 90/39 606/97 |
| 8,454,662 | B2 * | 6/2013 | Bethell | A61B 17/7022 606/263 |
| 8,470,002 | B2 * | 6/2013 | Allard | A61B 17/7022 606/279 |
| 8,475,467 | B2 * | 7/2013 | Manninen | A61B 17/7037 104/246 |
| 8,535,318 | B2 * | 9/2013 | Peterson | A61B 17/025 606/104 |
| 8,551,141 | B2 * | 10/2013 | Gephart | A61B 17/7091 606/279 |
| 8,617,220 | B2 * | 12/2013 | Skaggs | A61B 17/70 606/279 |
| 8,641,736 | B2 * | 2/2014 | Marik | A61B 17/7022 606/254 |
| 8,764,806 | B2 * | 7/2014 | Abdou | A61B 17/1611 606/279 |
| 8,870,929 | B2 * | 10/2014 | Parent | A61B 17/70 606/279 |
| 8,876,867 | B2 * | 11/2014 | Hestad | A61B 17/702 606/265 |
| 8,992,536 | B2 * | 3/2015 | Piza Vallespir | A61B 17/7085 606/279 |
| 8,998,988 | B2 * | 4/2015 | Phillips | A61B 17/7059 623/17.11 |
| 9,017,388 | B2 * | 4/2015 | Molz, IV | A61B 17/8866 606/264 |
| 9,028,532 | B2 * | 5/2015 | Cavali | A61B 17/7026 606/257 |
| 9,101,412 | B2 * | 8/2015 | Bootwala | A61B 17/7077 |
| 9,131,937 | B2 * | 9/2015 | Chan | A61B 17/0401 |
| 9,168,071 | B2 * | 10/2015 | Seme | A61B 17/7014 |
| 9,211,145 | B2 * | 12/2015 | Pereiro De Lamo | A61B 50/15 |
| 9,237,907 | B2 * | 1/2016 | Powers | A61B 17/7022 |
| 9,247,964 | B1 * | 2/2016 | Shoshtaev | A61B 17/7083 |
| 9,289,243 | B2 * | 3/2016 | Dekutoski | A61B 17/7089 |
| 9,289,251 | B2 * | 3/2016 | Leroux | A61B 17/708 |
| 9,339,301 | B2 * | 5/2016 | Barry | A61B 17/7079 |
| 9,345,517 | B2 * | 5/2016 | Zhang | A61B 17/7052 |
| 9,433,442 | B2 * | 9/2016 | Lindemann | A61B 17/7053 |
| 9,439,691 | B2 * | 9/2016 | Tribus | A61B 17/7077 |
| 9,730,684 | B2 * | 8/2017 | Beale | A61B 17/3468 |
| 9,743,921 | B2 * | 8/2017 | Hennard | A61B 17/02 |
| 9,788,867 | B2 * | 10/2017 | Dvorak | A61B 17/7038 |
| 9,907,583 | B2 * | 3/2018 | Hayes | A61B 17/708 |
| 10,064,656 | B2 * | 9/2018 | Mundis, Jr | A61B 17/7022 |
| 10,278,736 | B2 * | 5/2019 | Samdani | A61B 17/7077 |
| 10,390,862 | B2 * | 8/2019 | Bobbitt | A61B 17/7037 |
| 10,420,588 | B2 * | 9/2019 | Murray | A61B 17/842 |
| 10,420,593 | B2 * | 9/2019 | Wall | A61B 17/7091 |
| 10,441,320 | B2 * | 10/2019 | Lai | A61B 17/701 |
| 10,449,006 | B2 * | 10/2019 | Dace | A61B 17/7076 |
| 10,456,211 | B2 * | 10/2019 | McAfee | A61B 17/025 |
| 10,492,837 | B2 * | 12/2019 | Farmer | A61B 17/708 |
| 10,624,683 | B2 * | 4/2020 | Suddaby | A61B 17/7067 |
| 10,660,673 | B2 * | 5/2020 | Maly | A61B 17/7053 |
| 10,667,845 | B2 * | 6/2020 | Milbrandt | A61B 17/7032 |
| 10,682,130 | B2 * | 6/2020 | White | A61B 1/055 |
| 10,695,099 | B2 * | 6/2020 | Scholl | A61B 17/001 |
| 10,702,311 | B2 * | 7/2020 | Seme | A61B 17/707 |
| 10,751,127 | B2 * | 8/2020 | Dace | A61B 34/10 |
| 10,758,274 | B1 * | 9/2020 | Bess | A61B 17/7053 |
| 10,849,691 | B2 * | 12/2020 | Zucker | A61B 17/7083 |
| 10,857,003 | B1 * | 12/2020 | Abdou | A61B 17/8695 |
| 10,869,693 | B2 * | 12/2020 | Mcclintock | A61B 17/7022 |
| 10,893,888 | B2 * | 1/2021 | Rawlinson | A61B 17/7032 |

(56) References Cited

U.S. PATENT DOCUMENTS

| | | | | |
|---|---|---|---|---|
| 10,898,239 B2* | 1/2021 | Olea | A61B 17/7079 |
| 10,918,422 B2* | 2/2021 | Mosnier | A61B 17/1606 |
| 11,020,149 B2* | 6/2021 | Gordon | A61B 17/7049 |
| 11,051,854 B2* | 7/2021 | Mire | A61B 17/7014 |
| 11,065,037 B2* | 7/2021 | Barrett | A61B 17/8869 |
| 11,185,353 B2* | 11/2021 | Prygoski | A61B 17/7053 |
| 11,246,636 B2* | 2/2022 | Braun | A61B 17/8605 |
| 11,317,949 B2* | 5/2022 | Suddaby | A61B 17/7011 |
| 11,344,337 B2* | 5/2022 | Gandhi | A61B 17/7043 |
| 11,389,204 B2* | 7/2022 | Antonacci | A61B 17/7001 |
| 11,406,425 B2* | 8/2022 | Simpson | A61B 17/7053 |
| 2002/0133155 A1* | 9/2002 | Ferree | A61B 17/7031 606/264 |
| 2005/0010220 A1* | 1/2005 | Casutt | A61B 17/7082 606/86 A |
| 2005/0033291 A1* | 2/2005 | Ebara | A61B 17/7034 606/53 |
| 2005/0075644 A1* | 4/2005 | DiPoto | A61F 2/4455 606/90 |
| 2005/0090899 A1* | 4/2005 | DiPoto | A61B 17/7037 623/17.11 |
| 2005/0119593 A1* | 6/2005 | Gallard | A61B 17/7074 600/594 |
| 2005/0267470 A1* | 12/2005 | McBride | A61B 17/7022 606/279 |
| 2006/0282073 A1* | 12/2006 | Simanovsky | A61B 17/707 606/329 |
| 2007/0073293 A1* | 3/2007 | Martz | A61L 27/365 606/86 A |
| 2007/0078460 A1* | 4/2007 | Frigg | A61B 17/7083 606/86 A |
| 2008/0009863 A1* | 1/2008 | Bond | A61B 17/8869 606/86 A |
| 2008/0077138 A1* | 3/2008 | Cohen | A61B 17/708 606/86 A |
| 2008/0140133 A1* | 6/2008 | Allard | A61B 17/7022 606/257 |
| 2008/0255615 A1* | 10/2008 | Vittur | A61B 17/56 600/300 |
| 2009/0088803 A1* | 4/2009 | Justis | A61B 17/7083 606/103 |
| 2009/0234392 A1* | 9/2009 | Dziedzic | A61B 17/7085 606/301 |
| 2010/0318129 A1* | 12/2010 | Seme | A61B 17/7001 606/279 |
| 2014/0107707 A1* | 4/2014 | Rovner | A61B 17/7002 606/279 |
| 2016/0324547 A1* | 11/2016 | Miller | A61B 17/7032 |
| 2018/0049754 A1* | 2/2018 | Tarricone | A61B 90/50 |
| 2018/0098799 A1* | 4/2018 | Songer | A61B 17/7083 |
| 2019/0274728 A1* | 9/2019 | LaPierre | A61F 2/446 |
| 2020/0022731 A1* | 1/2020 | Cook | A61B 17/7035 |
| 2020/0170696 A1* | 6/2020 | Haber | A61B 17/7044 |
| 2020/0187993 A1* | 6/2020 | Schwab | A61B 17/7031 |
| 2020/0237408 A1* | 7/2020 | Ziemek | A61B 17/7083 |
| 2020/0237410 A1* | 7/2020 | Gabos | A61B 17/7079 |
| 2020/0315708 A1* | 10/2020 | Mosnier | G16H 50/20 |
| 2020/0323559 A1* | 10/2020 | Skinner | A61B 17/3417 |
| 2020/0323562 A1* | 10/2020 | Hoernschemeyer | A61B 17/7032 |
| 2020/0360059 A1* | 11/2020 | Hoernschemeyer | A61B 17/7053 |
| 2021/0052298 A1* | 2/2021 | Thommen | A61B 1/00128 |
| 2021/0128264 A1* | 5/2021 | Prygoski | A61B 17/7044 |
| 2021/0145518 A1* | 5/2021 | Mosnier | G06N 3/047 |
| 2021/0145519 A1* | 5/2021 | Mosnier | G06N 3/04 |
| 2021/0186575 A1* | 6/2021 | Biedermann | A61B 17/7032 |
| 2021/0322060 A1* | 10/2021 | Barrett | A61B 17/701 |
| 2022/0110662 A1* | 4/2022 | LaColla | A61B 17/7044 |
| 2022/0160411 A1* | 5/2022 | Braun | A61B 17/0401 |
| 2022/0218417 A1* | 7/2022 | Josse | A61B 17/8811 |
| 2022/0395302 A1* | 12/2022 | Groenewold | A61B 17/7077 |
| 2022/0409246 A1* | 12/2022 | Hua | A61B 17/7076 |

* cited by examiner

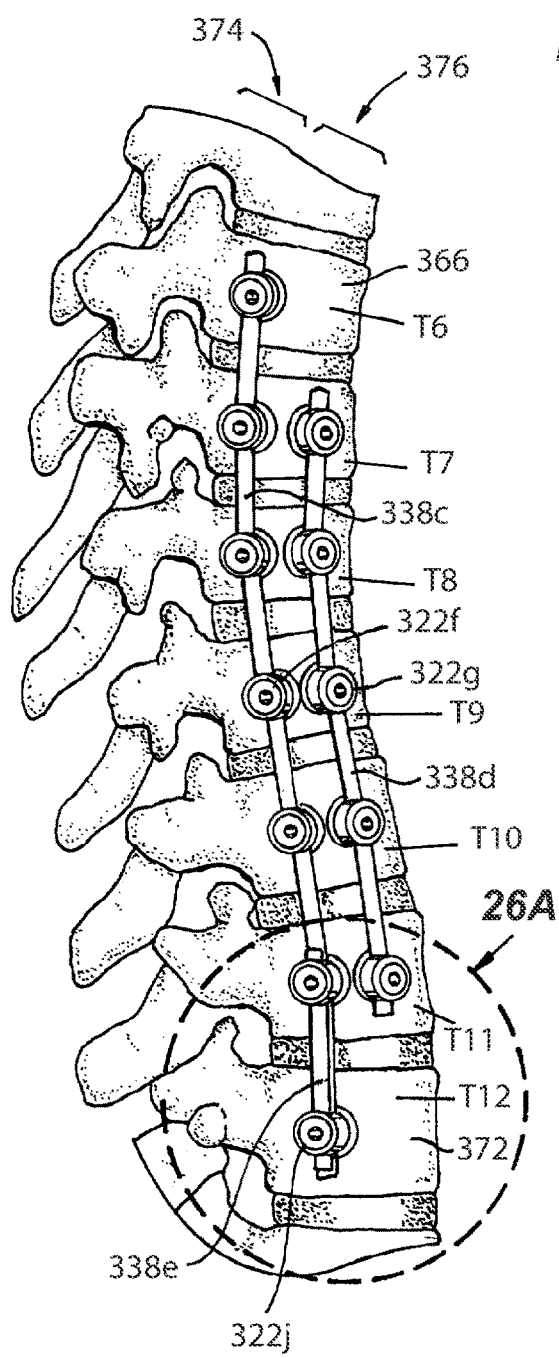
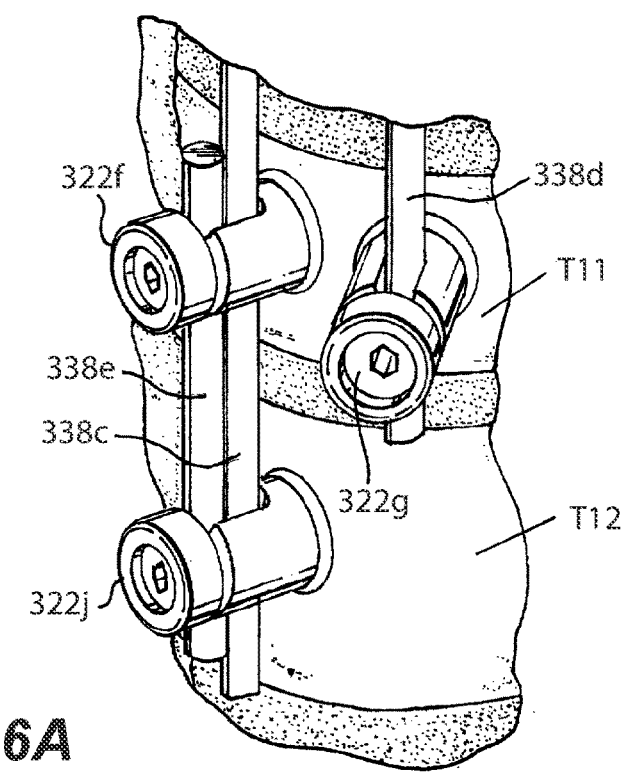
Fig. 26
Fig. 26A

*Fig. 27*
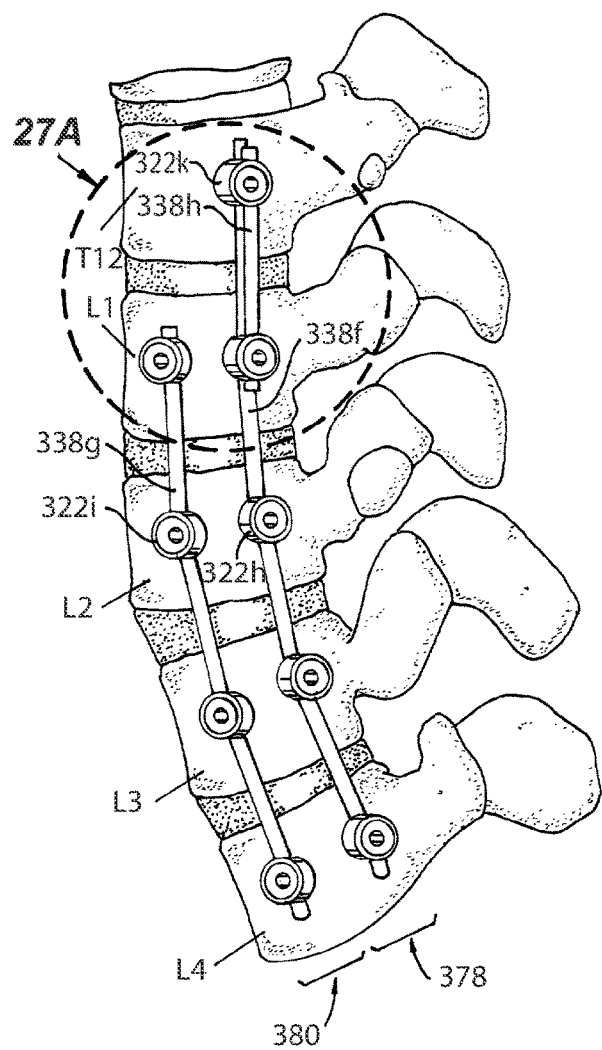
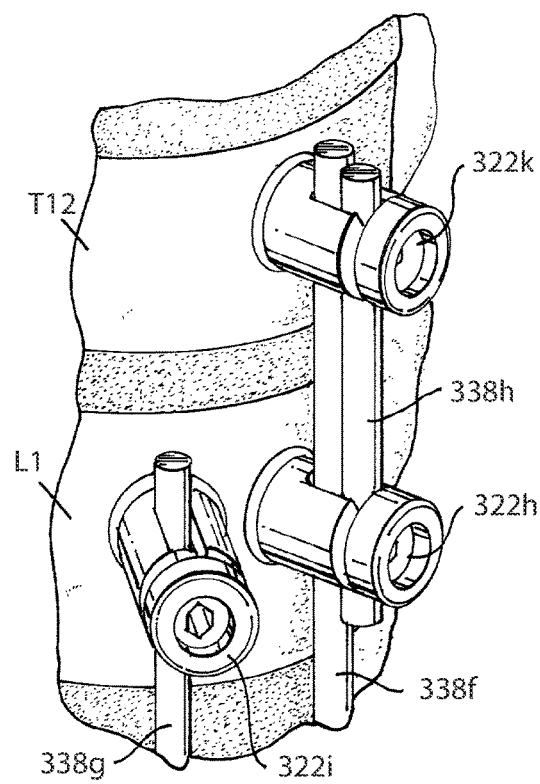
*Fig. 27A*

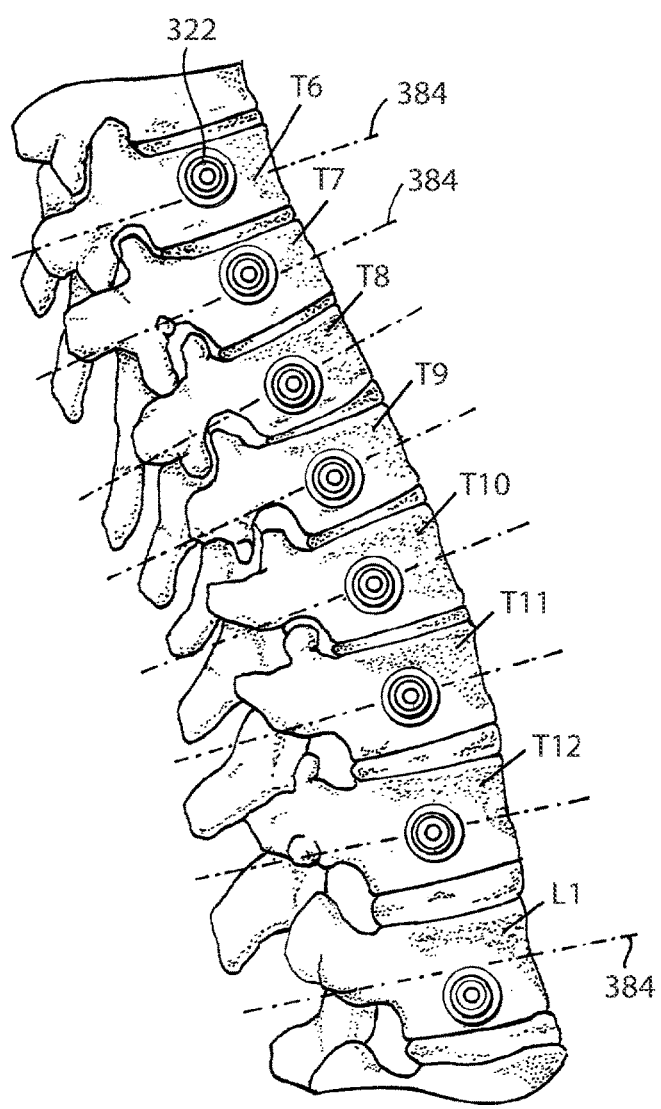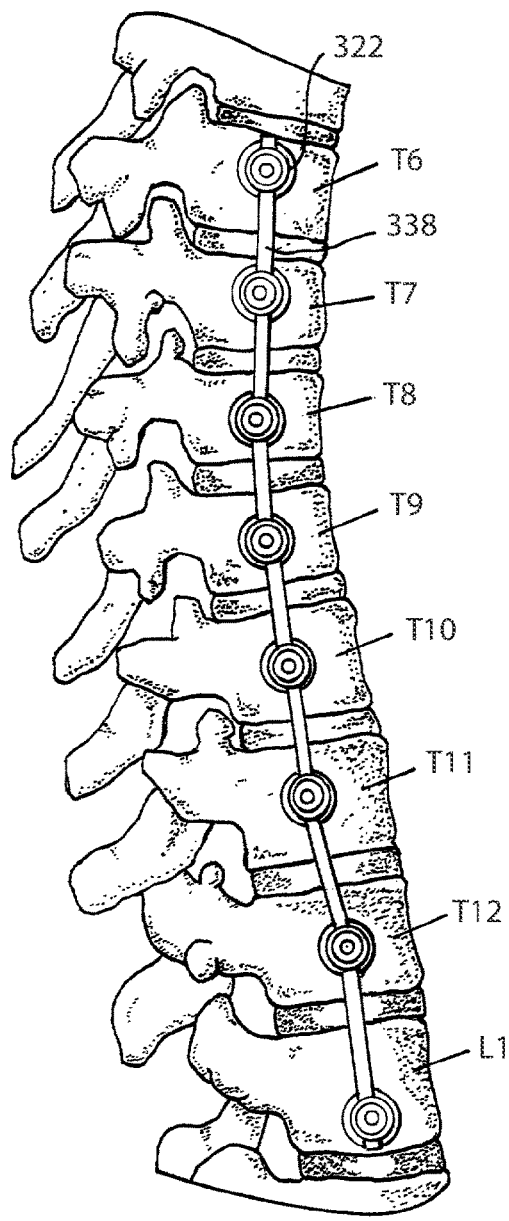
*Fig. 30*       *Fig. 31*

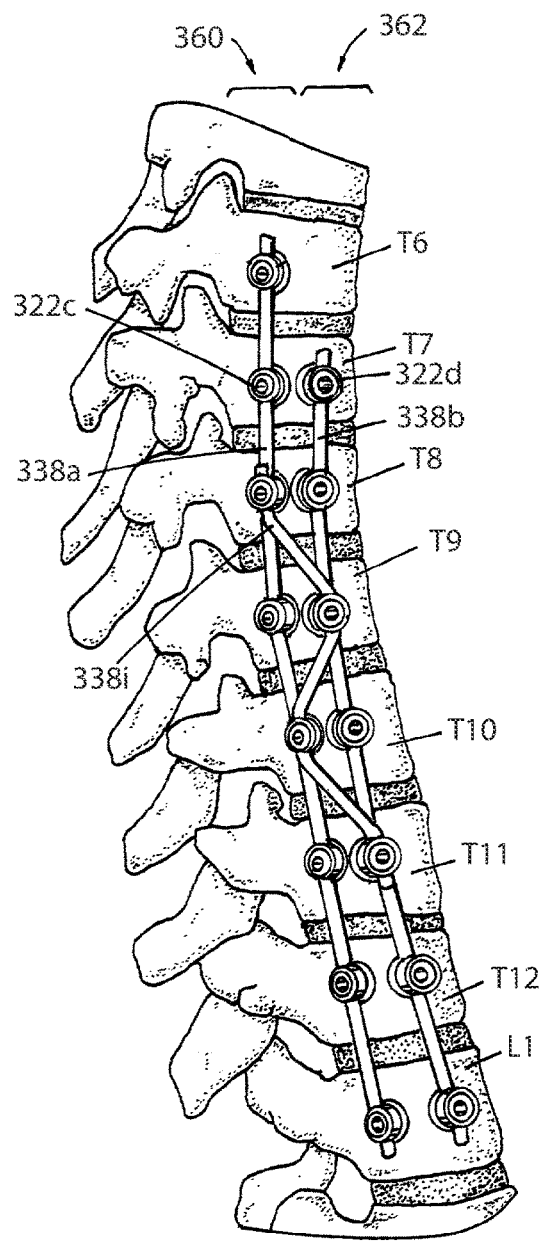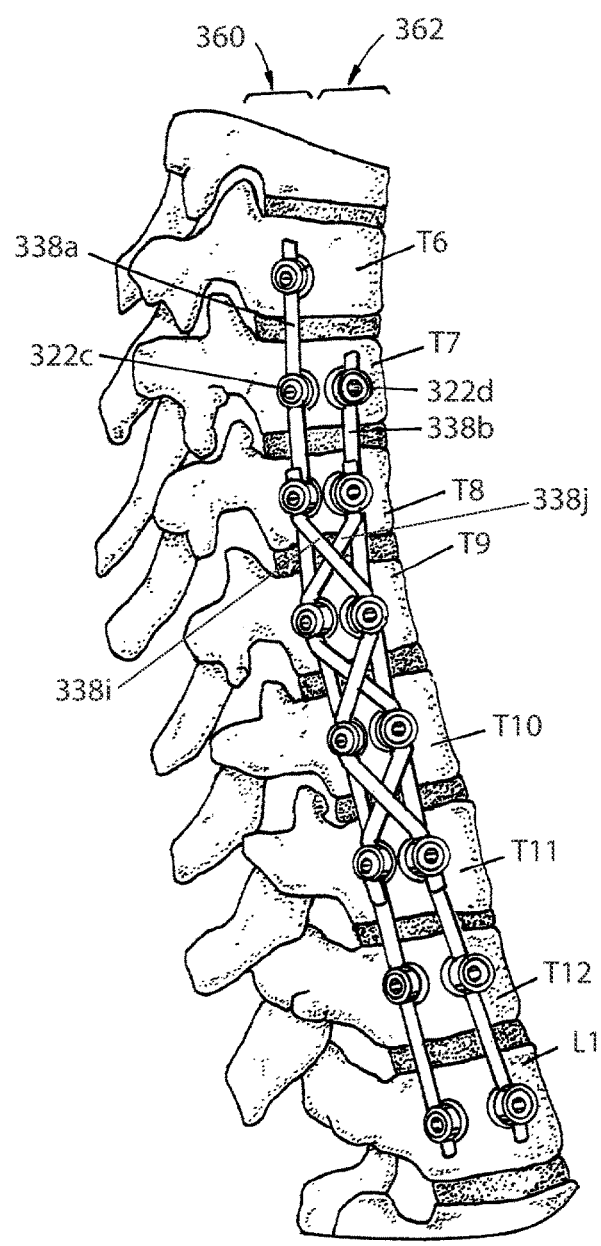
Fig. 34A
Fig. 34B

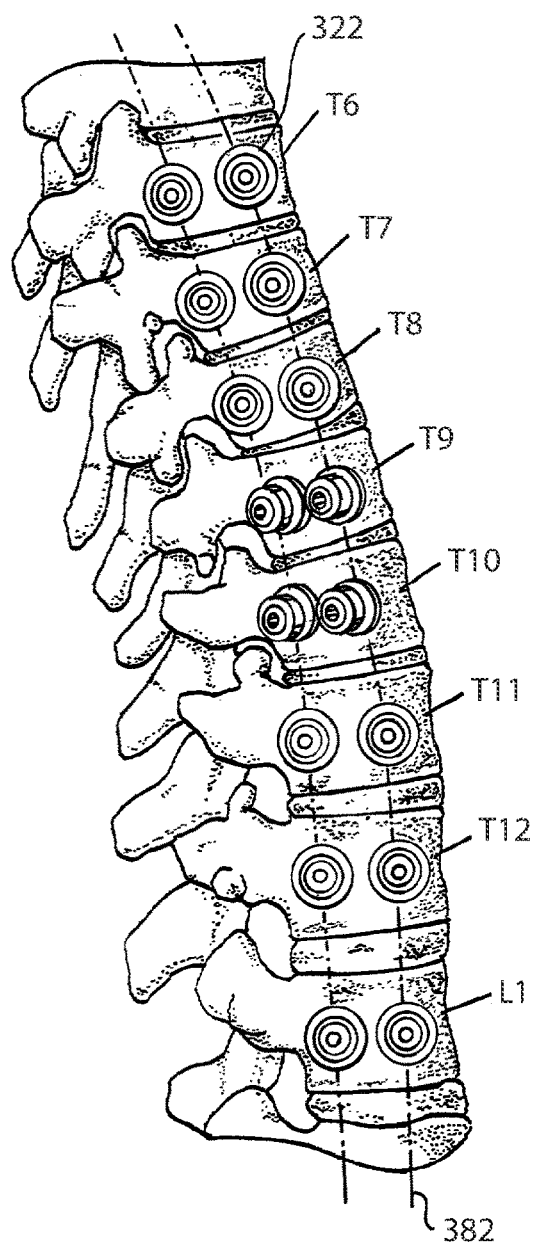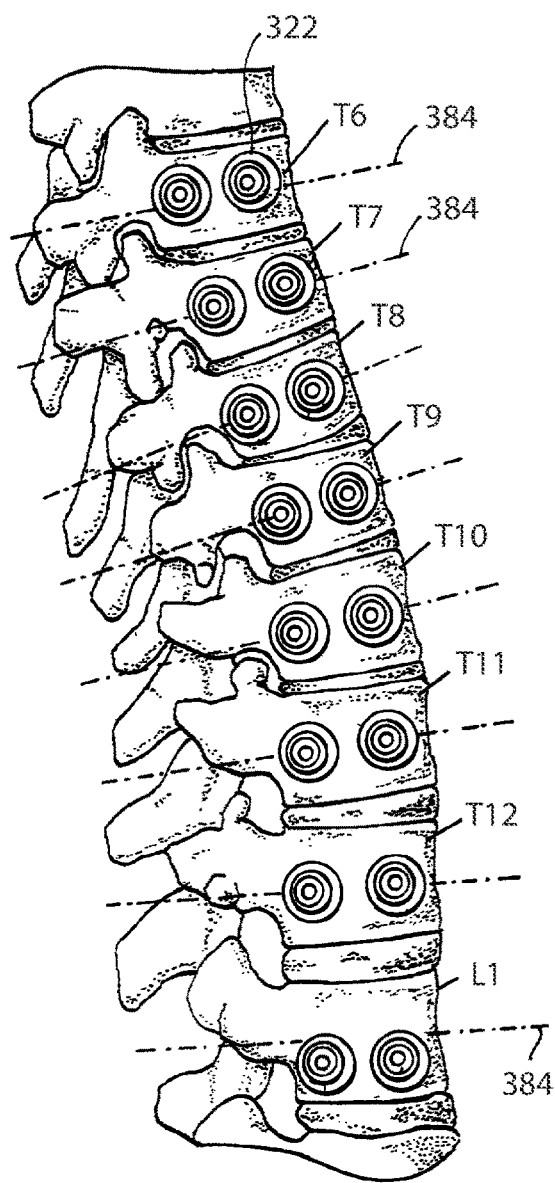
*Fig. 43*      *Fig. 44*

METHOD FOR IMPROVED SPINAL CORRECTION SURGERY IMPLEMENTING NON-FUSION ANTERIOR SCOLIOSIS CORRECTION TECHNIQUES

TECHNICAL FIELD

This application relates to spinal correction surgical techniques and methodologies, and in particular to improved methodologies for correction of scoliosis using non fusion anterior scoliosis correction, including soft tissue releases, unique correction techniques such as de-rotation, and unique single and dual anchor screw/cord applications.

BACKGROUND OF THE INVENTION

Spinal correction surgical techniques, in particular those used in practice for correction of scoliosis, have included bracing, fusion, and more recently, a methodology referred to as vertebral body tethering (VBT). The practice of bracing has been the mainstay of non-operative treatment, but it may only be effective on relatively younger patients having a comparatively mild case of scoliosis (e.g. a Cobb angle of 45° or less). Bracing requires the patient to be fitted for an externally worn brace, and then the patient must wear the brace continuously in order to be effective. The technique of fusion with metal rods, which is still prevalent, has been the mainstay of surgical treatment for patients with Cobb angles less than 45°. Traditional spinal fusion for scoliosis is considered to be undesirable by many patients and their parents due to its invasive nature (disruption of muscle attachment to the spine, increased recovery time, and stiffening of the spinal column resulting in decreased mobility). The metal rods used in fusion techniques are not removable and thus stay within the patient indefinitely. The major disadvantage to a metal rod fusion is loss of spine mobility and the potential for adjacent level disc degeneration in the distal segments of the spine, since all the motion the patient desires is transferred to the remaining levels of the mobile spine.

A more recent development in scoliosis treatment, referred to generally as vertebral body tethering (VBT), is a non-fusion surgery that has been found to provide advantages over bracing and fusion techniques of the prior art. In a VBT scoliosis correction technique, access openings are made at strategic locations in the patient so that portals may be inserted in these openings. The portals enable the surgeon to implant endoscopically a plurality of anchor devices (e.g. titanium screws) onto corresponding vertebral bodies. Each anchor device has a channel disposed therein, such that a tether/cord may be placed into the channels. One end of the tether is secured within a corresponding anchor device. Then, using very limited basic unidirectional maneuvers, the tether is tensioned so as to urge the other channels in which the tether is disposed, along with the corresponding vertebral bodies, towards a straighter orientation. The tether is secured in all the channels using a tensioner, thus urging the spine towards correction of the scoliosis condition. Optionally, the tether may be adjusted during a subsequent follow-up procedure so as to continue to correct the scoliosis condition over a greater period of time. This is particularly beneficial to younger patients whose spine is still growing. The patient often can leave the hospital within a few days of the surgery and may be able to return to normal activities, including athletic activities, within six weeks or so. This tethering technique is described, for example, in U.S. Pat. No. 10,278,736, METHODS AND TECHNIQUES FOR SPINAL SURGERY, the specification of which is incorporated by reference herein.

Although tethering has been found to be more advantageous than fusion for many patients, it may only be effective in limited cases where the angle of scoliosis is in a narrow band, i.e. between 40° and 70°. In addition, VBT techniques may only be applicable to relatively younger patients whose spine is still undergrowing growth and have not reached skeletal maturity (required by VBT). Moreover, VBT may not be as effective in treating complex three-dimensional (i.e. multi-planar) scoliosis, especially rotation which is the main cause of the curvature of the spine.

Additionally, VBT has been most used and shown successful in the thoracic (T5-T12) region of the spine, using single anchor screws and cords. While helping to correct for translational curves ("S" or "C") on a single plane, VBT techniques do not always correct for the multi-planar deformity, especially rotation of the spine that occurs with scoliosis.

SUMMARY OF THE INVENTION

The present invention implements methodologies and techniques that improve upon the VBT methodology of the prior art in order to overcome its deficiencies. In particular, provided are improved methods of performing spinal correction surgery on a patient in which a plurality of vertebrae are adjusted with respect to each other in order to straighten the spine. The improved methods comprise one or more of the following inventive procedures: release of soft disc tissue between adjacent vertebrae, de-rotation of adjacent or nearly adjacent vertebrae, and/or a double screw/double cord implementation, all of which are further described herein.

It is noted that various techniques of the inventors of this application are the subject of the following previously issued U.S. Patents:

- U.S. Pat. No. 11,389,204: METHOD FOR IMPROVED SPINAL CORRECTION SURGERY IMPLEMENTING NON-FUSION ANTERIOR SCOLIOSIS CORRECTION TECHNIQUES FOR RELEASE OF DISCS
- U.S. Pat. No. 11,547,452: METHOD FOR IMPROVED SPINAL CORRECTION SURGERY IMPLEMENTING NON-FUSION ANTERIOR SCOLIOSIS CORRECTION TECHNIQUES WITH VERTEBRAE DE-ROTATION
- U.S. Pat. No. 11,602,376; METHOD FOR IMPROVED SPINAL CORRECTION SURGERY IMPLEMENTING NON-FUSION ANTERIOR SCOLIOSIS CORRECTION TECHNIQUES WITH DOUBLE SCREWS AND CORDS

The first major aspect of the invention set forth in the above patents and also described herein addresses cases of severe scoliosis where discs of soft tissue that are located between adjacent vertebrae may have become too stiff to allow for surgical correction of the vertebrae. In such cases, these discs need to be released to allow for proper correction of the vertebrae. This overall methodology of releasing the discs includes the steps of creating a vertical mini-opening in the side of the patient to enable the surgeon to access directly the vertebrae; performing a disc release procedure on a disc located between a pair of adjacent vertebrae to enable the pair of adjacent vertebrae to be adjusted with respect to each other; inserting an anchor screw into the plurality of vertebrae being operated on, each anchor screw comprising a channel suitable for accepting a tensioning cord; disposing a tensioning cord within the channels of the anchor screws to enable an adjustment procedure on the plurality of vertebrae; and performing a vertebrae adjustment procedure in which each of the plurality of vertebrae is adjusted with respect to at least one other vertebra and the tensioning cord is secured within the channel of the anchor screw of the adjusted vertebra in order to maintain the adjustment.

In some instances, the surgeon may locate the cord through only the anchor screw of the vertebra being corrected, with the rest of the tensioning cord laying to the side, and then locate the cord through the next anchor screw to be tensioned and secured, one anchor screw at a time. In the alternative, the surgeon may locate the tensioning cord through all of the anchor screws along the spine, and then proceed with the correction (de-rotation) of each vertebra, tensioning and securing the cord within each anchor screw accordingly.

The anchor screws may be inserted in various positions on the side of the vertebrae; they may be inserted substantially in the center of the side of each of the vertebrae, and/or offset horizontally from the center of the side of the vertebrae whereby the tensioning cord is offset horizontally and located more towards the posterior in the middle of the spine, and/or offset vertically from the center of the side of the vertebrae. This alternative placement of the anchor screws may help to create a better de-rotation correction force vector if desired by the surgeon.

In particular, the step of performing a disc release procedure on a disc located between adjacent vertebrae of the spine of the patient comprises incising a disc near its center to allow additional movement of the adjacent vertebrae during the operation.

Optionally, if required, a distraction procedure may be performed on at least one pair of adjacent vertebrae of the spine of the patient by inserting a paddle in a previously released disc between two vertebrae adjacent the vertebrae to be compressed and rotating the paddle in order to urge the adjacent vertebrae together.

In certain cases, the disc release procedure is performed prior to the step of inserting the anchor screw into each of the plurality of vertebrae being operated on, while in certain other cases the disc release procedure is performed subsequent to the step of inserting the anchor screw into each of the plurality of vertebrae being operated on.

In one embodiment, the step of creating a vertical mini-opening in the side of the patient to enable the surgeon to access directly the plurality of the vertebrae comprises the patient lying on her side on an operating table, placing an x-ray machine over the exposed side of the patient, marking a line on the skin of the patient along over the vertebrae to be operated on as indicated by the x-ray machine, and incising the skin of the patient along a portion of the marked line to create the mini-opening, which for example may be between approximately four and six inches in length. Optionally, a portal may be inserted into at a least one location along the marked line of the patent outside of the incised mini-opening to create access to vertebrae outside of the mini-opening by cutting a plane under the skin adjacent to the mini-opening and lifting the skin adjacent to the mini-opening to enable access to the interspace under the skin adjacent to the mini-opening.

In some embodiments, a segmental vessel preservation procedure may be performed on at least one vessel adjacent a vertebra prior to inserting the anchor screw into the vertebra, by inserting a surgical instrument under the segmental vessel adjacent the vertebra and retracting the segmental vessel away from the vertebra so as to allow inserting an anchor screw into the vertebrae without damaging the segmental vessel. In certain embodiments, an additional step of de-compressing a disc may be performed between adjacent vertebrae using a spreader to spread the adjacent vertebrae with respect to each other.

In a second major aspect set forth in the above patents and also described herein, the vertebrae adjustment procedure is a de-rotation procedure, which comprises locating a stationary tower on a first anchor screw of a first vertebra; locating a de-rotation tower on a second anchor screw of a second vertebra; and performing a de-rotation maneuver by applying a downwards translational force vector to the de-rotation tower, applying a lateral force vector to the de-rotation tower, and simultaneously applying a lateral counterforce vector to the stationary tower in opposition to the lateral force vector being applied to the de-rotation tower. After this de-rotation maneuver is performed, then the cord is tensioned in channel of the second anchor screw, and the tensioned cord is secured in the channel of the second anchor screw in order to maintain the de-rotation.

Next, the de-rotation tower is re-located to the next vertebra and the de-rotation maneuver is repeated. After several vertebrae have been de-rotated in this manner, then the stationary tower is re-located to an adjacent vertebra so that the stationary tower and the de-rotation tower are not separated by more than several vertebrae during any one de-rotation procedure.

In a third major aspect set forth in the above patents and also described herein, two sets of anchor screws and two tensioning cords (double screws/double cords) are utilized in order to provide for greater de-rotational stability and longevity than otherwise obtained by the use of single set of anchor screws and a single tensioning cord.

In a first example, involving a single curve of the spine, provided is an improved method of performing spinal correction surgery on a patient in which a plurality of vertebrae are adjusted with respect to each other using a double screw/double cord methodology. In this method, a vertical mini-opening is created in the side of the patient to enable the surgeon to access directly the plurality of the vertebrae. A pair of anchor screws is inserted into each of the plurality of vertebrae being operated on, each of the anchor screws having a channel suitable for accepting a tensioning cord, such that a substantially aligned posterior row of posterior anchor screws are formed along the vertebrae next to a substantially aligned anterior row of anterior anchor screws formed along the vertebrae.

A posterior tensioning cord is disposed within the channels of the posterior row of posterior anchor screws to enable a posterior adjustment procedure on the plurality of vertebrae in which each of the plurality of vertebrae is adjusted with respect to at least one other vertebra and the posterior tensioning cord is secured within the channels of the corresponding posterior anchor screws in order to maintain the posterior adjustment of the vertebrae.

An anterior tensioning cord is disposed within the channels of each of the anterior row of anterior anchor screws to enable an anterior adjustment procedure on the plurality of vertebrae in which each of the plurality of vertebrae is adjusted with respect to at least one other vertebra and the anterior tensioning cord is secured within the channels of the corresponding anterior anchor screws in order to obtain additional correction and additional rotational stability.

Either or both of the posterior vertebrae adjustment procedure and the anterior vertebrae adjustment procedure may for example be a de-rotation procedure. Thus, if a de-rotation procedure is implemented for the posterior vertebrae adjustment procedure, this includes the steps of locating a stationary tower on a first posterior anchor screw of a first vertebra, locating a de-rotation tower on a second posterior anchor screw of a second vertebra, performing a de-rotation maneuver by applying a downwards translational force vector to the de-rotation tower, applying a lateral force vector to the de-rotation tower, and simultaneously applying a lateral counterforce vector to the stationary tower in opposition to the lateral force vector being applied to the de-rotation tower, tensioning the posterior tensioning cord in the channel of the second posterior anchor screw, securing the posterior tensioning cord in the channel of at the second posterior anchor screw, re-locating the de-rotation tower to the posterior anchor screw of a subsequent vertebra, and repeating the de-rotation maneuver until all of the vertebrae have been de-rotated as desired.

Similarly, when the anterior vertebrae adjustment procedure is a de-rotation procedure, this includes the steps of locating a stationary tower on a first anterior anchor screw of a first vertebra, locating a de-rotation tower on a second anterior anchor screw of a second vertebra, performing a de-rotation maneuver by applying a downwards translational force vector to the de-rotation tower, applying a lateral force vector to the de-rotation tower, and simultaneously applying a lateral counterforce vector to the stationary tower in opposition to the lateral force vector being applied to the de-rotation tower, tensioning the anterior tensioning cord in the channel of the second anterior anchor screw, securing the anterior tensioning cord in the channel of at the second anterior anchor screw in order to maintain the de-rotation of the vertebrae, re-locating the de-rotation tower to the anterior anchor screw of a subsequent vertebra, and repeating the de-rotation maneuver until all of the vertebrae have been de-rotated as desired.

Since the initial posterior vertebrae adjustment procedure has likely substantially aligned the vertebrae, the amount of adjustment provided by the anterior vertebrae adjustment procedure may be only incremental, but is still useful in maintaining alignment of the vertebrae. In an alternative embodiment, the anterior vertebrae adjustment procedure may be executed before the posterior vertebrae adjustment procedure, if desired.

In an alternate embodiment, the anterior tensioning cord crosses over from the anterior row of anterior anchor screws to the posterior row of posterior anchor screws such that the anterior tensioning cord is disposed (and tensioned/secured) within the channel of at least one of the posterior anchor screws. Likewise, in some cases, the posterior tensioning cord crosses over from the posterior row of posterior anchor screws to the anterior row of anterior anchor screws such that the posterior tensioning cord is disposed (and tensioned/secured) within the channel of at least one of the anterior anchor screws.

In a second example, involving a double curve of the spine, provided is an improved method of performing spinal correction surgery on a patient in which a plurality of vertebrae are adjusted with respect to each other using a double screw/double cord methodology, wherein a plurality of anchor screws are inserted into corresponding vertebrae to enable the spinal correction, and wherein each of the anchor screws comprises a channel suitable for accepting a tensioning cord. The vertebrae forms a double scoliosis curve comprising an upper curve defined by an upper set of vertebrae disposed substantially in a first direction, a lower curve defined by a lower set of vertebrae disposed substantially in a second direction substantially opposite to the first direction, and a single neutral vertebra located between the upper set of vertebrae and the lower set of vertebrae.

In this method, a vertical mini-opening is created in the side of the patient to enable the surgeon to access directly the plurality of the vertebrae. For the upper set of vertebrae, a pair of anchor screws is inserted into each of the plurality of upper vertebrae along the convexity (outside) of the upper curve, such that a substantially aligned upper posterior row of upper posterior anchor screws are formed along the upper vertebrae next to a substantially aligned upper anterior row of upper anterior anchor screws formed along the upper vertebrae. Similarly, for the lower set of vertebrae, a pair of anchor screws is inserted into each of the plurality of lower vertebrae along the convexity of the lower curve which is substantially opposite the convexity of the upper curve, such that a substantially aligned lower posterior row of lower posterior anchor screws is formed along the lower vertebrae next to a substantially aligned lower anterior row of lower anterior anchor screws formed along the lower vertebrae. For the neutral vertebra, an upper neutral anchor screw is inserted into the neutral vertebra on the same side as the upper curve, and a lower neutral anchor screw is inserted into the neutral vertebra on the same side as the lower curve.

An upper posterior tensioning cord is disposed within the channels of the upper posterior row of upper posterior anchor screws and the upper neutral anchor screw, and an upper bridge tensioning cord is disposed within the channels of the upper neutral anchor screw and the upper posterior anchor screw adjacent the upper neutral anchor screw to enable an upper posterior adjustment procedure on the upper set of vertebrae. An upper posterior vertebrae adjustment procedure is performed in which each of the set of upper vertebrae is adjusted with respect to at least one other upper vertebra and the upper posterior tensioning cord and upper bridge tensioning cord are each secured within the channels of the corresponding upper posterior anchor screws (and the upper neutral anchor screw) in order to maintain the upper posterior adjustment of the vertebrae. For example, the upper posterior vertebrae adjustment procedure may be a de-rotation procedure comprising the steps of locating a stationary tower on a first upper posterior anchor screw of a first upper vertebra, locating a de-rotation tower on a second upper posterior anchor screw of a second upper vertebra, performing a de-rotation maneuver by applying a downwards translational force vector to the de-rotation tower, applying a lateral force vector to the de-rotation tower, and simultaneously applying a lateral counterforce vector to the stationary tower in opposition to the lateral force vector being applied to the de-rotation tower, tensioning the upper posterior tensioning cord in the channel of the second upper posterior anchor screw, securing the upper posterior tensioning cord in the channel of the second upper posterior anchor screw in order to maintain the de-rotation of the upper vertebrae, re-locating the de-rotation tower to the upper posterior anchor screw of a subsequent upper vertebra, and repeating the de-rotation maneuver until all of the upper vertebrae have been de-rotated as desired. When adjusting the neutral vertebra, both the upper posterior tensioning cord and the upper bridge tensioning cord are tensioned and secured simultaneously.

An upper anterior tensioning cord is disposed within the channels of each of the upper anterior row of upper anterior anchor screws to enable an upper anterior adjustment procedure on the upper set of vertebrae. Next, an upper anterior vertebrae adjustment procedure is performed in which each of the set of upper vertebrae is adjusted with respect to at least one other upper vertebra and the upper anterior tensioning cord is secured within the channel of the corresponding upper anterior anchor screw in order to maintain the upper anterior adjustment of the vertebrae. For example, the upper anterior vertebrae adjustment procedure may be a de-rotation procedure comprising the steps of locating a stationary tower on a first upper anterior anchor screw of a first upper vertebra, locating a de-rotation tower on a second upper anterior anchor screw of a second upper vertebra, performing a de-rotation maneuver by applying a downwards translational force vector to the de-rotation tower, applying a lateral force vector to the de-rotation tower, and simultaneously applying a lateral counterforce vector to the stationary tower in opposition to the lateral force vector being applied to the de-rotation tower, tensioning the upper anterior tensioning cord in the channel of the second upper anterior anchor screw, securing the upper anterior tensioning cord in the channel of the second upper anterior anchor screw in order to maintain the de-rotation of the upper vertebrae, re-locating the de-rotation tower to the upper anterior anchor screw of a subsequent upper vertebra, and repeating the de-rotation maneuver until all of the upper vertebrae have been de-rotated as desired.

Similarly, a lower posterior tensioning cord is disposed within the channels of the lower posterior row of lower posterior anchor screws and the lower neutral anchor screw, and a lower bridge tensioning cord is disposed within the channels of the lower neutral anchor screw and the lower posterior anchor screw adjacent the lower neutral anchor screw to enable a lower posterior adjustment procedure on the lower set of vertebrae. A lower posterior vertebrae adjustment procedure is performed in which each of the set of lower vertebrae is adjusted with respect to at least one other lower vertebra and the lower posterior tensioning cord and lower bridge tensioning cord are each secured within the channels of the corresponding lower posterior anchor screws (and the lower neutral anchor screw) in order to maintain the lower posterior adjustment of the vertebrae. For example, the lower posterior vertebrae adjustment procedure may be a de-rotation procedure comprising the steps of locating a stationary tower on a first lower posterior anchor screw of a first lower vertebra, locating a de-rotation tower on a second lower posterior anchor screw of a second lower vertebra, performing a de-rotation maneuver by applying a downwards translational force vector to the de-rotation tower, applying a lateral force vector to the de-rotation tower, and simultaneously applying a lateral counterforce vector to the stationary tower in opposition to the lateral force vector being applied to the de-rotation tower, tensioning the lower posterior tensioning cord in the channel of the second lower posterior anchor screw, securing the lower posterior tensioning cord in the channel of the second lower posterior anchor screw in order to maintain the de-rotation of the lower vertebrae, re-locating the de-rotation tower to the lower posterior anchor screw of a subsequent lower vertebra, and repeating the de-rotation maneuver until all of the lower vertebrae have been de-rotated as desired. When adjusting the neutral vertebra, both the lower posterior tensioning cord and the lower bridge tensioning cord are tensioned and secured simultaneously.

A lower anterior tensioning cord is disposed within the channels of the lower anterior row of lower anterior anchor screws to enable a lower anterior adjustment procedure on the lower set of vertebrae. A lower anterior vertebrae adjustment procedure is performed in which each of the set of lower vertebrae is adjusted with respect to at least one other lower vertebra and the lower anterior tensioning cord is secured within the channels of the corresponding lower anterior anchor screws in order to maintain the lower anterior adjustment of the lower vertebrae. For example, the lower anterior vertebrae adjustment procedure may be a de-rotation procedure comprising the steps of locating a stationary tower on a first lower anterior anchor screw of a first lower vertebra, locating a de-rotation tower on a second lower anterior anchor screw of a second lower vertebra, performing a de-rotation maneuver by applying a downwards translational force vector to the de-rotation tower, applying a lateral force vector to the de-rotation tower, and simultaneously applying a lateral counterforce vector to the stationary tower in opposition to the lateral force vector being applied to the de-rotation tower, tensioning the lower anterior tensioning cord in the channel of the second lower anterior anchor screw, securing the lower anterior tensioning cord in the channel of the second lower anterior anchor screw in order to maintain the de-rotation of the lower vertebrae, re-locating the de-rotation tower to the lower anterior anchor screw of a subsequent lower vertebra, and repeating the de-rotation maneuver until all of the lower vertebrae have been de-rotated as desired.

In some instances of a double curve, a crossover technique may also be implemented where the use of the upper bridge tensioning cord is eliminated, and the upper anterior tensioning cord extends through the upper anterior screw and over to and through the upper neutral anchor screw. Likewise, at the lumbar portion, the lower bridge tensioning cord may be eliminated, and the lower anterior tensioning cord may extend through the lower anterior screw and over to and through the lower neutral anchor screw.

In another embodiment, a further modification of the crossover cord technique is implemented using crisscrossed tensioning cords wherein a tensioning cord crosses over from one row of anchor screws to the other row of anchor screws and back, one or more times, in a crisscross or weaved type of pattern. Either or both of the tensioning cords may crisscross in this manner, thus providing further advantages in de-rotation of the spine by providing greater strength and control of the corrected vertebrae, for example. These crisscrossed tensioning cords may be implemented alone or in conjunction with single or double straight tensioning cords.

As taught in further herein, these three major aspects of the invention are the releasing of discs, the use of de-rotation maneuvers, and the use of double screws/double cords. Each of these three major aspects of the invention may be used independently of the others, or if applicable a surgeon may use any two of these techniques or all three of these techniques as desired. For example, the de-rotation methodologies described herein may be implemented with a single screw/single cord application, but if the patient's scoliosis is so severe that double screws/double cords are required, then the de-rotation may be implemented with double screws/double cords. In that case, the surgeon would implement the de-rotation correction techniques with the first set of screws/cord (i.e. the posterior set), and then repeat the same maneuvers with the second set (the anterior set). Similarly, the disc release procedure may not be applicable or even advisable in certain situations, in which case it would not be performed by the surgeon.

Since each of the three major methodologies described herein address different problems encountered by the surgeon as described, it is up to the surgeon using professional judgment and experience which of these methodologies, and in which combination, would be best suited for a given procedure.

The present invention improves on the above patents in several ways, as follows.

In one improved aspect, the vertebrae of the patient may have enough mass to support additional anchor screws at the neutral (i.e. transition) zone around T12. In this embodiment, provided is an improved method of performing spinal correction surgery on a patient in which a plurality of vertebrae are adjusted with respect to each other using a double screw/double cord methodology, wherein a plurality of anchor screws are inserted into corresponding vertebrae to enable the spinal correction, wherein each of the anchor screws comprises a channel suitable for accepting a tensioning cord; the vertebrae forming a double scoliosis curve comprising an upper curve defined by an upper set of vertebrae disposed substantially in a first direction, a lower curve defined by a lower set of vertebrae disposed substantially in a second direction substantially opposite to the first direction, and a neutral vertebra located between the upper set of vertebrae and the lower set of vertebrae;

The method comprises the steps of creating a vertical mini-opening in the side of the patient to enable the surgeon to access directly the plurality of the vertebrae.

For the upper set of vertebrae, a pair of anchor screws is inserted into each of the plurality of upper vertebrae and the neutral vertebra along the convexity of the upper curve, such that a substantially aligned upper posterior row of upper posterior anchor screws are formed along the upper vertebrae and the neutral vertebra next to a substantially aligned upper anterior row of upper anterior anchor screws formed along the upper vertebrae and the neutral vertebra.

For the lower set of vertebrae, a pair of anchor screws is inserted into each of the plurality of lower vertebrae and the neutral vertebra along the convexity of the lower curve which is substantially opposite the convexity of the upper curve, such that a substantially aligned lower posterior row of lower posterior anchor screws are formed along the lower vertebrae and the neutral vertebra next to a substantially aligned lower anterior row of lower anterior anchor screws formed along the lower vertebrae and the neutral vertebra.

An upper posterior tensioning cord is disposed within the channels of the upper posterior row of upper posterior anchor screws to enable an upper posterior adjustment procedure on the upper set of vertebrae and the neutral vertebra. An upper posterior vertebrae adjustment procedure is performed in which each of the set of upper vertebrae and the neutral vertebra is adjusted with respect to at least one other upper vertebra and the upper posterior tensioning cord is secured within the channel of the corresponding upper posterior anchor screw in order to maintain the upper posterior adjustment of the vertebrae.

An upper anterior tensioning cord is disposed within the channels of the upper anterior row of upper anterior anchor screws to enable an upper anterior adjustment procedure on the upper set of vertebrae and the neutral vertebra. An upper anterior vertebrae adjustment procedure is performed in which each of the set of upper vertebrae and the neutral vertebra is adjusted with respect to at least one other upper vertebra and the upper anterior tensioning cord is secured within the channel of the corresponding upper anterior anchor screw in order to maintain the upper anterior adjustment of the vertebra.

A lower posterior tensioning cord is disposed within the channels of the lower posterior row of lower posterior anchor screws to enable a lower posterior adjustment procedure on the lower set of vertebrae and the neutral vertebra. A lower posterior vertebrae adjustment procedure is performed in which each of the set of lower vertebrae and the neutral vertebra is adjusted with respect to at least one other lower vertebra and the lower posterior tensioning cord is secured within the channel of the corresponding lower posterior anchor screw in order to maintain the lower posterior adjustment of the vertebrae.

A lower anterior tensioning cord is disposed within the channels of the lower anterior row of lower anterior anchor screws to enable a lower anterior adjustment procedure on the lower set of vertebrae and the neutral vertebra. A lower anterior vertebrae adjustment procedure is performed in which each of the set of lower vertebrae and the neutral vertebra is adjusted with respect to at least one other lower vertebra and the lower anterior tensioning cord is secured within the channel of the corresponding lower anterior anchor screw in order to maintain the lower anterior adjustment of the vertebrae.

In an optional embodiment, a second upper posterior tensioning cord is disposed within the channels of the upper posterior row of upper posterior anchor screws next to the upper posterior tensioning cord; a second upper anterior tensioning cord is disposed within the channels of the upper anterior row of upper anterior anchor screws next to the upper anterior tensioning cord; a second lower posterior tensioning cord is disposed within the channels of the lower posterior row of lower posterior anchor screws next to the lower posterior tensioning cord; and a second lower anterior tensioning cord is disposed within the channels of the lower anterior row of lower anterior anchor screws next to the lower anterior tensioning cord.

Optionally, the upper posterior vertebrae adjustment procedure is a de-rotation procedure comprising the steps of locating a stationary tower on a first upper posterior anchor screw of a first upper vertebra, locating a de-rotation tower on a second upper posterior anchor screw of a second upper vertebra, performing a de-rotation maneuver by applying a downwards translational force vector to the de-rotation tower, applying a lateral force vector to the de-rotation tower, and simultaneously applying a lateral counterforce vector to the stationary tower in opposition to the lateral force vector being applied to the de-rotation tower, tensioning the upper posterior tensioning cord in the channel of the second upper posterior anchor screw, securing the upper posterior tensioning cord in the channel of the second upper posterior anchor screw in order to maintain the de-rotation of the upper vertebrae, re-locating the de-rotation tower to the upper posterior anchor screw of a subsequent upper vertebra, and repeating the de-rotation maneuver until all of the upper vertebrae and the neutral vertebra have been de-rotated as desired.

Further optionally, the upper anterior vertebrae adjustment procedure is a de-rotation procedure comprising the steps of locating a stationary tower on a first upper anterior anchor screw of a first upper vertebra, locating a de-rotation tower on a second upper anterior anchor screw of a second upper vertebra, performing a de-rotation maneuver by applying a downwards translational force vector to the de-rotation tower, applying a lateral force vector to the de-rotation tower, and simultaneously applying a lateral counterforce vector to the stationary tower in opposition to the lateral force vector being applied to the de-rotation tower, tensioning the upper anterior tensioning cord in channel of the second upper anterior anchor screw, securing the upper anterior tensioning cord in the channel of the second upper anterior anchor screw in order to maintain the de-rotation of the upper vertebrae, re-locating the de-rotation tower to the upper anterior anchor screw of a subsequent upper vertebra, and repeating the de-rotation maneuver until all of the upper vertebrae and the neutral vertebra have been de-rotated as desired.

Still further optionally, the lower posterior vertebrae adjustment procedure is a de-rotation procedure comprising the steps of locating a stationary tower on a first lower posterior anchor screw of a first lower vertebra, locating a de-rotation tower on a second lower posterior anchor screw of a second lower vertebra, performing a de-rotation maneuver by applying a downwards translational force vector to the de-rotation tower, applying a lateral force vector to the de-rotation tower, and simultaneously applying a lateral counterforce vector to the stationary tower in opposition to the lateral force vector being applied to the de-rotation tower, tensioning the lower posterior tensioning cord in channel of the second lower posterior anchor screw, securing the lower posterior tensioning cord in the channel of the second lower posterior anchor screw in order to maintain the de-rotation of the lower vertebrae, re-locating the de-rotation tower to the lower posterior anchor screw of a subsequent lower vertebra, and repeating the de-rotation maneuver until all of the lower vertebrae and the neutral vertebra have been de-rotated as desired.

Finally, the lower anterior vertebrae adjustment procedure may be a de-rotation procedure comprising the steps of locating a stationary tower on a first lower anterior anchor screw of a first lower vertebra, locating a de-rotation tower on a second lower anterior anchor screw of a second lower vertebra, performing a de-rotation maneuver by applying a downwards translational force vector to the de-rotation tower, applying a lateral force vector to the de-rotation tower, and simultaneously applying a lateral counterforce vector to the stationary tower in opposition to the lateral force vector being applied to the de-rotation tower, tensioning the lower anterior tensioning cord in channel of the second lower anterior anchor screw, securing the lower anterior tensioning cord in the channel of the second lower anterior anchor screw in order to maintain the de-rotation of the lower vertebrae, re-locating the de-rotation tower to the lower anterior anchor screw of a subsequent lower vertebra, and repeating the de-rotation maneuver until all of the lower vertebrae and the neutral vertebra have been de-rotated as desired.

In another improved aspect, two tensioning cords may be used instead of a single tensioning cord, which provides redundancy in the event one of the cords breaks over time. In this respect, provided is an embodiment using a single row of anchor screws and dual cords, in particular an improved method of performing spinal correction surgery on a patient in which a plurality of vertebrae are adjusted with respect to each other, comprising the steps of: creating a vertical mini-opening in a side of the patient to enable the surgeon to access directly the plurality of the vertebrae without use of a portal; inserting, via the mini-opening, an anchor screw into each of the plurality of vertebrae being operated on, each anchor screw comprising a channel suitable for accepting a pair of flexible tensioning cords; disposing, via the mini-opening, a pair of flexible tensioning cords, comprising a first flexible tensioning cord and a second flexible tensioning cord, within the channels of the anchor screws to enable an adjustment procedure on the plurality of vertebrae; and performing a vertebrae adjustment procedure by tensioning with a tensioner the first flexible tensioning cord in the channel of a first anchor screw; tensioning by hand the second flexible tensioning cord in the channel of the first anchor screw; and securing the first flexible tensioning cord and the second flexible tensioning cord in the channel of a second anchor screw in order to maintain the adjustment of the vertebrae.

Similarly, dual cords may be used in each row of a double row embodiment (four cords total). Here, provided is an improved method of performing spinal correction surgery on a patient in which a plurality of vertebrae are adjusted with respect to each other, comprising the steps of: creating a vertical mini-opening in a side of the patient to enable the surgeon to access directly the plurality of the vertebrae without use of a portal; inserting, via the mini-opening, a pair of anchor screws into each of the plurality of vertebrae being operated on, each of the anchor screws comprising a channel suitable for accepting a pair of flexible tensioning cords, such that a substantially aligned posterior row of posterior anchor screws are formed along the vertebrae next to a substantially aligned anterior row of anterior anchor screws formed along the vertebrae; disposing a first pair of flexible tensioning cords, comprising a first flexible tensioning cord and a second flexible tensioning cord, within the channels of the posterior row of posterior anchor screws to enable a posterior vertebrae adjustment procedure on the plurality of vertebrae; performing a posterior vertebrae adjustment procedure by tensioning with a tensioner the first flexible tensioning cord in the channel of a first posterior anchor screw; tensioning by hand the second flexible tensioning cord in the channel of the first posterior anchor screw; and securing the first flexible tensioning cord and the second flexible tensioning cord in the channel of a second posterior anchor screw in order to maintain the adjustment of the vertebrae; disposing a second pair of flexible tensioning cords, comprising a third flexible tensioning cord and a fourth flexible tensioning cord, within the channels of the anterior row of anterior anchor screws to enable an anterior vertebrae adjustment procedure on the plurality of vertebrae; performing an anterior vertebrae adjustment procedure by tensioning with the tensioner the third flexible tensioning cord in the channel of a first anterior anchor screw; tensioning by hand the fourth flexible tensioning cord in the channel of the first anterior anchor screw; and securing the third flexible tensioning cord and the fourth flexible tensioning cord in the channel of a second anterior anchor screw in order to maintain the adjustment of the vertebrae.

In another improved aspect, the anchor screws may be horizontally and/or vertically offset from center, in both a single row and double row embodiment. In the single row embodiment, provided is an improved method of performing spinal correction surgery on a patient in which a plurality of vertebrae are adjusted with respect to each other, comprising the steps of creating a vertical mini-opening in a side of the patient to enable the surgeon to access directly the plurality of the vertebrae without use of a portal; inserting, via the mini-opening, an anchor screw into each of the plurality of vertebrae being operated on, each anchor screw comprising a channel suitable for accepting a flexible tensioning cord; disposing, via the mini-opening, a flexible tensioning cord within the channels of the anchor screws to enable an adjustment procedure on the plurality of vertebrae; and performing a vertebrae adjustment procedure which each of the plurality of vertebrae is adjusted with respect to at least one other vertebra and the flexible tensioning cord is secured within the channel of the corresponding anchor screw of the adjusted vertebra in order to maintain the adjustment of the vertebrae wherein (1) each of the plurality of anchor screws is inserted into substantially the center of the side of each of the vertebrae, or (2) at least some of the plurality of anchor screws are offset horizontally from the center of the side of the vertebrae whereby the tensioning cord is offset horizontally and located more towards the posterior in the middle of the spine, or (3) at least some of the plurality of anchor screws are offset horizontally from the center of the side of the vertebrae whereby the tensioning cord is offset horizontally and located more towards the anterior in the middle of the spine, or (4) at least some of the plurality of anchor screws are offset vertically from the center of the side of the vertebrae.

In the double row embodiment, provided is an improved method of performing spinal correction surgery on a patient in which a plurality of vertebrae are adjusted with respect to each other using a double screw/double cord methodology, comprising the steps of creating a vertical mini-opening in a side of the patient to enable the surgeon to access directly the plurality of the vertebrae without use of a portal; inserting a pair of anchor screws via the mini-opening into each of the plurality of vertebrae being operated on, each of the anchor screws comprising a channel suitable for accepting a flexible tensioning cord, such that a posterior row of posterior anchor screws are formed along the vertebrae next to an anterior row of anterior anchor screws formed along the vertebrae; disposing a flexible posterior tensioning cord within the channels of the posterior row of posterior anchor screws to enable a posterior adjustment procedure on each of the plurality of vertebrae; performing a posterior vertebrae adjustment procedure in which each of the plurality of vertebrae is adjusted with respect to at least one other vertebra and the flexible posterior tensioning cord is secured within the channels of the posterior anchor screws at a first tension in order to maintain adjustment of the vertebrae; disposing a flexible anterior tensioning cord within the channels of the anterior row of anterior anchor screws to enable an anterior adjustment procedure on the plurality of vertebrae; and performing an anterior vertebrae adjustment procedure in which each of the plurality of vertebrae is adjusted with respect to at least one other vertebra and the flexible anterior tensioning cord is secured within the channels of the anterior anchor screws at a second tension that is different from the first tension in order to maintain adjustment of the vertebrae; wherein (1) at least some of the plurality of anchor screws in the posterior row are offset horizontally from other anchor screws in the posterior row; or (2) at least some of the plurality of anchor screws in the anterior row are offset horizontally from other anchor screws in the anterior row; or (3) at least some of the plurality of anchor screws in the posterior row are offset vertically from other anchor screws in the posterior row; or (4) at least some of the plurality of anchor screws in the anterior row are offset vertically from other anchor screws in the anterior row.

BRIEF DESCRIPTION OF THE DRAWING

FIG. 3 illustrates the patient of FIG. 2 showing the use of a Steinman pin in conjunction with intra operative x-ray imaging of the lateral spine for determining positioning of the midline of the vertebral bodies being operated on.

FIG. 26 is a is a thoracic side elevation, taken at arrow 26 of FIG. 25, showing the double screw/double cord set up.

FIG. 26A is an enlarged perspective view, taken at arrow 26a of FIG. 26, showing the anchor screws and cord doubling.

FIG. 27 is a lumbar side elevation, taken at arrow 27 of FIG. 25, showing the double screw/double cord set up.

FIG. 27A is an enlarged perspective view, taken at arrow 27a of FIG. 27, showing the anchor screws and cord doubling.

FIG. 30 illustrates an alternative embodiment in which a subset of the anchor screws are offset vertically from the center of the side of the vertebrae; this example shows screw in most inferior position of the L1 vertebra.

FIG. 31 illustrates the tensioning cord inserted through the vertically offset anchor screws after correction; this example shows screw in most inferior position of the L1 vertebrae.

FIG. 34A illustrates an alternative embodiment in which the thoracic portion of the spine has a double screw/double cord embodiment with a pair of straight tensioning cords and a posterior crossover tensioning cord.

FIG. 34B illustrates the alternative embodiment of FIG. 34a in which the thoracic portion of the spine has a double screw/double cord embodiment with a pair of straight tensioning cords, a posterior crossover tensioning cord, and an anterior crossover tensioning cord.

FIG. 43 illustrates an alternative embodiment in which double rows of anchor screws are inserted posterior and/or anterior to the center line; this example shows the screws in the most inferior position of the L1 vertebrae.

FIG. 44 illustrates an alternative embodiment in which double rows of anchor screws are inserted superior and/or inferior to the center line; this example shows the screws in the most inferior position of the L1 vertebrae.

DETAILED DESCRIPTION OF THE INVENTION

General Characteristics of the Present Invention

Figure 1:
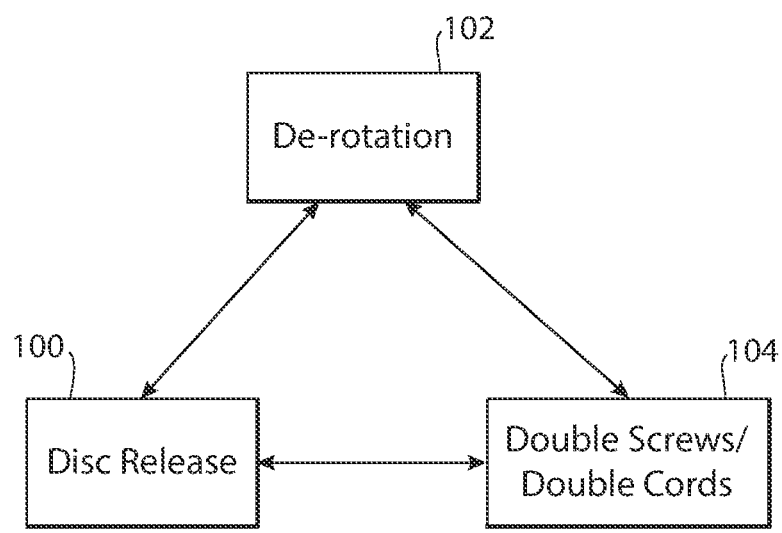
FIG. 1 is a diagram showing the three major aspects of the present invention.

Described herein are improved surgical methodologies for correcting scoliosis that overcome the disadvantages of the prior art, including but not limited to those described herein. Referred to as non-fusion anterior scoliosis correction (NFASC), the present invention as illustrated in FIG. 1 implements soft tissue disc releases 100 for optimal correction of the curvatures of the spine, multi-planar (three-dimensional) de-rotation of the spine 102, and the use of double screws/double cords 104 in certain cases. These improved NFASC methodologies are less invasive, result in minimal muscle damage, and may be applied to a variety of scoliosis types, including those with a thoracic, thoracolumbar or lumbar curve(s) of any magnitude. As set forth herein, depending in the type and degree of severity of the scoliosis being addressed, the surgeon may opt to implement any or all of these inventive techniques in various combinations.

Generally speaking, the NFASC techniques described herein use growth modulation and remodeling, which partially restrains one side of the spine to allow growth and remodeling on the other side in order to reverse the abnormal scoliosis growth pattern or residual deformity in the vertebral body and disc. As described further below, titanium pedicle anchor screws are placed on the convexity (outside) of the vertebra that are within the scoliosis curve, and a white polyethylene-terephthalate flexible tensioning cord is disposed within each of the anchor screws in the vertebral bodies of the spine. After the vertebra is adjusted and the tensioning cord is tensioned and secured (tightened) within the anchor screws, the resulting adjustment corrects and straightens the spine. The affected curve(s) show an improvement immediately after surgery, and continued improvement over time as the spine grows. In patients whose spine is not growing, their spine remodels to the new position of the spine held by the anchor screws and tensioning cords.

The improved NFASC techniques of the present invention implement several improvements over the prior art. For example, the use of portals in the prior art, such as described in the '736 patent referenced above, is partially or wholly eliminated by using a mini-opening approach, which advantageously allows direct access to the center of the spine deformity. Portals as used in the prior art scoliosis surgical techniques are inhibitive in several ways, including unduly limiting the view of the interior of the patient by the surgeon and limiting the maneuvers the surgeon can make. By using a small opening (referred to as a mini-opening) in the patient, rather than fixed-diameter portals, the surgeon can get a better view of the areas being operated on, as well as gain increased maneuverability within the patient to accomplish the maneuvers required by this technique. When the scoliosis curves are too large and/or stiff, complete three-dimensional correction through prior art cord tethering cannot be accomplished through the portals, and the mini-open approach solves that problem. Also, mini-open access without portals allows access to lumbar curves, whereas the prior art portal-based VBT methodology does not.

Notwithstanding, portals may be useful at the end of the scoliosis curves for additional anchor screw fixation points depending on the length of the spine and the number of vertebrae involved. This mini-open approach implements the process of making small vertical incisions hidden under the arms of the patient, rather than oblique incisions or posterior incisions as in posterior spinal metal rod fusion. VBT also uses openings in the side of the patient, but portals are used to give access to the surgeon of the vertebra being operated on. Portals within the center of the scoliotic curve are restricted by the ribs and thus cannot be moved as desired during surgery. Thus, stiff (non-flexible) and larger curves (less than 60°) usually cannot be addressed by VBT using the prior art portal technique.

Rather than tethering as in the prior art VBT technique, the present invention applies what is referred to as a de-tethering approach through the use of soft tissue disc releases. In the prior art VBT technique, the manipulations made in the tethering process are only very small due to the use of limiting portals. Mini-open procedures, without using prior art portals, enable more complex and greater amounts of manipulations during the surgery. The NFASC approach of the present invention uses a disc release technique to enable de-rotation of the spine more aggressively than with prior art VBT portal-based techniques. The correction obtained is held in place by using the anchor screw/cord instrumentation.

Thus, NFASC is used to release the ligaments as may be required and thus loosen the spine, which enables optimal correction of the patient's scoliosis through de-rotation and/or double screws/double cords. With many occurrences of scoliosis, on the inside of every curve are ligaments and the disc annulus (hereinafter referred to as soft tissue) that contracts and cannot stretch out enough to allow for straightening of the spine. De-rotational correction is advantageously attained with release of these soft tissues as described further herein.

A unique aspect of this inventive technique is using the now released disc space to assist with correction while the surgeon is tensioning and securing the cord. The surgeon can place an instrument called a disc space trial and help move the vertebra proxillaly, reducing the risk of the anchor screw plowing in the vertebra.

Thus, by using the mini-opening approach rather than just prior art portals, implementation is realized of the inventive disc release, three-dimensional de-rotational maneuver, and double screw/double cord procedures. Notably, the NFASC techniques of the present invention enable de-rotation of the spine to the normal position, while traditional rod based and VBT techniques do not provide or allow for such intricate de-rotation. De-rotation of the spine is especially advantageous in the cases wherein there are multiple aspects of the scoliosis on more than one plane, rather than a simple single-plane correction that is addressed by the prior art.

Furthermore, the use of the mini-open procedures allows for strategic and precise placement of the anchor screws. The use of portals in the prior art allows the surgeon only limited access to the vertebra for placement of the anchor screws. By eliminating the portals through the mini-open procedure, the surgeon can more easily place the anchor screws in specific and strategic locations above and below the segmental vessels as desired and preserve them from being damaged during the operation. The prior art portal-based techniques do not allow for such precise placement of the anchor screws and segmental vessel preservation.

In a third major aspect of the invention, double screws and/or double cords are advantageously implemented. Here, two separate rows of anchor screws are attached to the vertebra in strategic locations, and (at least) two independently tensioned cords are disposed, tensioned and secured within these two sets of anchor screws accordingly. By having two or more tensioning cords being manipulated independently, the surgeon can accomplish a greater degree of correction, especially de-rotation of the spine, than otherwise possible with a single row of anchor screws and a single tensioning cord. Two independent tensioning cords provide for more tightening range than one tensioning cord and prevents loss of the rotation correction that occurs with single screw/cord constructs. Double screws/double cords are also advantageous in addressing a double curve of the spine, where the vertebrae forms a double scoliosis curve.

Figure 1A:
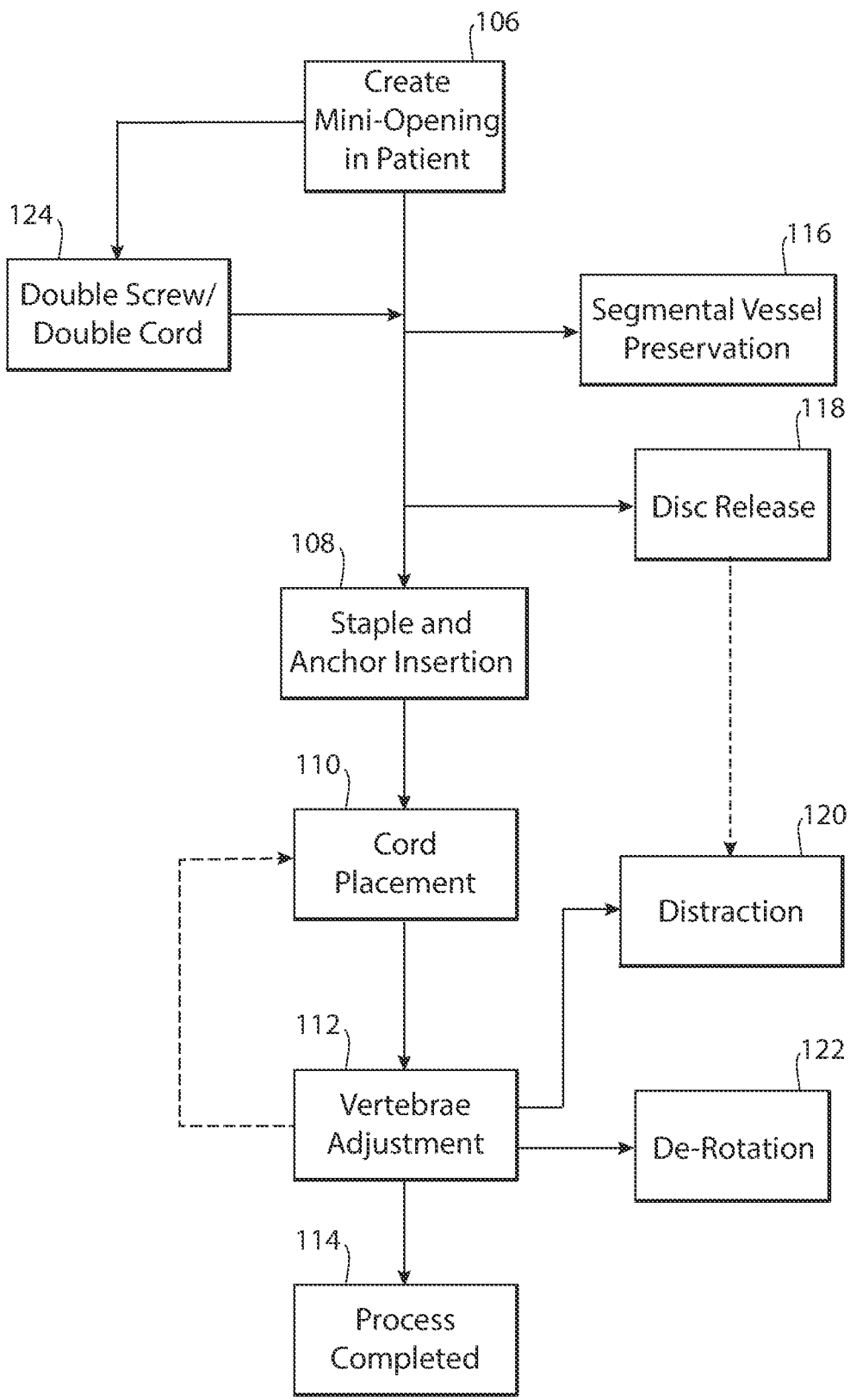
FIG. 1A is a flowchart showing the main steps that may be applied to any or all of the three major aspects/methodologies of the present invention.

This specification is provided with reference to components bearing identifying indicia as follows:
300 patient
302 area of procedure
304 C-arm head
306 Steinmann pin
308 line marking 310 darkened line
312 scalpel
314 retractor
316 muscle
318 mini-opening
322 anchor screw
322*a* first anchor screw
322*b* second anchor screw
322*c* posterior anchor screw
322*d* anterior anchor screw
322*e* single anchor screw
322*f* upper posterior anchor screws
322*g* upper anterior anchor screws
322*h* lower posterior anchor screws
322*i* lower anterior anchor screws
322*j* upper neutral posterior anchor screw
322*k* lower neutral posterior anchor screw
322*l* upper neutral anterior anchor screw
322*m* lower neutral anterior anchor screw
324 staple
326 vessel
328 hemostat
330 portal
332 disc
334 annulus
338 tensioning cord
338*a* posterior tensioning cord
338*b* anterior tensioning cord
338*c* upper posterior tensioning cord
338*d* upper anterior tensioning cord
338*e* upper bridge posterior tensioning cord
338*f* lower posterior tensioning cord
338*g* lower anterior tensioning cord
338*h* lower bridge posterior tensioning cord
338*i* posterior crossover tensioning cord
338*j* anterior crossover tensioning cord
338*k* upper bridge anterior tensioning cord
338*l* lower bridge anterior tensioning cord
338*m* auxiliary posterior tensioning cord
338*n* auxiliary anterior tensioning cord
339 auxiliary tensioning cord
340 stationary tower
342 de-rotation tower
346 counterforce vector
348 de-rotation force vector
350 translational force vector
352 screwdriver
354 paddle
356 unreleased disc
358 distractor
360 posterior row of anchor screws
362 anterior row of anchor screws
364 upper curve
366 upper set of vertebrae
368 lower curve
370 lower set of vertebrae
372 neutral vertebra
374 upper posterior row
376 upper anterior row
378 lower posterior row
380 lower anterior row
382 approximate vertical center line
384 approximate horizontal center line Overall Process Flow FIG. 1A is a flowchart showing the three major aspects/methodologies of the invention as described herein; i.e. disc release 100, de-rotation of the spine 102, and the use of double screws/double cords 104. Depending on the type and severity of the scoliosis, the surgeon may implement any or all of the aspects of the invention.

Referring the general flowchart of FIG. 1A, for all of the procedures described herein, a vertical mini-opening is created at step 106 by the surgeon in the side of the patient to enable the surgeon to access the vertebrae. In accordance with a first major aspect of the invention, a disc release procedure 118 may be performed on discs located between pairs of adjacent vertebrae to enable the pairs of adjacent vertebrae to be adjusted, by incising the disc near its center to allow additional movement of the adjacent vertebrae during the operation. By releasing the discs in step 118, an optional distraction procedure 120 may also be performed on at least one pair of adjacent vertebrae of the spine of the patient by inserting a paddle in a previously released disc between two vertebrae adjacent the vertebrae to be compressed and rotating the paddle in order to urge the adjacent vertebrae together. Further optionally, a segmental vessel preservation procedure 116 may be performed as will be described in further detail below. It is noted that the disc release procedure 118 may be performed before or after the segmental vessel preservation procedure 116.

Next, staples and corresponding anchor screws are inserted into the vertebrae to be adjusted at step 108. As known in the art, each anchor screw has a channel suitable for accepting a tensioning cord, which will be used to enable an adjustment procedure on each of the vertebrae by urging and maintaining the anchor screws and corresponding vertebrae in a straight or substantially straight line with each other. At step 110, the tensioning cord is disposed within the channels of one or more of the anchor screws to enable an adjustment procedure on the vertebrae.

At step 112, a vertebrae adjustment procedure is performed in which each of the vertebrae is adjusted with respect to at least one other adjacent vertebra. This may be implemented utilizing a de-rotation procedure 122 in accordance with a second major aspect of the invention. The tensioning cord is tensioned after the vertebrae are de-rotated, then secured within the channel to maintain the de-rotational adjustment. This is repeated until all of the vertebrae have been adjusted as desired.

In certain cases, such as for double scoliosis curves, it may be advantageous to utilize two rows of anchor screws and two (or more) tensioning cords, which is shown at step 124. Many of the procedures set forth for single screw/cord applications above will also be utilized for double screw/double cord applications, modified accordingly and as explained in further detail herein. Once the surgeon has implemented the desired procedures, the process is complete at step 114. The details of these procedures are now described in further detail.

Patient Preparation

Figure 1B:
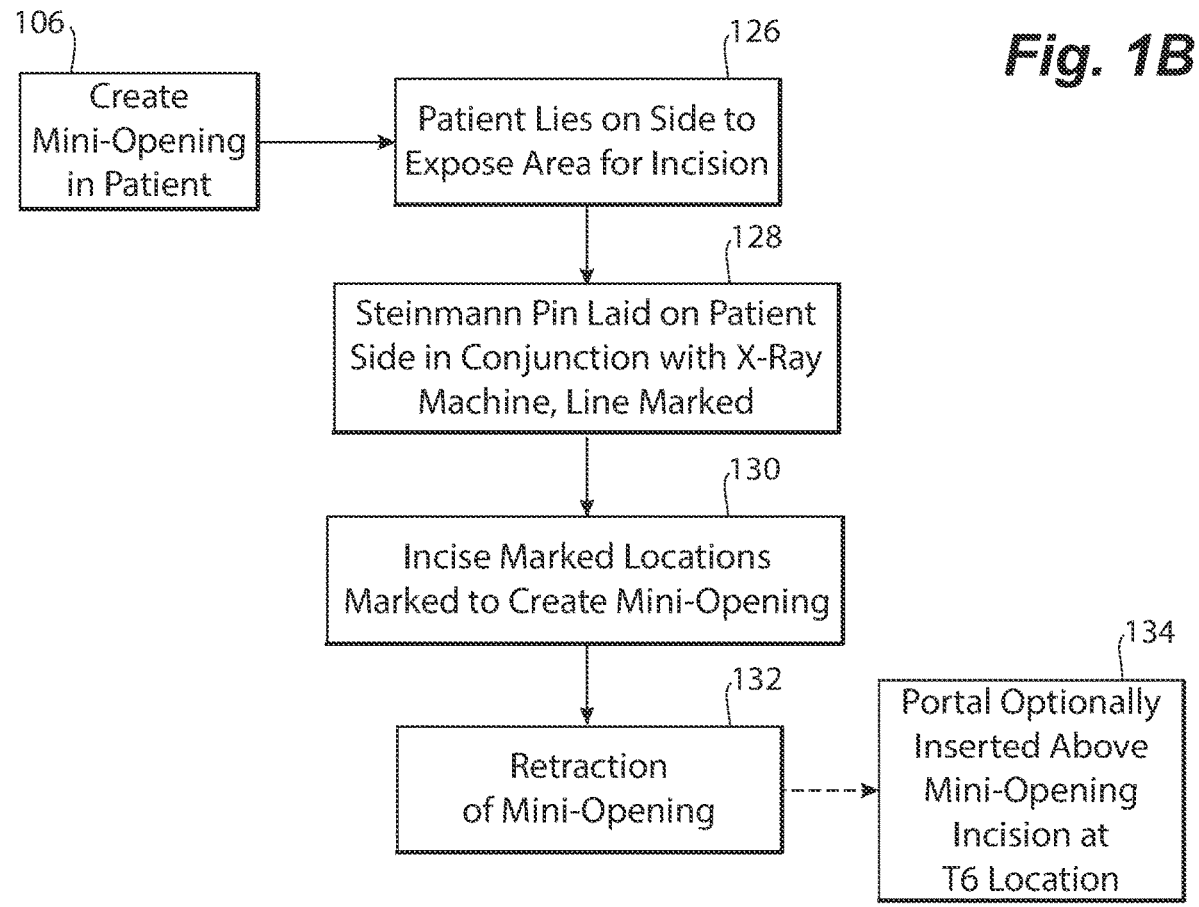
FIG. 1B is a flowchart showing the detailed procedure for creating the mini-opening in the patient.
Figure 2:
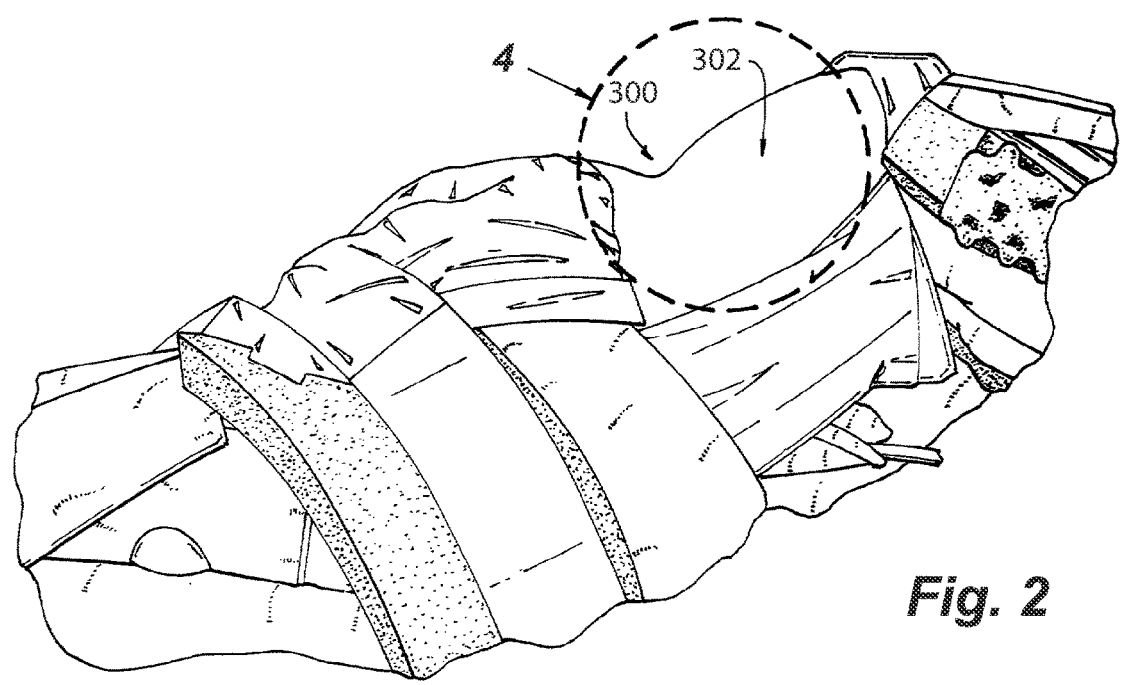
FIG. 2 illustrates a patient lying on her side in preparation for the preferred embodiment anterior scoliosis correction procedure of the present invention.
Figure 3:
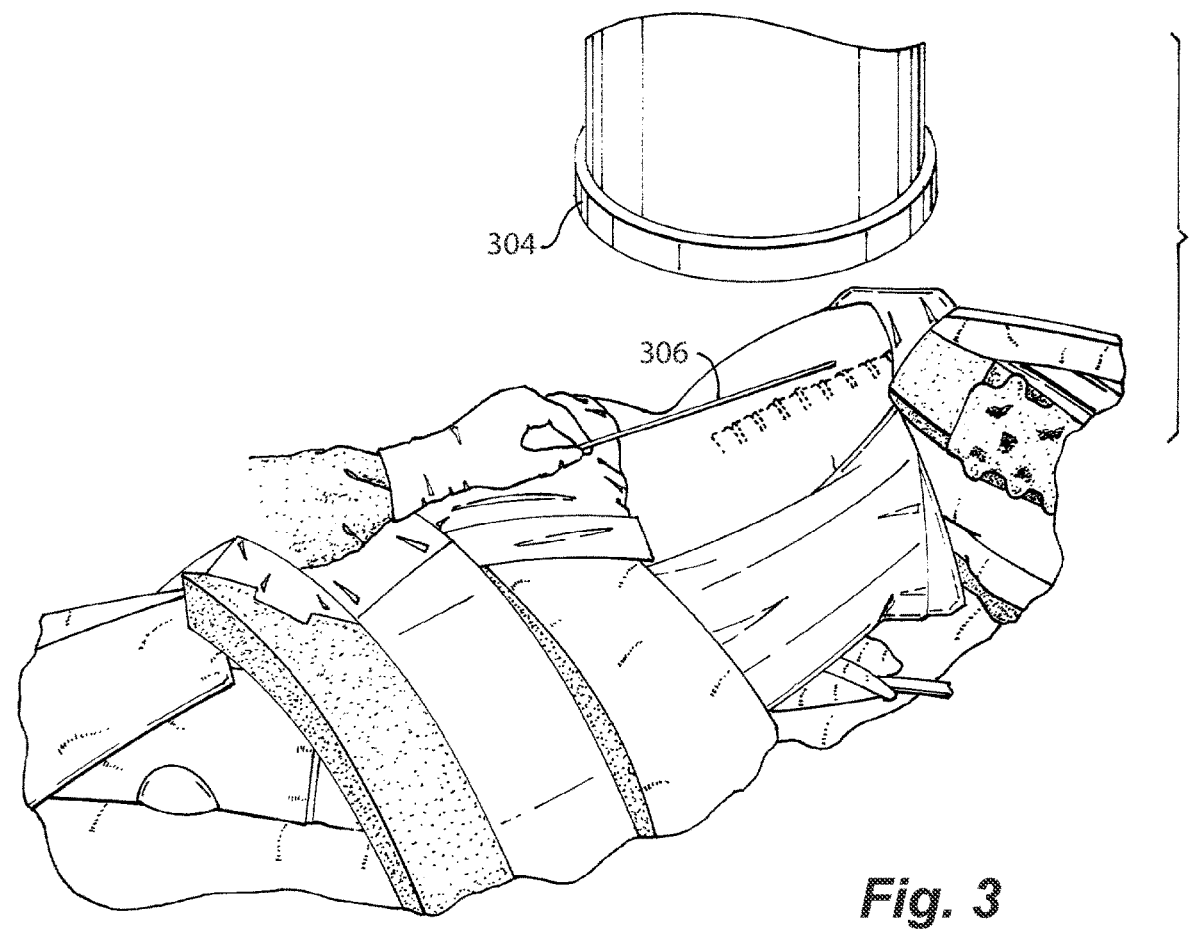
Figure 4:
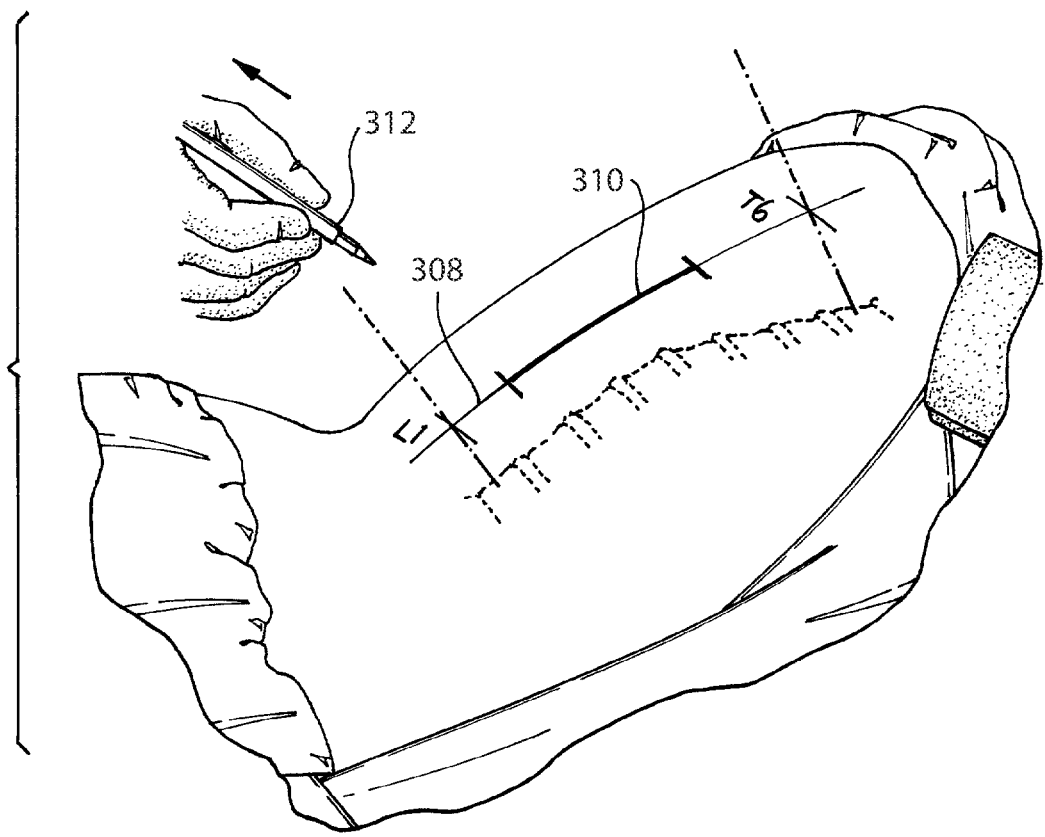
FIG. 4 illustrates the marking of the patient along the lateral vertebral body midline, wherein the darkened area denotes the location of the exact incision.

FIG. 1B is a flowchart showing the detailed procedure for creating the mini-opening in the patient, and accompanying FIG. 2 illustrates a patient 300 lying on her side in preparation for the anterior scoliosis correction procedures of the present invention. With reference to FIG. 2, as part of the pre-operation preparation, at step 126 the patient 300 is placed in a lateral position, laying on their side, with their arm pulled away from and immobilized from the area 302 where the surgeon will perform the procedure. FIG. 3 illustrates the patient of FIG. 2 showing the use at step 128 of a Steinman pin 306 in conjunction with intra-operative x-ray imaging of the lateral spine for determining positioning of the midline of the vertebral bodies being operated on. Using the C-arm head 304 of an x-ray machine (not shown)

as a guide, the pin 306 is centered over the skin of the patient, over the vertebral bodies along the spine where the anchor screws will be inserted (as shown in phantom lines in FIG. 3), and markings are then made on the skin of the patient 300 to delineate the area where the surgeon will incise the mini-opening along the side of the patient, which will be approximately 4-6 inches long, e.g. near the L1 vertebra. FIG. 4 illustrates the resulting marking 308 made by the physician of the patient 300 along the lateral vertebral body midline, wherein the darkened line 310 denotes the location of the exact incision to be made using the scalpel 312.

Figure 5:
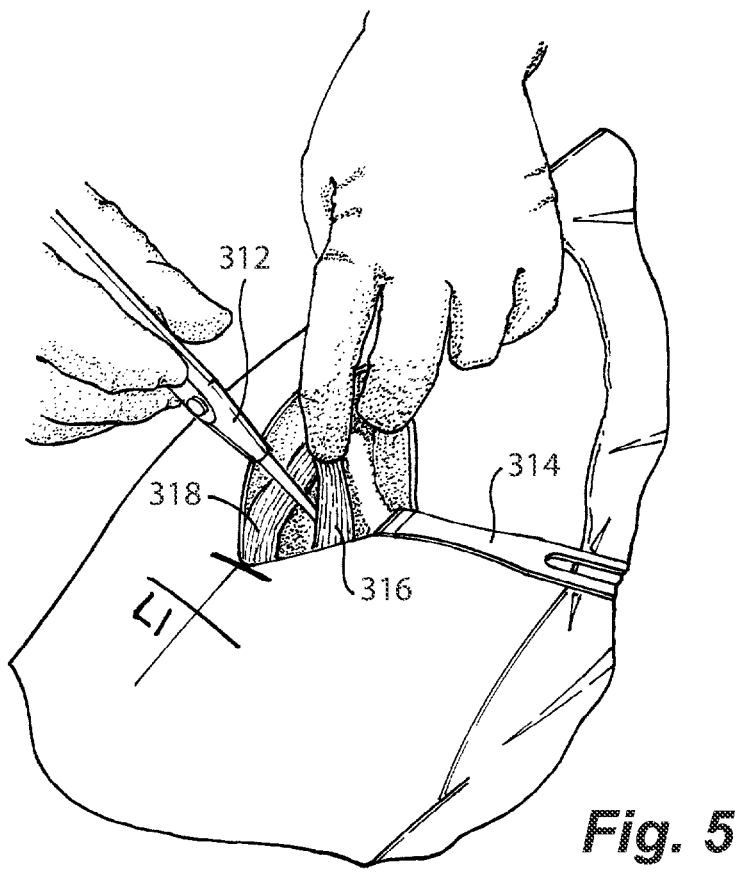
FIG. 5 illustrates a mini-thoracotomy being performed on the patient with a vertical incision through the latissimus dorsi muscle to create a mini-opening, in which the skin and muscle are retracted in anticipation of the surgical procedure.

FIG. 5 illustrates a mini-thoracotomy being performed at step 130 on the patient 300 with a vertical incision through the latissimus dorsi muscle 316 to create a mini-opening 318, in which the skin and muscle are retracted at step 132 using a retractor 314 in anticipation of the surgical procedure. After the surgeon has made the desired incision using the scalpel 312 to create the mini-opening 318 along the patient's side, the latissimus dorsi muscle 316 is visible. The lung will be deflated at this point, thus providing an essentially empty cavity. The rib cage, vertebrae and discs will then be visible to the surgeon. Optionally, at step 134 a thorascopic portal 330 may be inserted at approximately the T6 location (see e.g. FIG. 8) and/or the L1 location. In order to gain access to the vertebrae that are not exposed directly through the mini-opening incision, the surgeon will undermine the uncut skin by cutting a plane in the tissue under the skin in order to stretch the incision from below. That is, by cutting the plane under the skin adjacent to the mini-opening, the surgeon can lift up the skin since the muscle has been dissected, and then for example make a puncture and insert the portal 330 at the T6 (and/or L1) interspace as shown without making a separate incision (or without extending the mini-opening incision longer than necessary). It is noted that in the prior art, the physician usually incises the patient horizontally (straight across), which kills the distal end of the muscle, whereas in the present invention the incision is made vertically as shown in order to, inter alia, spare the muscle.

Segmental Vessel Preservation

Figure 1C:
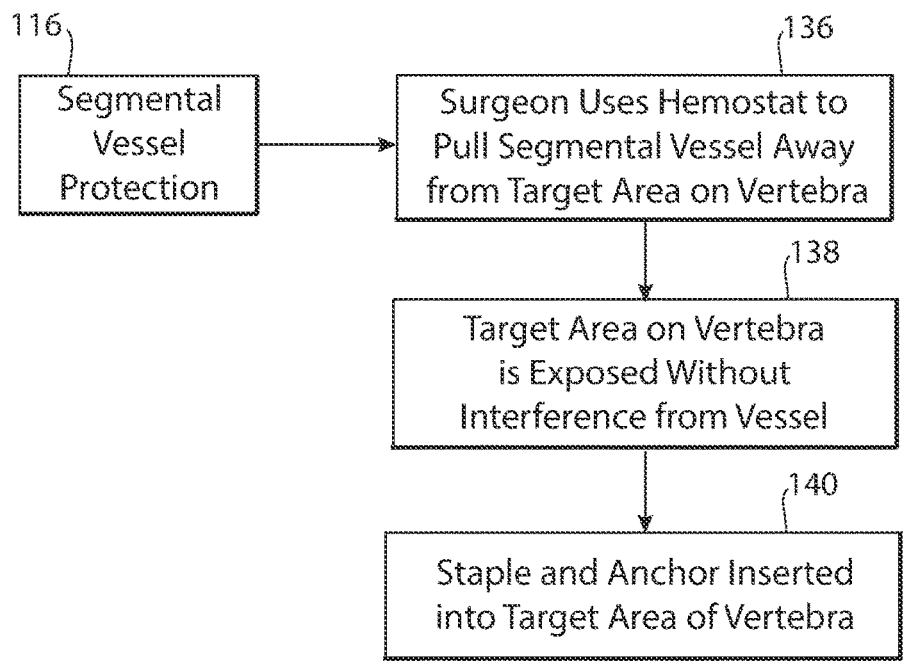
FIG. 1C is a flowchart showing the detailed procedure of the segmental vessel preservation procedure.

Reference is now made to FIG. 1C, which is a flowchart showing the sub-steps of the optional segmental vessel preservation procedure 116 of FIG. 1A in further detail. In addition, FIG. 7 illustrates the surgeon performing the segmental vessel preservation procedure using a right-angle hemostat 328 (or another surgical instrument that may be appropriate). In the prior art, segmental vessels (i.e. those vessels that go from the aorta across the vertebral body into the paranum) are sacrificed when the anchor screws are inserted into the vertebra. See, for example, the '736 patent. In the present invention, however, the segmental vessels may be preserved by the surgeon, as follows. At step 136, the segmental vessel 326 may be preserved by retracting it from the target area on the vertebra by manipulating the hemostat 328, exposing the side of the vertebra at step 138, enabling insertion of the staple 324 and anchor screw 322 into the desired target area of the vertebra at step 140. The surgeon then inserts a staple 324 into the side of the bone (vertebra), and the anchor screw 322 may then be inserted into the bone via the staple 324 as known in the art (see also FIG. 6). The staple 324 provides a stable anchoring point to ease the insertion of the anchor screw 322. It is noted that the segmental vessels may only be preserved by this procedure in the vertebral bodies that are exposed to the surgeon through the mini-opening.

Figure 6:
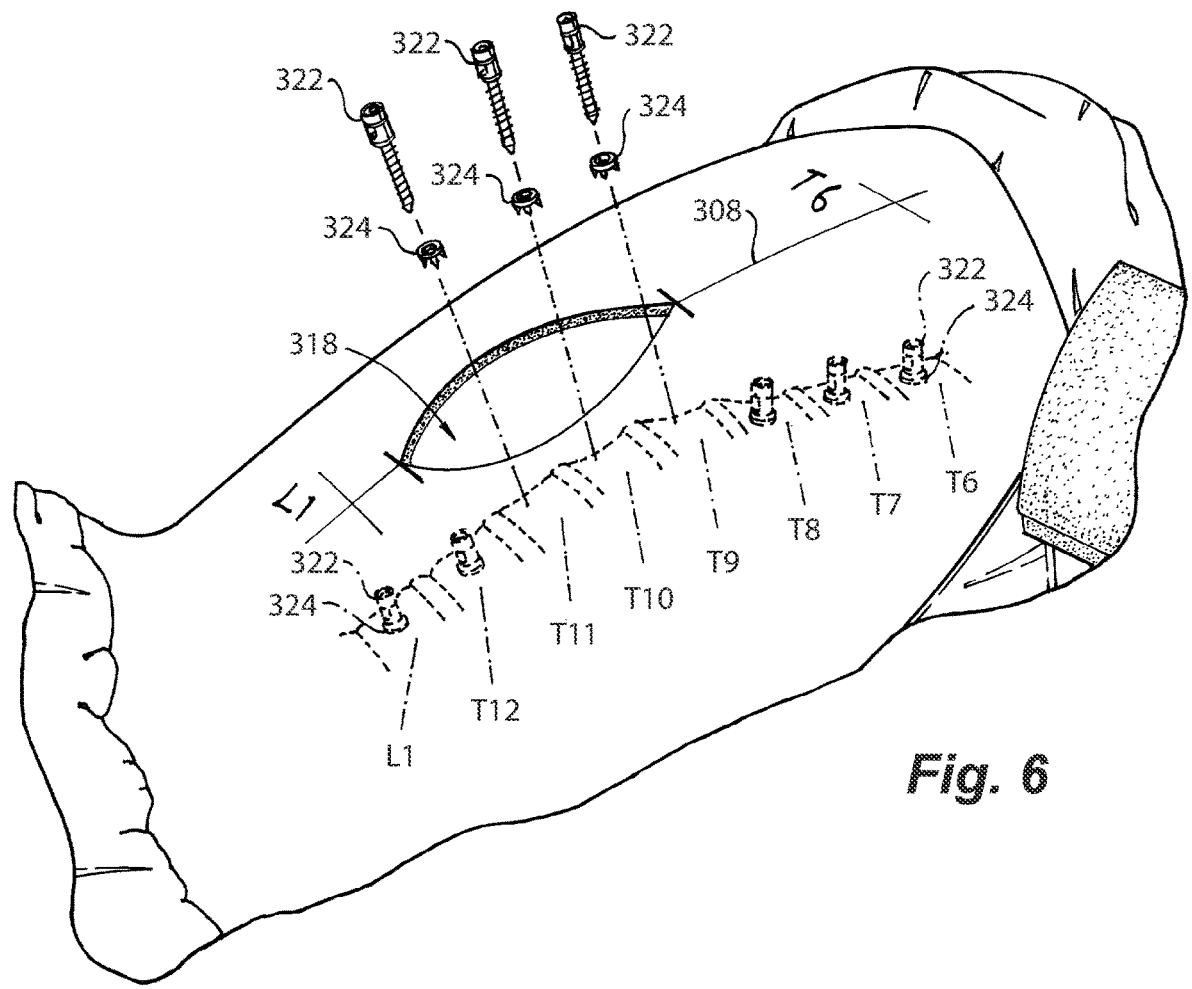
FIG. 6 illustrates the typical placement of the anchor screws and staples/washers along each vertebral body through the mini opening in the procedure.
Figure 7:
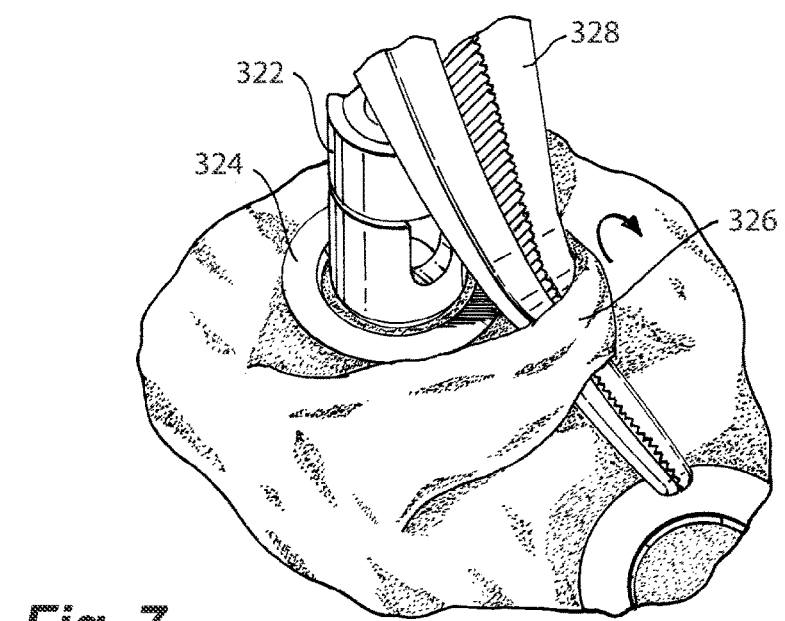
FIG. 7 illustrates the surgeon performing a segmental vessel preservation procedure using a right-angle hemostat.

FIG. 6 illustrates the typical placement of the anchor screws 322 and staples/washers 324 laterally along the side of each vertebral body T6, T7, T8, T9, T10, T11, T12 and L1 through the mini opening 318 in the procedure, performed optionally in conjunction with the segmental vessel preservation procedure described above. In FIG. 6, the ribs of the patient, which have been spread to give better access by the surgeon to the vertebra, are not shown for sake of clarity.

Using the prior art VBT techniques, usually only one staple 324 is placed onto the vertebra. The surgeon can place the two prongs of the staple 324 close to the end plate, a single prong close to the segmental vessel 326, and then the staple 324 may be malleted into the vertebra. In general, the surgeon has much more flexibility for the angle of placement of the staples 324 in a vertebral body using the mini-open vertical incision of the present invention, as opposed to the prior art portal access method alone.

Disc Release

As referenced above, a first major inventive aspect of the present invention is to release the ligaments as may be required and thus loosen the spine, which provides for optimal correction of the patient's scoliosis. With many occurrences of scoliosis, on the inside of every curve are ligaments and the disc annulus (i.e., soft tissue) that contracts and cannot stretch out enough to allow for straightening of the spine. Rotational correction is advantageously attained with release of these soft tissues. A unique aspect of this disc release correction technique is using the now released disc space to assist with correction while the surgeon is tightening the tensioning cord. The surgeon can place an instrument called a disc space trial and help move the vertebra proxillaly, reducing the risk of the anchor screw plowing in the vertebra.

Figure 8:
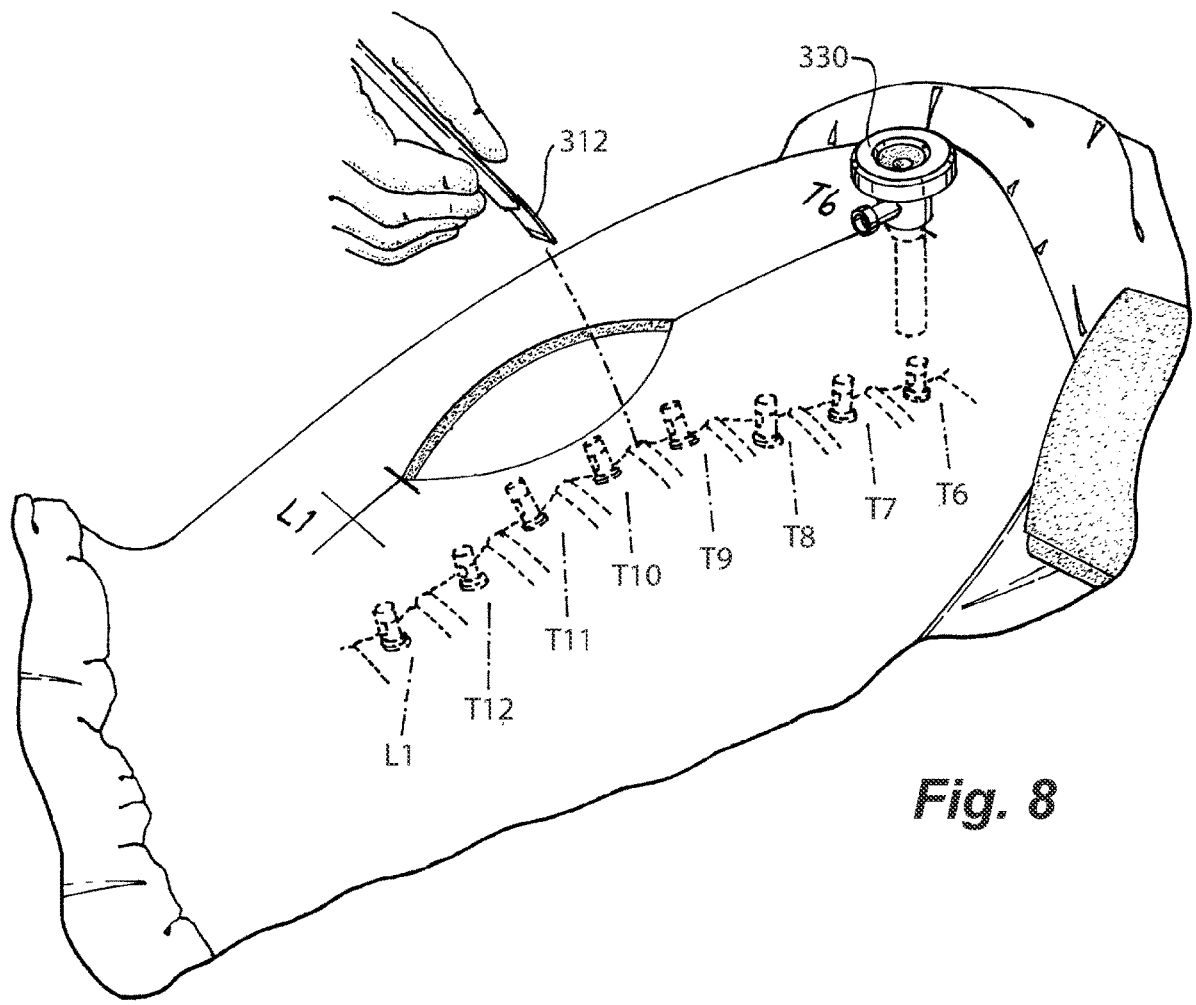
FIG. 8 illustrates a surgeon approaching the mini opening with a scalpel in anticipation of performing a disc release procedure.
Figure 9:
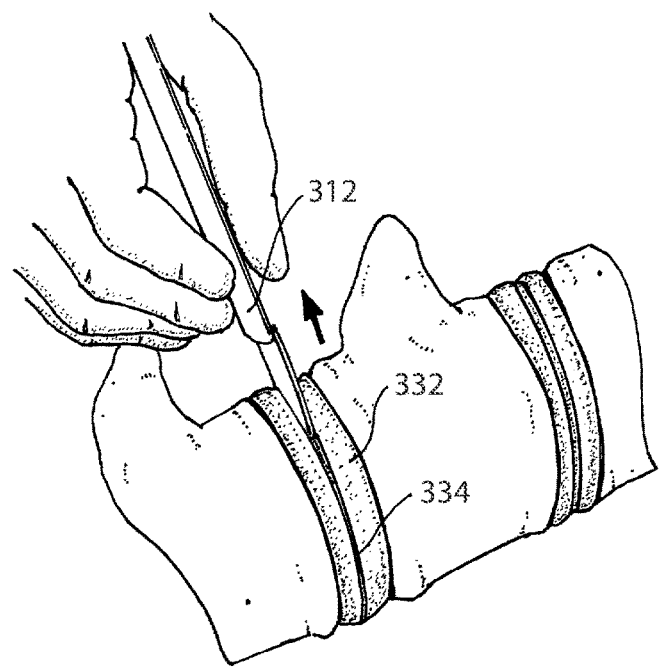
FIG. 9 illustrates the surgeon performing the disc release procedure.

FIG. 8 shows a diagrammatical perspective view of the complete installation of staples/washers 324 and corresponding anchor screws 322 with the surgeon approaching the mini-open 318 with a scalpel 312 in anticipation of releasing the discs, and FIG. 9 illustrates the surgeon performing the disc release procedure. In FIG. 8, all of the screws and washers have now been inserted into the vertebral bodies T6, T7, T8, T9, T10, T11, T12 and L1.

With reference to FIG. 9, another advantage provided by the techniques of the present invention as described herein is the ability for the surgeon to release the disc 332 by incising the disc, releasing the eccentric nucleus, and incising the annulus 334 including the anterior longitudinal ligament circumferentially. The surgeon can access the entire disc area and use leverage because of the mini-open access that is otherwise unobtainable via prior art portals.

Notably, the disc release can decompress an eccentric fixed nucleus proposus that prevents recreation of kyphosis during the rotation maneuver. This indirectly allows shortening of the column of the spine and removes the force vectors of the spine trying to rotate back to scoliosis (referred to as de-torqueing the spine deformity)

It is noted that in some cases the discs must be released first if the curve of the spine is so severe, in order to straighten out the spine and make insertion of the screws and staples easier. In these cases, the disc release procedure is performed prior to insertion of the anchor screws, rather than afterwards as shown in the above example. In some cases, the surgeon may not be sure if the patient will require release of the discs, so the anchor screws would be inserted first and if the spine is too stiff then the disc release may be performed later on.

Cord Placement

Figure 10A:
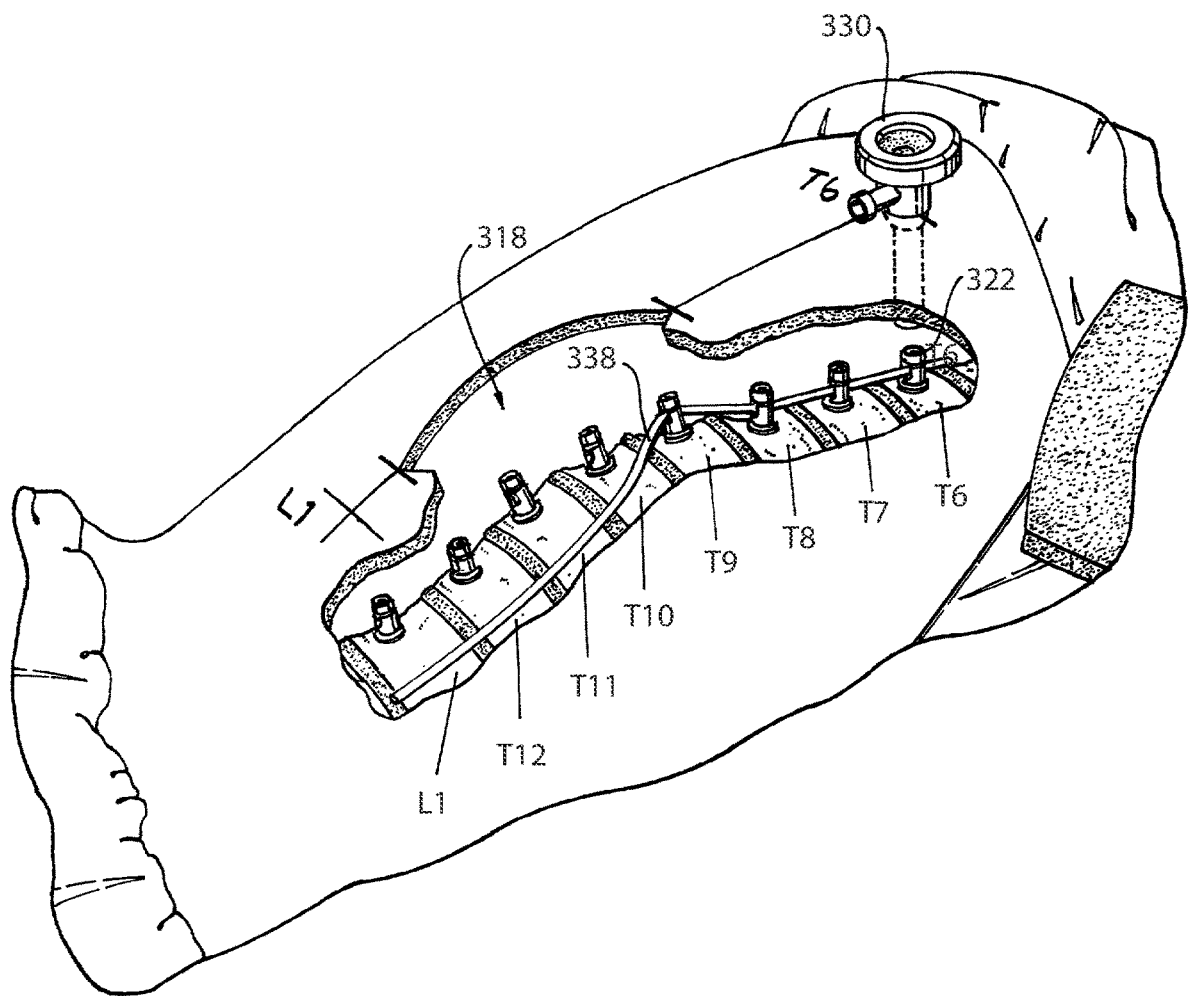
FIG. 10A illustrates the placement of the cord within the channels of some of the anchor screws along the vertebral bodies in a preferred embodiment.
Figure 10B:
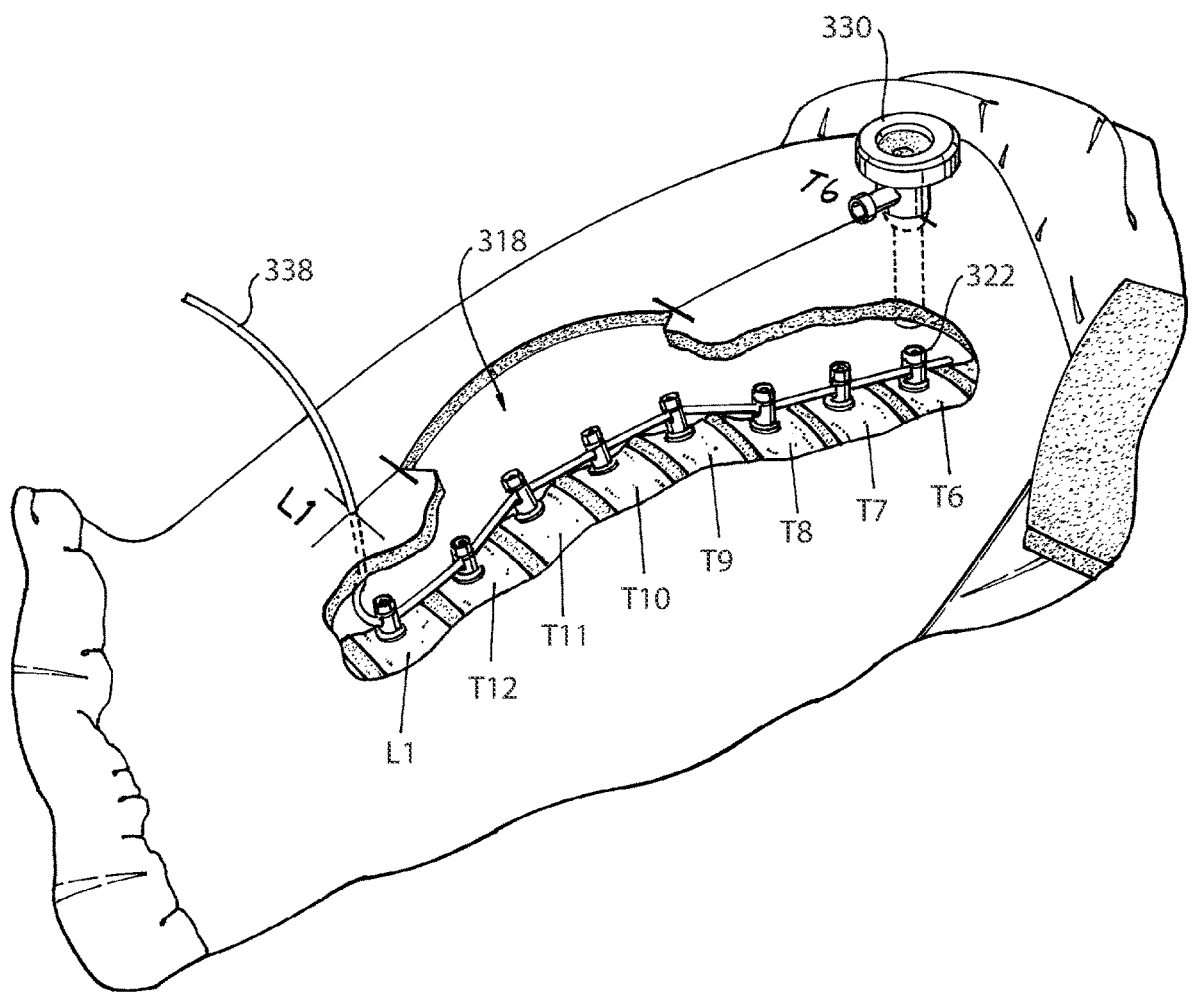
FIG. 10B illustrates the initial placement of the cord within the channels of all of the anchor screws along the vertebral bodies in an alternate embodiment.

Once the anchor screws 322 have all been attached to the patient's vertebra T6, T7, T8, T9, T10, T11, T12 and L1 through the mini opening 318 as described above, the next step is to place a tether or tensioning cord 338 (e.g. a white polyethylene-terephthalate flexible cord as known in the art, see FIG. 10A) within a corresponding channel of the anchor screws 322 at step 110 of FIG. 1A in order to provide tension at desired locations along the spine and maintain the correction. First, the cord 338 is inserted in the anchor screw 322 at T6 and secured (tightened to the anchor screw) to form an initial reference point. Then the cord 338 is placed through the channel of the anchor screw 322 on the next adjacent vertebra (T7) so that T7 may be corrected (de-rotated) with respect to T6 as will be described below. This process continues down the spine, one vertebra at a time, until all the vertebrae have been corrected. Note that in FIG. 10A, the cord is shown disposed through the anchor screw at T6, T7, T8, and T9 since these vertebrae have already been corrected, and T10, T11, T12 and L1 are awaiting correction. (In an alternative embodiment, the tensioning cord 338 may be disposed initially through the channels of all of the anchor screws as shown in FIG. 10B, prior to correcting any of the vertebrae). If a portal is (optionally) located at L1, then the cord will exit the body of the patient through that portal (not shown). By using the access provided by the mini-open procedures, the surgeon is able to use correction maneuvers such as translation, compression, and enhanced de-rotation, as explained in further detail below, and then the spine correction is held by tensioning and securing of the cord 338 between the anchor screws 322.

De-Rotation

Figure 1D:
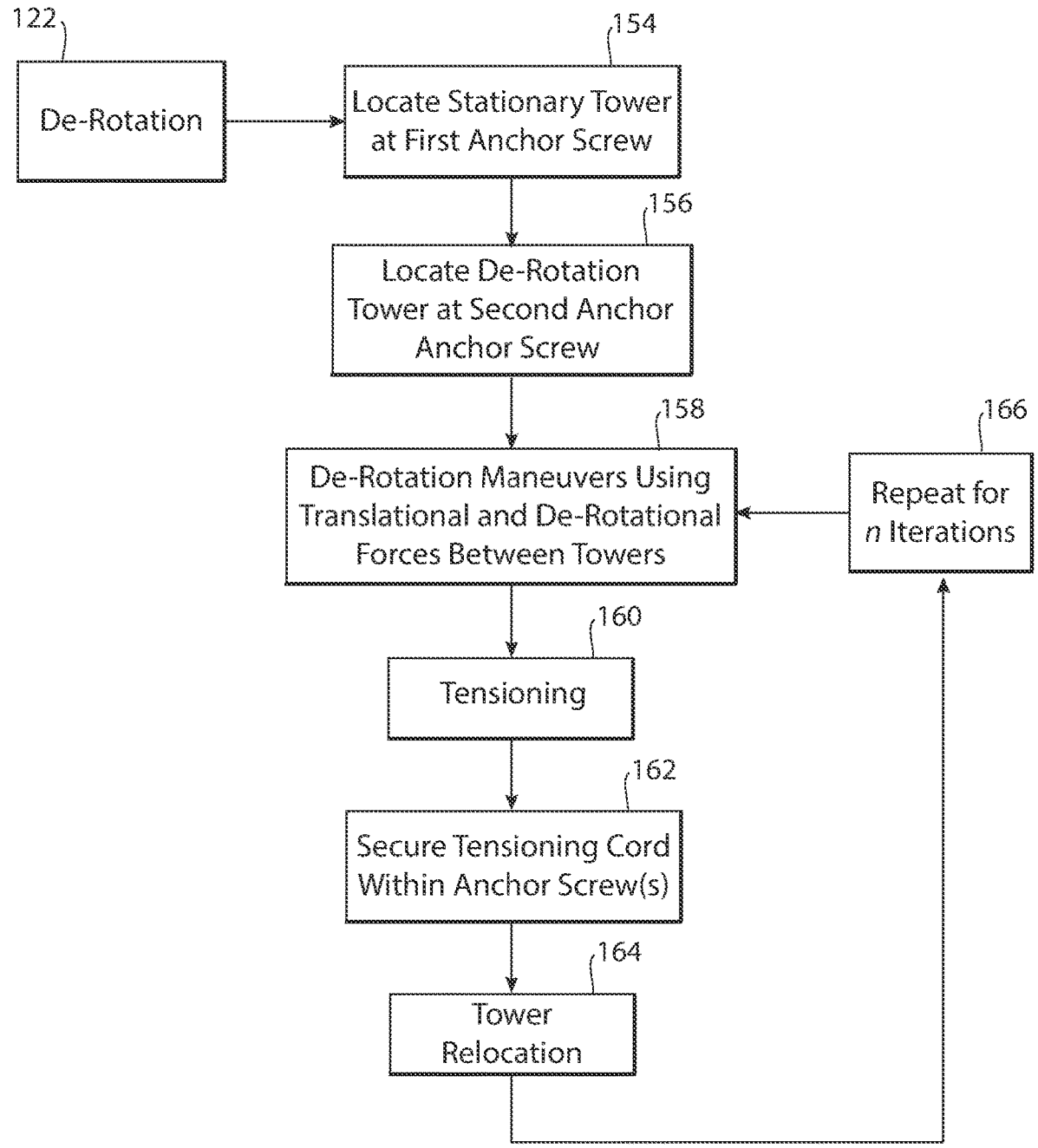
FIG. 1D is a flowchart showing the main steps of a preferred embodiment of the second aspect of the anterior scoliosis correction procedure of the present invention showing the vertebrae de-rotation procedure.

The preferred embodiment of the vertebrae adjustment procedure 112 is the de-rotation procedure 122, which forms a second major aspect of the present invention, and which is now explained in detail with respect to FIG. 1D. A detailed example of de-rotation of the T9 vertebra with respect to the spine, in particular with respect to T6, will be described. In practice, the surgeon will have performed the same de-rotation procedure first on vertebra T7 with respect to T6, and then on T8 with respect to T6. The de-rotation of vertebra T9 with respect to T6 has been chosen for the detailed discussion since the juxtaposition of these two vertebrae lends itself to greater clarity of explanation. After T9 has been de-rotated, then the procedure continues as may be required for T10, T11, etc.

It is further noted that portals may be used at T6 and L1 because they remain essentially stationary against which the rotation is performed through the mini-opening, and thus the mini-opening is not required all the way from T6 to L1. This is generally preferred since it is beneficial to not incise the patient along the mini-opening any more than necessary in order to accomplish the techniques of this invention.

Tower Placement

Figure 11A:
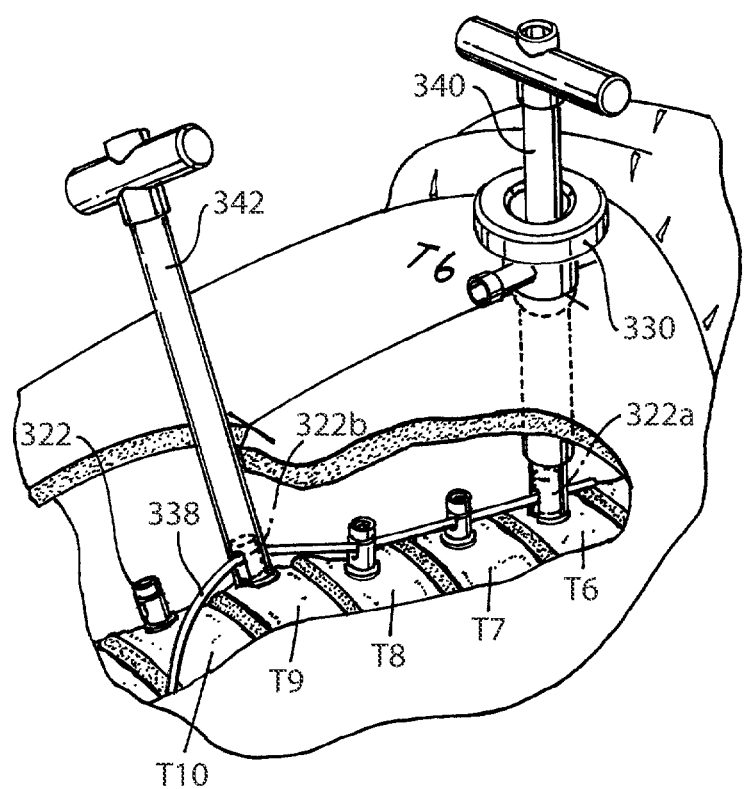
FIG. 11A illustrates the initial offset setup locations of the stationary tower and the de-rotation tower from the anterior perspective along the axis of the spine, prior to performing the de-rotation procedure.
Figure 11B:
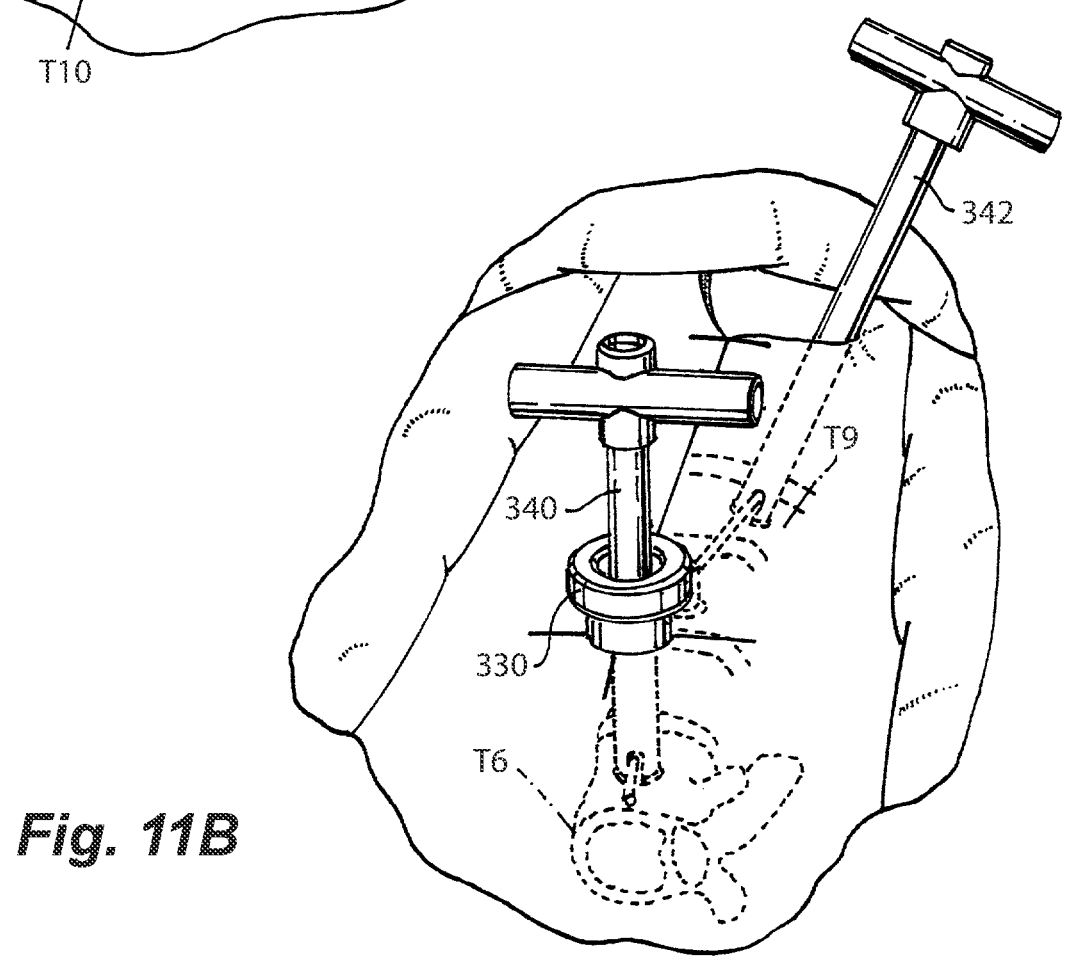
FIG. 11B illustrates the initial offset setup locations of the stationary tower and the de-rotation tower of FIG. 11A but from the cranial perspective, prior to performing the de-rotation procedure.

FIGS. 11A and 11B both illustrate the initial offset locations of a first tower, referred to as a stationary tower 340, and a second tower, referred to as a de-rotation tower 342, along the spine. As shown, the stationary tower 340 is mated with a proximal or first anchor screw 322a located on a first vertebra (T6, via the portal 330) at step 154 of FIG. 1D. The de-rotation tower 342 is mated with a distal or second anchor screw 322b on a second vertebra T9 at step 156 of FIG. 1D. In particular, FIG. 11A illustrates the initial offset setup locations of the stationary tower 340 and the de-rotation tower 342 from the anterior perspective along the axis of the spine, prior to performing the de-rotation procedure, and FIG. 11B illustrates the initial offset setup locations of the stationary tower 340 and the de-rotation tower 342 of FIG. 11A but from the cranial perspective, prior to performing the de-rotation procedure. As shown, the stationary tower 340 is disposed substantially vertically, generally perpendicular to the patient 300. The de-rotation tower 342 is disposed at an approximately 45-degree angle with respect to the vertically aligned stationary tower 340. As previously described, an optional portal 330 is inserted as shown over the T6 vertebra, through which the stationary tower 340 may be inserted and adjoined with the first anchor screw 322a on the T6 vertebra. By using a portal 330 to hold the stationary tower at T6, the length of the mini-open incision may be kept as small as possible while still providing the advantages of the present invention. The portal 330 is a viable option since it is not necessary for the surgeon to be able to see directly the T6 vertebra while performing the de-rotation procedure, and since the stationary tower 340 will remain substantially stationary during de-rotation as will be described.

If the surgeon does not have direct access to place the tower 342 on the anchor screw head from the thoracotomy opening, then a small puncture is made through the intercostal space for example going through the intercostal space of T7-T8 to get to the T7 anchor screw and/or the T8 anchor screw. A separate incision is not made; rather, the skin is lifted and then punctured through the intercostal muscle.

As shown in FIG. 11A, the tensioning cord 338 has already been disposed, tensioned and secured in the channels of the anchor screws 322 at T6, T7, and T8 which have already been de-rotated in this example. The tensioning cord 338 is then disposed in the channel of the second anchor screw 322b, ready for de-rotation of T9, tensioning and securing as now described.

De-Rotation Maneuvers

Figure 12A:
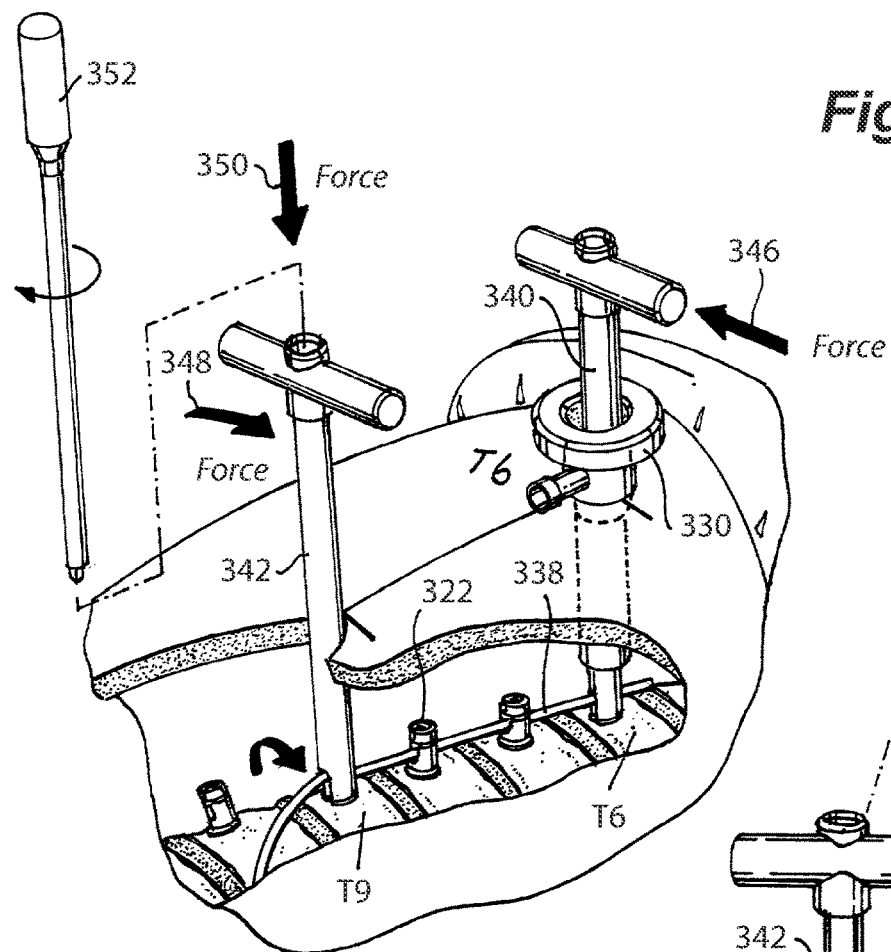
FIG. 12A illustrates the performance of the de-rotation procedure from the anterior perspective along the axis of the spine.
Figure 12B:
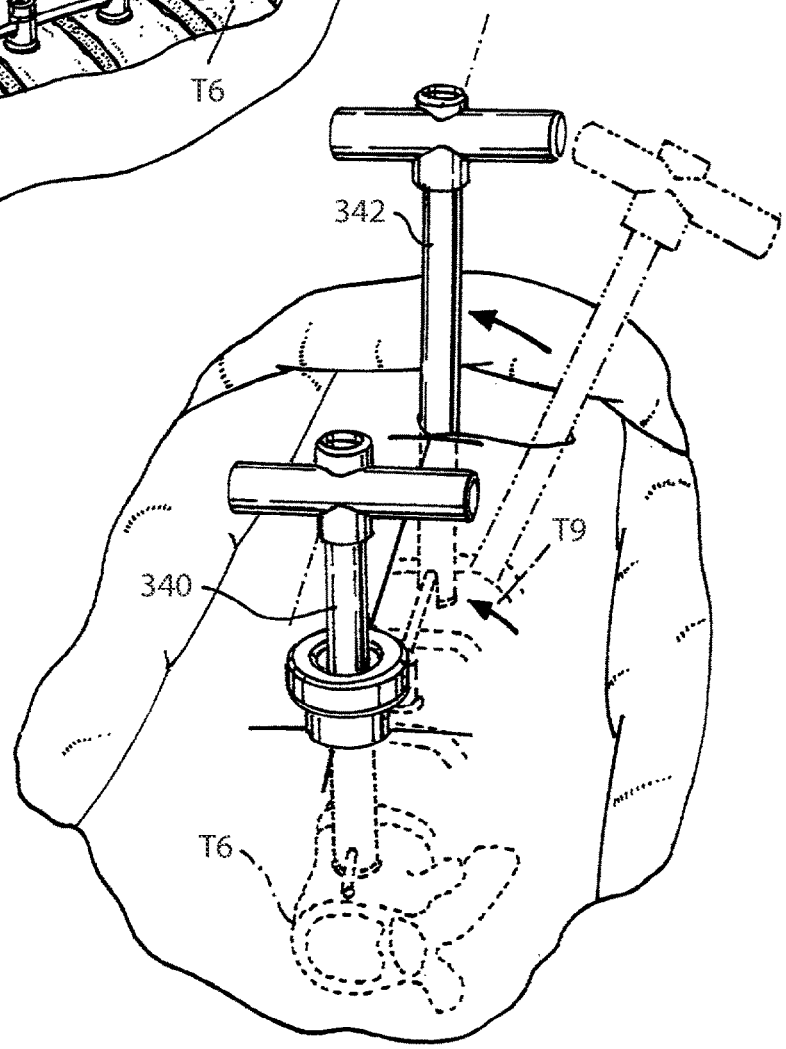
FIG. 12B illustrates the performance of the de-rotation procedure of FIG. 12A but from the cranial perspective.

FIG. 12A illustrates the performance of the de-rotation maneuvers from the anterior perspective along the axis of the spine, and FIG. 12B illustrates the performance of the de-rotation maneuvers of FIG. 12A but from the cranial perspective. De-rotation of the spine is the critical correction force to correct the scoliosis deformity maximally or as much as desired. To achieve this correction result, the following steps are performed with additional reference to FIG. 1D.

The surgeon will be standing on the posterior side of the patient, the head is closest to the viewer. The de-rotation tower 342 will be translated towards the table as explained below, pushing the spine towards a corrected position. Essentially, the stationary tower 340 is the stabilizing force and the de-rotation tower 342 is used to de-rotate the spine.

Thus, at step 158, the surgeon imparts a downwards translational force vector 350 by pressing down on the de-rotation tower 342. The surgeon then executes the de-rotation maneuver with the de-rotation tower 342 by pushing the de-rotation tower 342 laterally along the de-rotation force vector 348, while simultaneously applying a lateral counterforce vector 346 to the stationary tower in opposition to the lateral de-rotation force vector being 348 applied to the de-rotation tower.

That is, the rotation uses the stationary tower 340 at T6 for a counterforce with the de-rotation tower 342 on T9 being pushed anteriorly away from the surgeon affecting a de-rotation maneuver of the vertebrae. Simultaneously, the surgeon is translating by pushing the vertebrae towards the table.

This de-rotation maneuver is sometimes held in place for several minutes, and then additional (same) correction forces vectors, 346, 348 and/or 350 may be applied again as determined by the surgeon to be needed. This is also referred to as stress relaxation of the soft tissue.

Figure 13A:
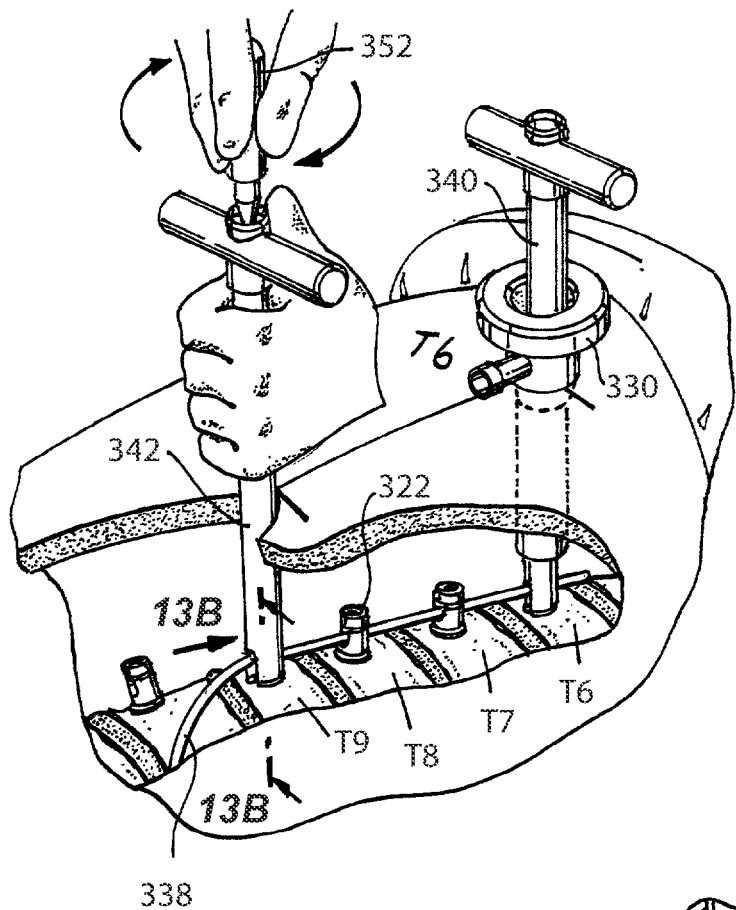
FIG. 13A illustrates a surgeon performing the cord tensioning/securing step.
Figure 13B:
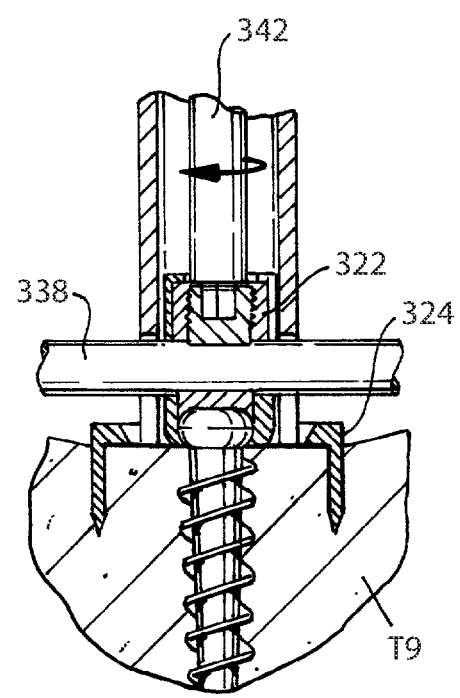
FIG. 13B illustrates the tensioning/securing of FIG. 13A in side elevation cross-section at the anchor device.

FIG. 13A illustrates a surgeon performing a cord tensioning/securing step, and FIG. 13B illustrates the cord tensioning/securing of FIG. 13A in side elevation cross-section at the anchor screw 322. Once the desired correction of the vertebra under de-rotation is obtained, then compression (also referred to as tensioning) is applied by a surgical assistant between the two anchor screws at T8 (which was previously secured) and T9 so the tensioning cord 338 is tensioned at step 160, and the cord is secured to the second anchor screw 322b on T9 with the locking set screw of the second anchor screw 322b tightened at step 162 by a screwdriver (or other screwdriver-type device) 352 inserted into the upper portion of the de-rotation tower 342. It is noted that the screwdriver 352 may be engaged with the tower 342 before the de-rotation maneuvers are executed, if desired.

The cord tensioning step 160 is important since it maintains the de-rotational translation and juxtaposition between the vertebra being maneuvered by the surgeon. It is noted that this is a step known in the art of this type of procedure, such as shown in the '736 patent referred to above and thus need not be repeated in detail.

After the cord has been tensioned and secured in the second anchor screw 322b at T9, thus completing the de-rotation of T9, at step 164 the tensioning cord 338 is threaded through and disposed within the channel of the next anchor screw at T10 (unless the cord has been disposed through all the anchor screws initially as in FIG. 10B), and the de-rotation tower 342 is relocated to the anchor screw at T10 as well. This is referred to as segmental correction of each vertebral body in the curvature since they are de-rotated one at a time. The same step 158 of translation and then de-rotation is then performed as above. Once the desired correction of T10 is obtained, then compression is applied on the cord between the next two anchor screws and the locking set screw is once again tightened to engage the cord 338 in the anchor screw in a tensioned manner. As shown by step 166, these steps are repeated as desired, until all of the vertebrae have been de-rotated and the cord secured in each anchor screw.

Figure 14:
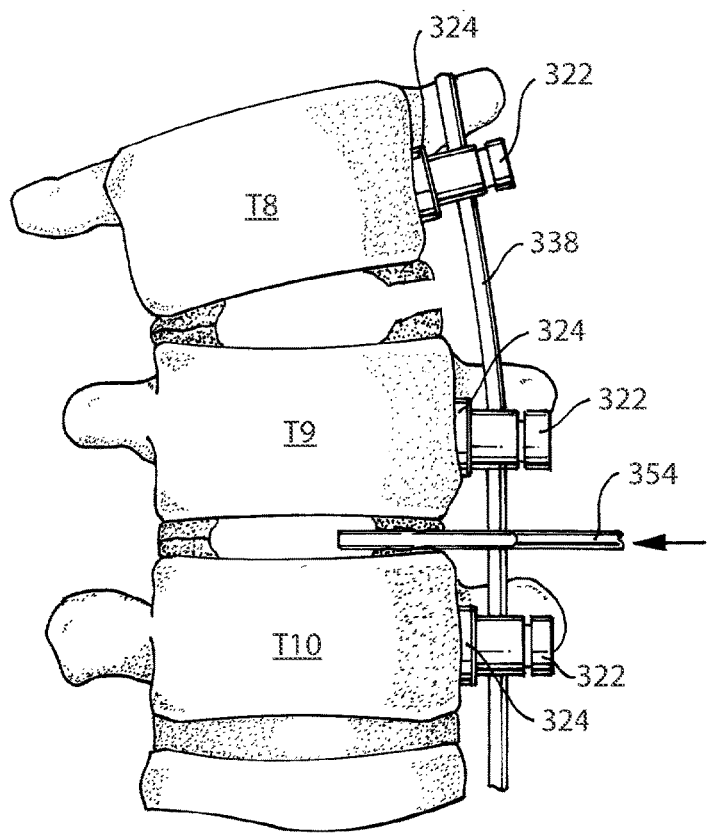
FIG. 14 is an anterior elevation view of a portion of the thoracic spine, with a paddle inserted therein between the T9 and T10 vertebrae.
Figure 15:
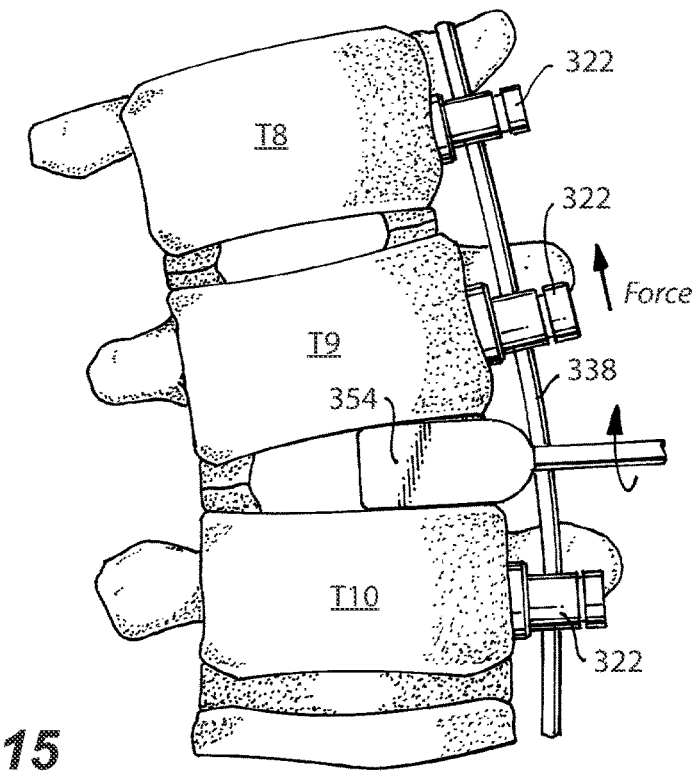
FIG. 15 is the same view as FIG. 14 wherein the paddle is rotated to distract disc space, facilitating the compression of the superior vertebrae.

The stationary tower at T6 will stay located at T6 while the surgeon de-rotates several adjacent vertebrae, e.g. T7, T8, T9. After that, the surgeon will likely move the stationary tower down several vertebrae, e.g. to T9, so that the ensuing de-rotation takes place over only a few vertebrae at a time. So, a typical sequence may be:
 a. Locate stationary tower 340 on T6, locate de-rotation tower 342 on T7
 b. De-rotate T7, tension and secure the cord at T7
 c. Dispose cord within channel of T8, relocate tower 342 to T8
 d. De-rotate T8, tension and secure the cord at T8
 e. Dispose cord within channel of T9, relocate tower 342 to T9
 f. De-rotate T9, tension and secure the cord at T9
 g. Remove tower 342 from T9, relocate stationary tower 340 to T9
 h. Dispose cord within channel of T10, relocate tower 342 to T10
 i. De-rotate T10, tension and secure the cord at T10
 j. Continue process accordingly Distraction Referring now to FIG. 14, there may be occasion with very severe and stiff curves where the disc space between adjacent vertebral bodies remains excessively wedged open, even after the de-rotation procedure. In this case, it is not advisable to simply further tension and tighten the cord, since that may lead to plowing of the anchor screws. In order to address this problem, the prior disc release between these vertebrae is utilized to enable the surgeon to insert a paddle 354 flat in the vacant disc space in the next adjacent disc area and rotate the paddle, which urges the adjacent vertebra together. Thus, in FIG. 14, the disc between T8 and T9 is wedged open, so by placing the paddle 354 in the disc space between T9 and T10 and rotating as in FIG. 15, the T8/T9 disc space is compressed to an acceptable level, and the cord is tightened to maintain the vertebrae together. This distraction technique (step 120 of FIG. 1A) may be done as part of the cord tensioning and securing process when necessary but may only be done when there was a prior disc release to enable insertion of the paddle 354 as shown.

Figure 16:
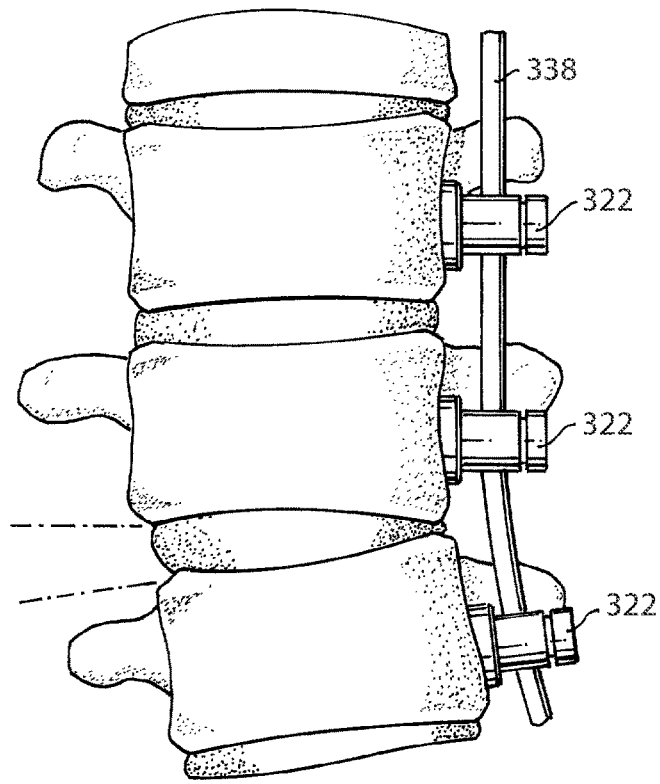
FIG. 16 is an anterior elevation view of a portion of a thoracic spine.
Figure 17:
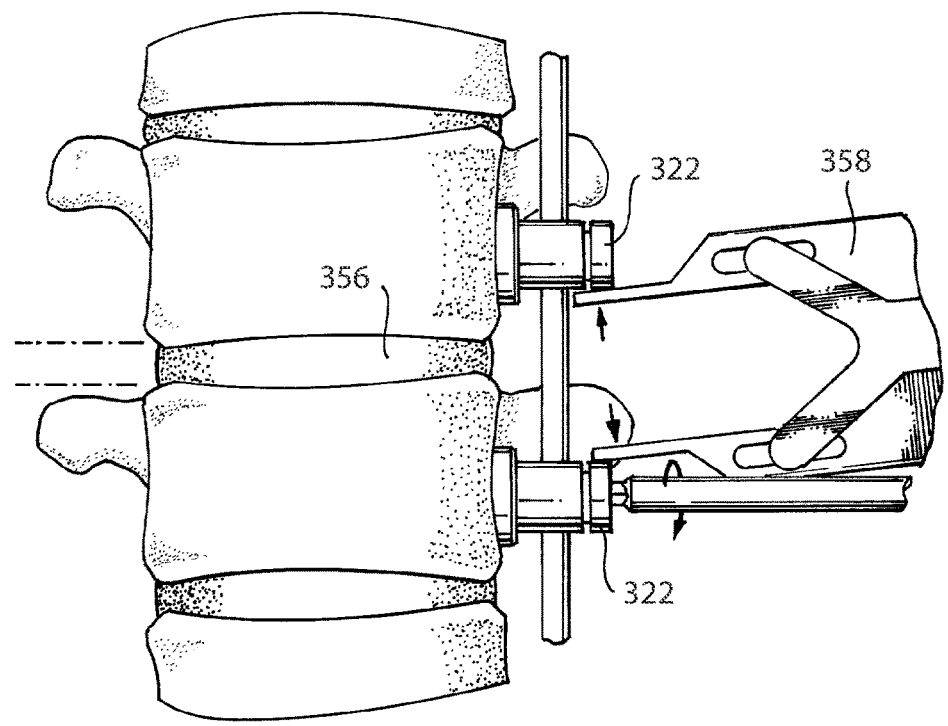
FIG. 17 is the same view as FIG. 16, but showing the use of a distractor to prevent over-correction.

FIG. 16 illustrates a condition where there is an unreleased disc between adjacent vertebrae that is compressed and needs to be decompressed. That is, occasionally at the distal aspect of the deformity, for example T11-T12 or T12-L1, the curve is very flexible, and it is easy to inadvertently overcorrect that segment with reverse wedging of the disc. In this scenario it is recommend using a distractor (spreader) 358 through the incision to parallel the discs before tightening the set screws. The surgeon utilizes the distractor 358 as shown in FIG. 17 between the screws of the adjacent vertebrae to urge them away from each other un-decompress the disc 356 as desired.

Figure 18:
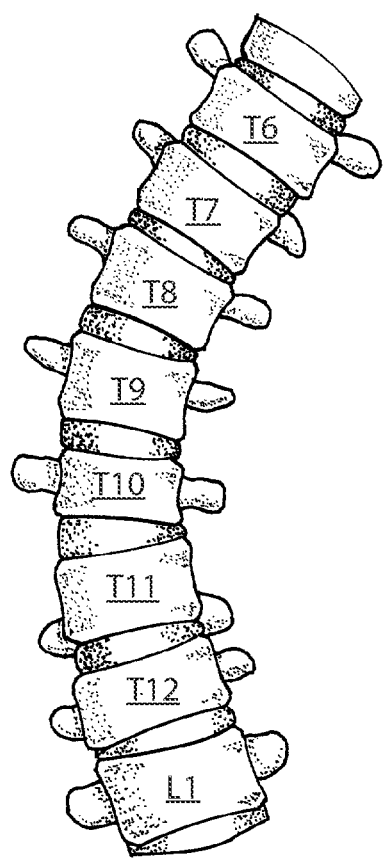
FIG. 18 is an anterior elevation of a thoracic portion of a spine having a stiff curve.
Figure 19:
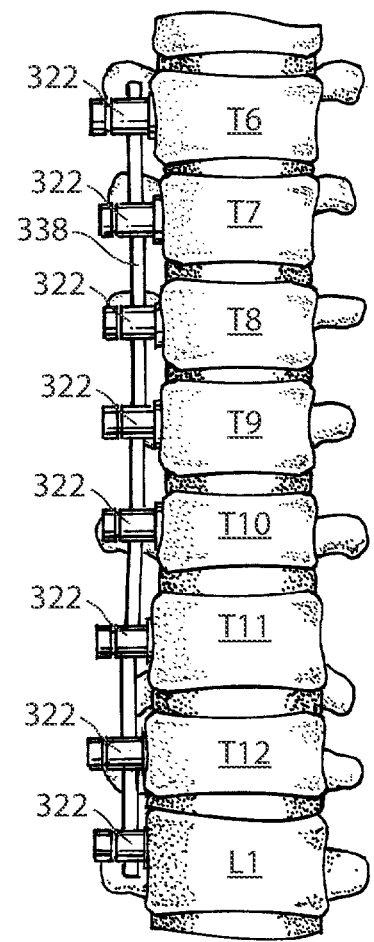
FIG. 19 is the same view as FIG. 18, but shown in a corrected condition.

FIG. 18 illustrates an example of a mature patient with a stiff thoracic curve having undergone disc releases, application of the anterior instrumentation and utilization of the manipulations described above. FIG. 19 is a post-operative illustration showing the corrected spine and the anchor screws 322 and tensioning cord 338 in place.

Figure 20:
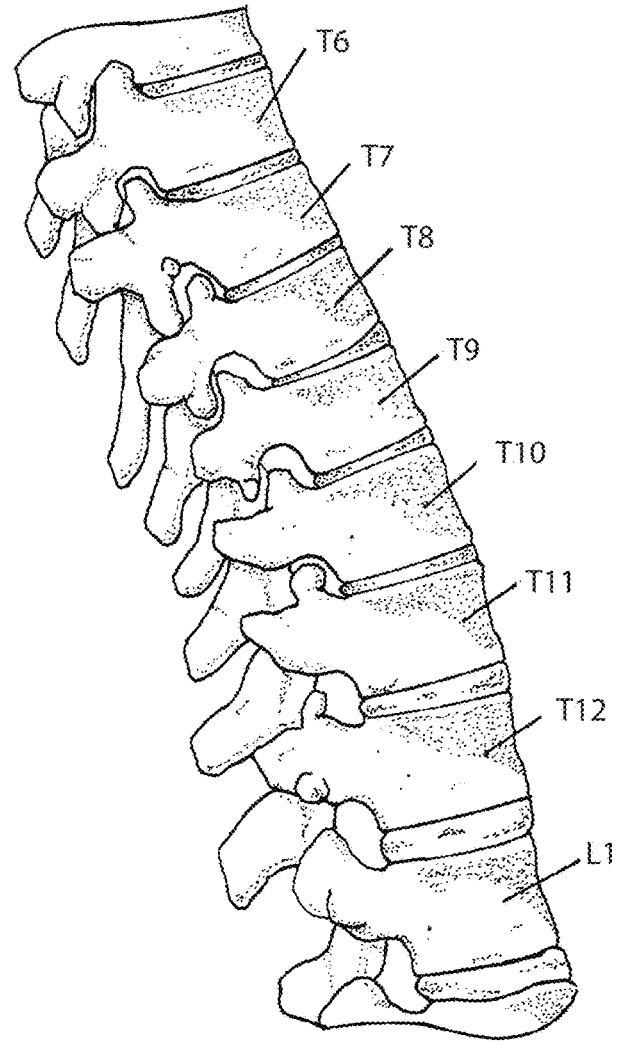
FIG. 20 is a side elevation of a kyphotic spine.
Figure 21:
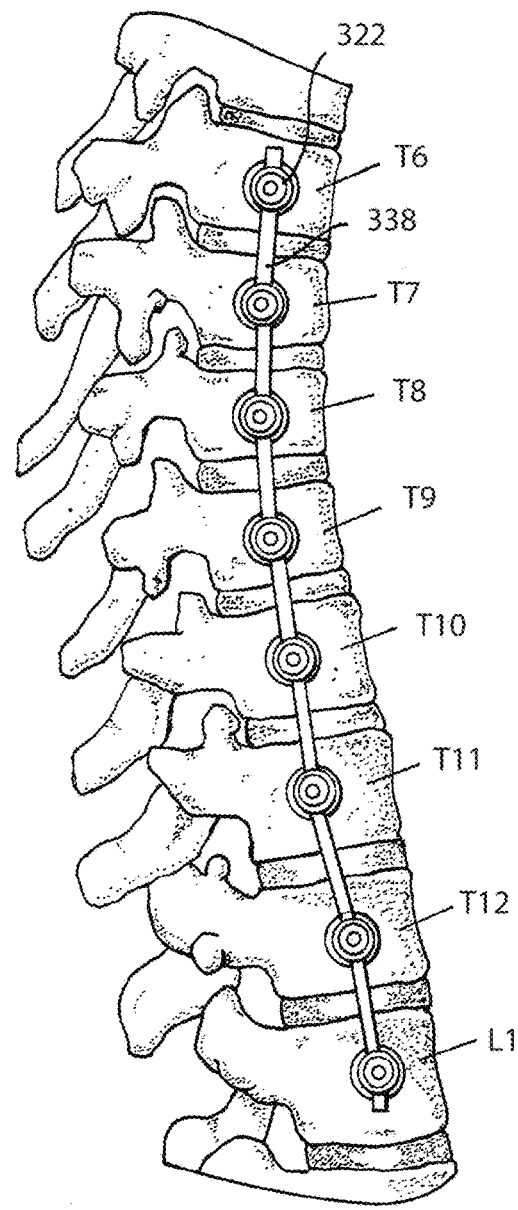
FIG. 21 is the same view as FIG. 20, but shown in a corrected condition.

FIG. 20 illustrates a patient with severe hypokyphosis of the thoracic spine, and FIG. 21 illustrates the restoration of kyphosis having utilized disc releases and de-rotation as described above.

Double Screw/Double Cord Technique

In a third major aspect of the invention, two sets of anchor screws may be used in conjunction with two (or more) tensioning cords in order to provide more precise adjustment of the spine than hereto done in the prior art. This may be of particular importance when treating an excessive angle of scoliosis, such as multiple planes that require de-rotation of the spine for correction. This not only helps with correction of the deformity, but more importantly holds the de-rotation correction more securely then does a single screw/single cord as described above. The single screw/single cord embodiment described above may not be rotationally stable enough for a given application, and it may in certain cases allow the spine to rotate back a few degrees at each segment when the patient is erect, resulting in loss of the ultimate scoliosis correction.

In these cases, a first example of the double cord/double screw methodology is undertaken by inserting two separate and independently operating sets of anchor screws, each set having a different cord that may be tensioned differently by the surgeon. This adds greatly to the rotational stability of the corrective procedure and counters the tendency for the spine to try to rotate back to the uncorrected position. Thus, if possible, it is preferred to implement the inventive double screw/double cord methodology.

In some other cases, a patient may have a severe condition in which a double curve of the spine exists. For example, the upper portion of the spine may curve in one direction, while the lower portion of the spine curves in the opposite direction. To address this problem, a second example of the double cord/double screw methodology is undertaken in which two independent and oppositely disposed sets of double cords/double screws may be implemented to provide more precise correction as will be described further below.

Figure 22:
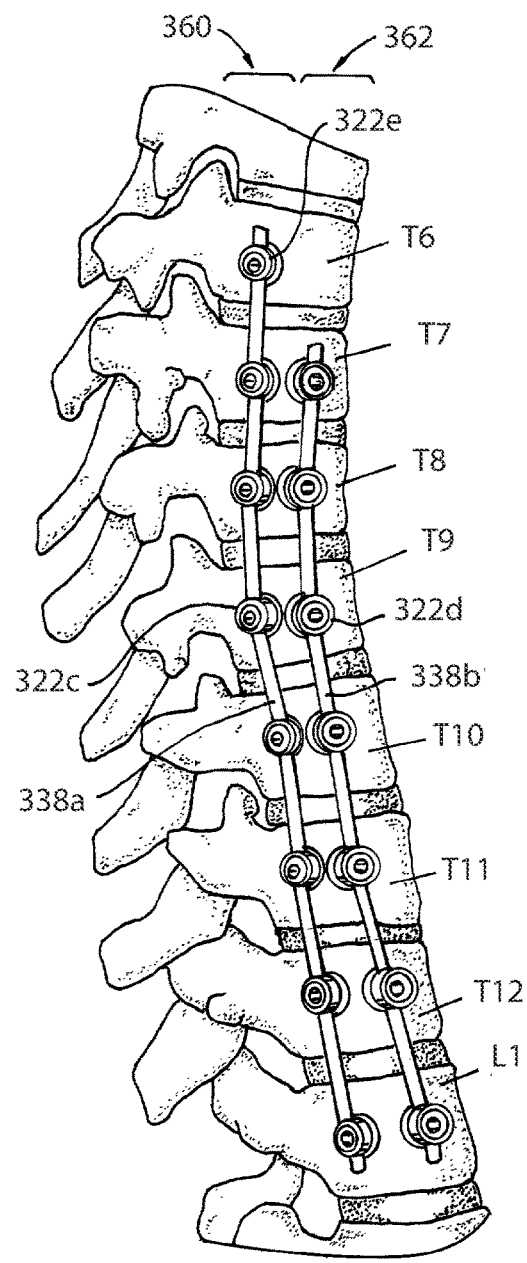
FIG. 22 is a thoracic spine portion shown utilizing a double screw/double cord embodiment.

With respect to the simpler case of a single curve, reference is now made to the thoracic region of FIG. 22, which illustrates two sets of anchor screws (and corresponding staples/washers) inserted in the vertebrae T7, T8, T9, T10, T11, T12, and L1. It is noted that double sets of anchor screws are generally not used for T6, since T6 is relatively smaller and it is difficult for it to maintain adequately two sets of screws due to its smaller mass. The same issue may also exist for T7 if the patient is small.

Figure 1E:
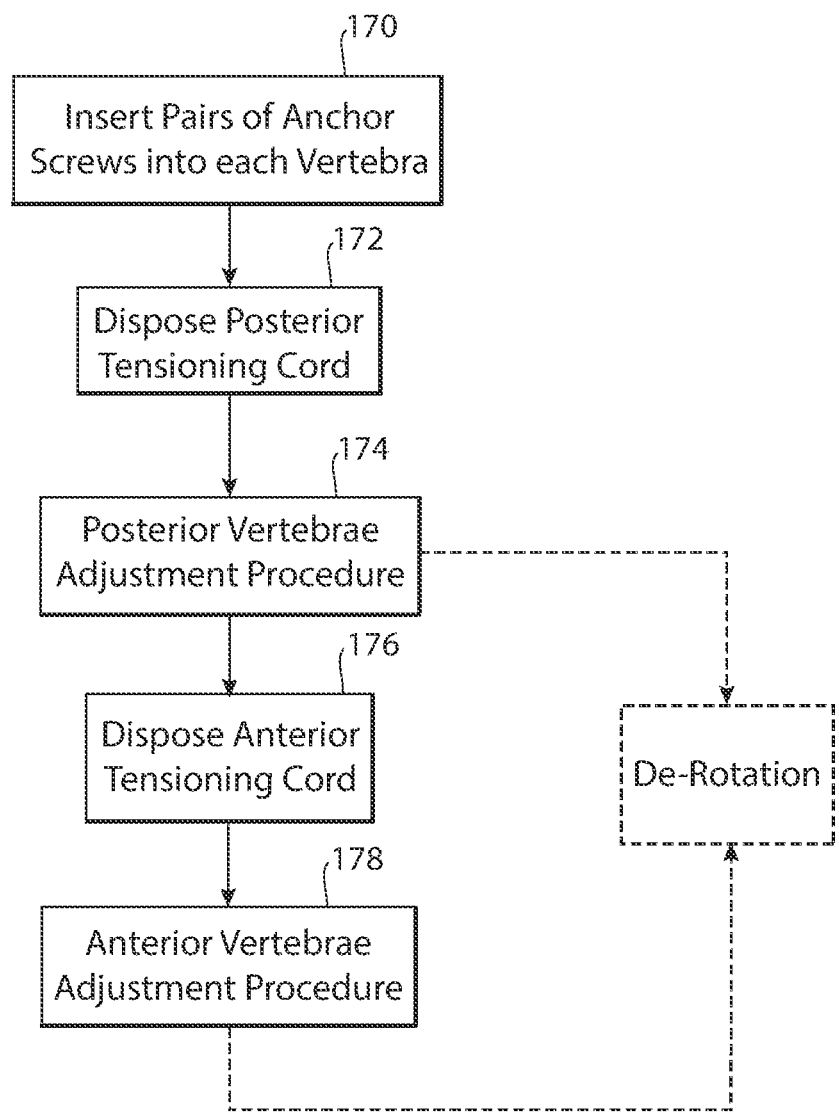
FIG. 1E is a flowchart showing the main steps of a preferred embodiment of the third aspect of the anterior scoliosis correction procedure of the present invention showing the use of double screws and double cords to correct a single scoliosis curve.

With further respect to the flowchart of FIG. 1E, at step 170 multiple pairs of anchor screws 322c, 322d are first inserted into each vertebra T7, T8, T9, T10, T11, T12, and L1 as shown, and a single anchor screw 322e is inserted into T6. As a result of this placement of the pairs of anchor screws 322c, 322d, a substantially aligned posterior row 360 of posterior anchor screws 322c is formed along the vertebrae next to a substantially aligned anterior row 362 of anterior anchor screws 322d formed along the vertebrae.

Next, at step 172, a posterior tensioning cord 338a is disposed within the channels of the posterior anchor screws 322c to enable a posterior adjustment procedure on each of the vertebrae. A posterior vertebrae adjustment procedure is performed at step 176 in which the plurality of vertebrae is adjusted with respect to at least one other vertebra and the posterior tensioning cord 338a is secured within the channels of the corresponding posterior anchor screws 322c in order to maintain the posterior adjustment of the vertebrae.

Likewise, at step 176 an anterior tensioning cord 338b is disposed within the channels of the anterior anchor screws 322d to enable an anterior adjustment procedure on each of the vertebrae. An anterior vertebrae adjustment procedure is performed at step 178 in which each of the plurality of vertebrae is adjusted with respect to at least one other vertebra and the anterior tensioning cord 338b is secured within the channels of the corresponding anterior anchor screws 322d in order to maintain the anterior adjustment of the vertebrae.

Although not required, in the preferred embodiment the posterior vertebrae adjustment procedure and the anterior vertebrae adjustment procedure incorporate the methodologies of the de-rotation procedure described above with respect to the typical single cord situation and as shown in FIGS. 11A, 11B, 12A, 12B, 13A and 13B. In particular, for the posterior vertebrae adjustment de-rotation procedure, a stationary tower is located initially on a first posterior anchor screw 322c of a first vertebra, and a de-rotation tower is located initially on a second posterior anchor screw 322c of a second vertebra. For example, the stationary tower may be located initially on T6 and the de-rotation tower located initially on T7. The posterior de-rotation maneuver is performed by applying a downwards translational force vector to the de-rotation tower, applying a lateral force vector to the de-rotation tower, and simultaneously applying a lateral counterforce vector to the stationary tower in opposition to the lateral force vector being applied to the de-rotation tower. Next, the posterior tensioning cord 338a is tensioned in the channel of the second posterior anchor screw 322c (on T7) and secured in the channel of the second posterior anchor screw 322c in order to maintain the de-rotation of the T7 vertebra. The de-rotation tower is then re-located to the posterior anchor screw 322c of the next vertebra (e.g. T8), and the de-rotation maneuver is repeated until all of the vertebrae have been de-rotated using the posterior tensioning cord 338a as desired.

After this posterior vertebrae adjustment de-rotation procedure is performed on all the vertebrae as desired, the anterior vertebrae adjustment de-rotation procedure is performed in a similar manner. That is, for the anterior vertebrae adjustment de-rotation procedure, a stationary tower is located initially on a first anterior anchor screw 322d of a first vertebra (e.g. T7), and a de-rotation tower is located initially on a second anterior anchor screw 322d of a second vertebra (e.g. T8). The anterior de-rotation maneuver is performed by applying a downwards translational force vector to the de-rotation tower, applying a lateral force vector to the de-rotation tower, and simultaneously applying a lateral counterforce vector to the stationary tower in opposition to the lateral force vector being applied to the de-rotation tower. Next, the anterior tensioning cord 338b is tensioned in the channel of the second anterior anchor screw 322d (on T8) and secured in the channel of at the second anterior anchor screw 322d in order to maintain the de-rotation of the T8 vertebra. The de-rotation tower is then re-located to the anterior anchor screw 322d of the next vertebra (e.g. T9), and the de-rotation maneuver is repeated until all of the vertebrae have been de-rotated using the anterior tensioning cord 338b as desired. Note that since the initial posterior vertebrae adjustment procedure has likely substantially aligned the vertebrae, the amount of adjustment provided by the anterior vertebrae adjustment procedure may be only incremental, but is still useful in maintaining alignment of the vertebrae. In an alternative embodiment, the anterior vertebrae adjustment procedure may be executed before the posterior vertebrae adjustment procedure, if desired.

As a result, FIG. 22 illustrates the corrected spine, with all vertebrae shown corrected using the posterior tensioning cord 338a and the anterior tensioning cord 338b as explained above.

Figure 23:
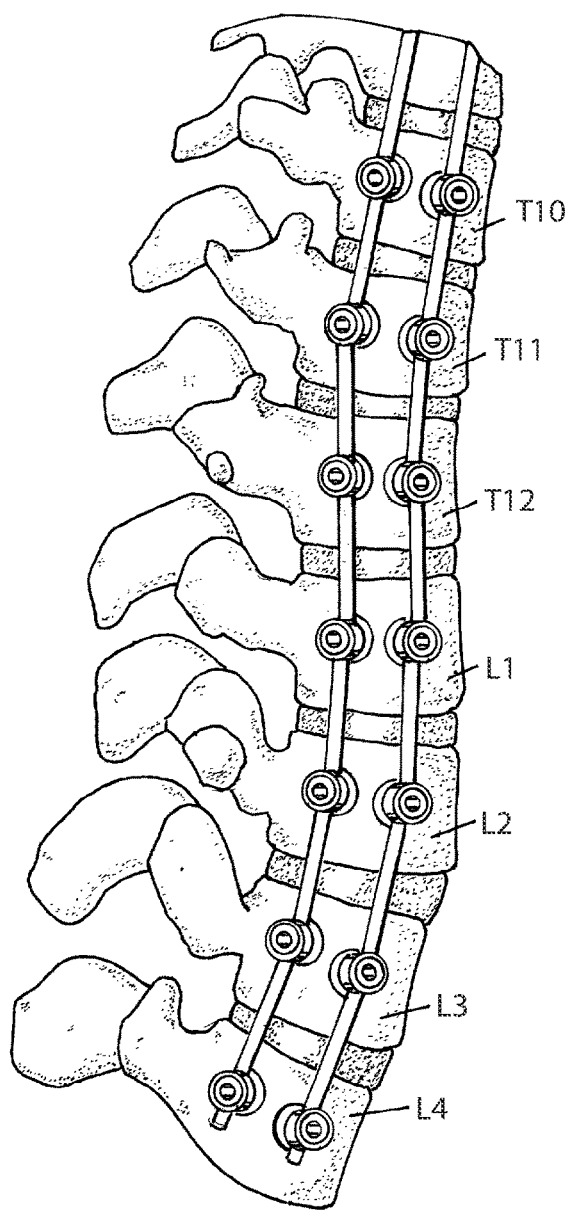
FIG. 23 is a lumbar spine portion shown utilizing a double screw/double cord embodiment.

In FIG. 23, a lumbar curve is shown at T10, T11, T12, L1, L2, L3, and L4. Here, the use of two sets of screws and two tensioning cords may be taken advantage of since these vertebrae have enough mass to hold both sets adequately. The process for correction of the vertebrae is carried out in a similar manner as described above with respect to FIG. 22.

Figure 24:
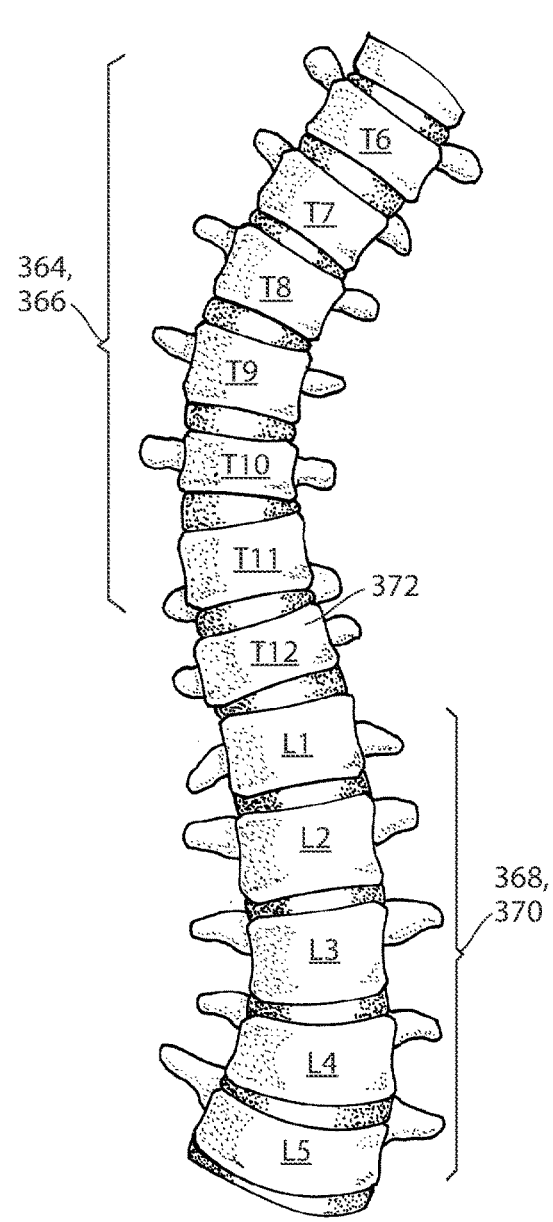
FIG. 24 is a is an anterior elevation of a spine having a double curve.

FIG. 24 is a is an anterior elevation of a spine having a double curve consisting of an upper curve 364 and a lower curve 368. Here, it is desired to use double screws/double cords to correct both of the curves and to maintain rotation and decrease fatigue on the cord(s). It is noted that in this example, T12 is considered to be neutral since it is essentially the transitional bridge between the upper curve 364 and the lower curve 368. As such, we are unable to place double screws on each side of T12, as the mass of T12 would not enable it to hold four screws in total. So, in this example, a single screw is used on each side of T12 in order to bridge the transition between the curves as follows.

In FIG. 24, the upper curve 364 is defined by an upper set of vertebrae 366 (T6, T7, T8, T9, T10, and T11) and the lower curve 368 is defined by a lower set of vertebrae 370 (L1, L2, L3, and L4). In this example, the upper curve 364 is disposed in a first direction, and the lower curve is disposed in substantially the opposite direction, thus presenting the problem that is addressed by this invention. T12 is considered to be a neutral vertebra 372 since it is located between the upper set of vertebrae 366 and the lower set of vertebrae 370 and is essentially a transition between the two curves.

Figure 25:
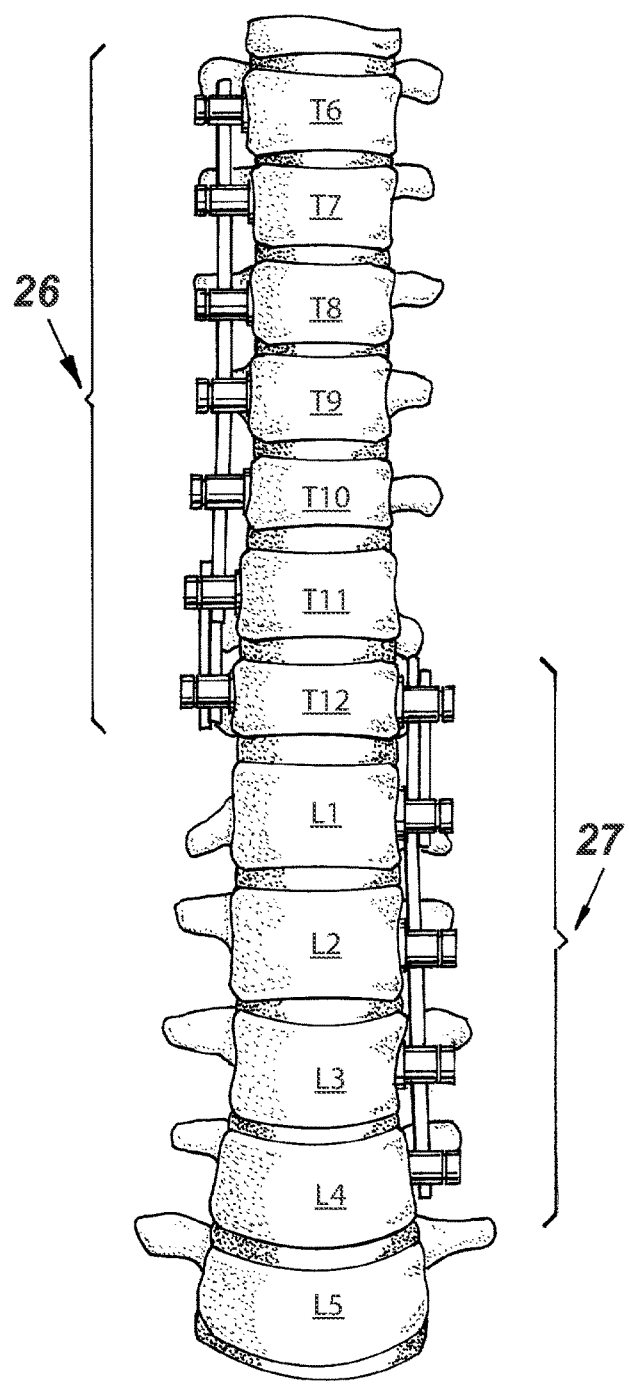
FIG. 25 is the same view as FIG. 24 showing the placement of the double sets of anchor screws and cords on each of the curves, after vertebral correction.

As can be seen from FIGS. 25, 26 and 27, the layout of the anchor screws for the two separate curves results in four distinct regions; upper posterior and upper anterior (see FIG. 26), and lower posterior and lower anterior (see FIG. 27). In general, the surgeon will insert all of the anchor screws into the vertebrae in these four regions and then perform the separate adjustment procedures (e.g. de-rotation) on the four different regions using the appropriate tensioning cords in order to accomplish the desired straightening of the spine, using an upper posterior adjustment procedure, an upper anterior adjustment procedure, a lower posterior adjustment procedure, and a lower anterior adjustment procedure. It is noted that in order to access the vertebrae in the upper curve (right thoracic curve), the mini-opening is made at the right chest as described above, and in order to access the vertebrae in the lower curve (left lumbar curve), a second mini-opening is made at the left lower chest.

Thus, for the upper set of vertebrae 366, shown in detail in FIG. 26, the surgeon inserts pairs of anchor screws into each of the upper vertebrae 366 along the convexity of the upper curve 364, such that a substantially aligned upper posterior row 374 of upper posterior anchor screws 322f are formed along the upper vertebrae 366 next to a substantially aligned upper anterior row 376 of upper anterior anchor screws 322g formed along the upper vertebrae 366.

For the lower set of vertebrae 370, shown in detail in FIG. 27, the surgeon inserts pairs of anchor screws into each of the lower vertebrae 370 along the convexity of the lower curve 368 (which is substantially opposite the convexity of the upper curve 364 as shown), such that a substantially aligned lower posterior row 378 of lower posterior anchor screws 322h are formed along the lower vertebrae 370 next to a substantially aligned lower anterior row 380 of lower anterior anchor screws 322i formed along the lower vertebrae 370.

For the neutral vertebra 372, the surgeon inserts an upper neutral posterior anchor screw 322j into the neutral vertebra 372 on the same side as the upper curve 364, and the surgeon also inserts a lower neutral posterior anchor screw 322k into the neutral vertebra 372 on the same side as the lower curve 368.

The upper set of screws 322f, 322g, 322j on the patient's right side will address the upper curve to her right side as shown, and the lower set of screws 322h, 322i, 322k will address the lower curve on the patient's left side as shown.

Referring again to FIG. 26, during the upper posterior adjustment procedure on the upper set of vertebrae 366, an upper posterior tensioning cord 338c is disposed within the channels of the upper posterior anchor screws 322f and the upper neutral posterior anchor screw 322j, and an upper bridge posterior tensioning cord 338e is disposed within the channels of the upper neutral posterior anchor screw 322j and the upper posterior anchor screw 322f adjacent the upper neutral posterior anchor screw 322j. The upper bridge posterior tensioning cord 338e overlaps the relevant portion of the upper posterior tensioning cord 338c since they share the same set of anchor screws 322f, 322j.

Likewise, during the upper anterior adjustment procedure on the upper set of vertebrae 366, an upper anterior tensioning cord 338d is disposed within the channels of the upper anterior anchor screws 322g.

Referring again to FIG. 27, during the lower posterior adjustment procedure on the lower set of vertebrae 370, a lower posterior tensioning cord 338f is disposed within the channels of the lower posterior anchor screws 322h and the lower neutral posterior anchor screw 322k, and a lower bridge posterior tensioning cord 338h is disposed within the channels of the lower neutral posterior anchor screw 322k and the lower posterior anchor screw 322h adjacent the lower neutral posterior anchor screw 322k. The lower bridge posterior tensioning cord 338h overlaps the relevant portion of the lower posterior tensioning cord 338f since they share the same set of anchor screws 322h, 322k.

Likewise, during the lower anterior adjustment procedure on the lower set of vertebrae 370, a lower anterior tensioning cord 338g is disposed within the channels of each of the lower anterior anchor screws 322i.

The surgeon performs the adjustment procedures on the four different regions (upper posterior, upper anterior, lower posterior, lower anterior) as follows (preferably but not necessarily in that order).

The surgeon performs the upper posterior vertebrae adjustment procedure in which each of the set of upper vertebrae 366 is adjusted with respect to at least one other upper vertebra and the upper posterior tensioning cord 338c and upper bridge posterior tensioning cord 338e are each secured within the channels of the corresponding upper posterior anchor screws 322f (and the upper neutral posterior anchor screw 322j) in order to maintain the upper posterior adjustment of the vertebrae. The surgeon then performs the upper anterior vertebrae adjustment procedure in which each of the set of upper vertebrae 366 is adjusted with respect to at least one other upper vertebra and the upper anterior tensioning cord 338d is secured within the channels of the corresponding upper anterior anchor screws 322g in order to maintain the upper anterior adjustment of the vertebrae.

The surgeon performs the lower posterior vertebrae adjustment procedure in which each of the set of lower vertebrae 370 is adjusted with respect to at least one other lower vertebra and the lower posterior tensioning cord 338f and lower bridge posterior tensioning cord 338h are each secured within the channels of the corresponding lower posterior anchor screws 322h (and the lower neutral posterior anchor screw 322k) in order to maintain the lower posterior adjustment of the vertebrae. The surgeon then performs the lower anterior vertebrae adjustment procedure in which each of the set of lower vertebrae 370 is adjusted with respect to at least one other lower vertebra and the lower anterior tensioning cord 338g is secured within the channels of the corresponding lower anterior anchor screws 322i in order to maintain the lower anterior adjustment of the vertebrae.

In a preferred embodiment, each of the above vertebrae adjustment procedures (i.e. the upper posterior vertebrae adjustment procedure, upper anterior vertebrae adjustment procedure, lower posterior vertebrae adjustment procedure, and lower anterior vertebrae adjustment procedure) is executed using the de-rotation procedure described above.

Thus, the upper posterior vertebrae de-rotation procedure is performed by the surgeon locating a stationary tower on a first upper posterior anchor screw of a first upper vertebra and a de-rotation tower on a second upper posterior anchor screw of a second upper vertebra. A de-rotation maneuver is performed by applying a downwards translational force vector to the de-rotation tower, applying a lateral force vector to the de-rotation tower, and simultaneously applying a lateral counterforce vector to the stationary tower in opposition to the lateral force vector being applied to the de-rotation tower. The surgeon tensions the upper posterior tensioning cord in the channel of the second upper posterior anchor screw, and then secures the upper posterior tensioning cord in the channel of at the second upper posterior anchor screw in order to maintain the de-rotation of the upper vertebrae. The de-rotation tower is re-located to the upper posterior anchor screw of a subsequent upper vertebra, and the de-rotation maneuvers are repeated until all of the upper vertebrae have been de-rotated as desired. When adjusting the neutral vertebra, both the upper posterior tensioning cord and the upper bridge tensioning cord are tensioned and secured simultaneously.

The upper anterior vertebrae de-rotation procedure is performed by the surgeon locating a stationary tower on a first upper anterior anchor screw of a first upper vertebra and a de-rotation tower on a second upper anterior anchor screw of a second upper vertebra. A de-rotation maneuver is performed by applying a downwards translational force vector to the de-rotation tower, applying a lateral force vector to the de-rotation tower, and simultaneously applying a lateral counterforce vector to the stationary tower in opposition to the lateral force vector being applied to the de-rotation tower. The surgeon tensions the upper anterior tensioning cord in the channel of the second upper anterior anchor screw, and then secures the upper anterior tensioning cord in the channel of at the second upper anterior anchor screw in order to maintain the de-rotation of the upper vertebrae. The de-rotation tower is re-located to the upper anterior anchor screw of a subsequent upper vertebra, and the de-rotation maneuvers are repeated until all of the upper vertebrae have been de-rotated as desired.

The lower posterior vertebrae de-rotation procedure is performed by the surgeon locating a stationary tower on a first lower posterior anchor screw of a first lower vertebra and a de-rotation tower on a second lower posterior anchor screw of a second lower vertebra. A de-rotation maneuver is performed by applying a downwards translational force vector to the de-rotation tower, applying a lateral force vector to the de-rotation tower, and simultaneously applying a lateral counterforce vector to the stationary tower in opposition to the lateral force vector being applied to the de-rotation tower. The surgeon tensions the lower posterior tensioning cord in the channel of the second lower posterior anchor screw, and then secures the lower posterior tensioning cord in the channel of at the second lower posterior anchor screw in order to maintain the de-rotation of the lower vertebrae. The de-rotation tower is re-located to the lower posterior anchor screw of a subsequent lower vertebra, and the de-rotation maneuvers are repeated until all of the lower vertebrae have been de-rotated as desired. When adjusting the neutral vertebra, both the lower posterior tensioning cord and the lower bridge tensioning cord are tensioned and secured simultaneously.

The lower anterior vertebrae de-rotation procedure is performed by the surgeon locating a stationary tower on a first lower anterior anchor screw of a first lower vertebra and a de-rotation tower on a second lower anterior anchor screw of a second lower vertebra. A de-rotation maneuver is performed by applying a downwards translational force vector to the de-rotation tower, applying a lateral force vector to the de-rotation tower, and simultaneously applying a lateral counterforce vector to the stationary tower in opposition to the lateral force vector being applied to the de-rotation tower. The surgeon tensions the lower anterior tensioning cord in the channel of the second lower anterior anchor screw, and then secures the lower anterior tensioning cord in the channel of at the second lower anterior anchor screw in order to maintain the de-rotation of the lower vertebrae. The de-rotation tower is re-located to the lower anterior anchor screw of a subsequent lower vertebra, and the de-rotation maneuvers are repeated until all of the lower vertebrae have been de-rotated as desired.

Figure 38:
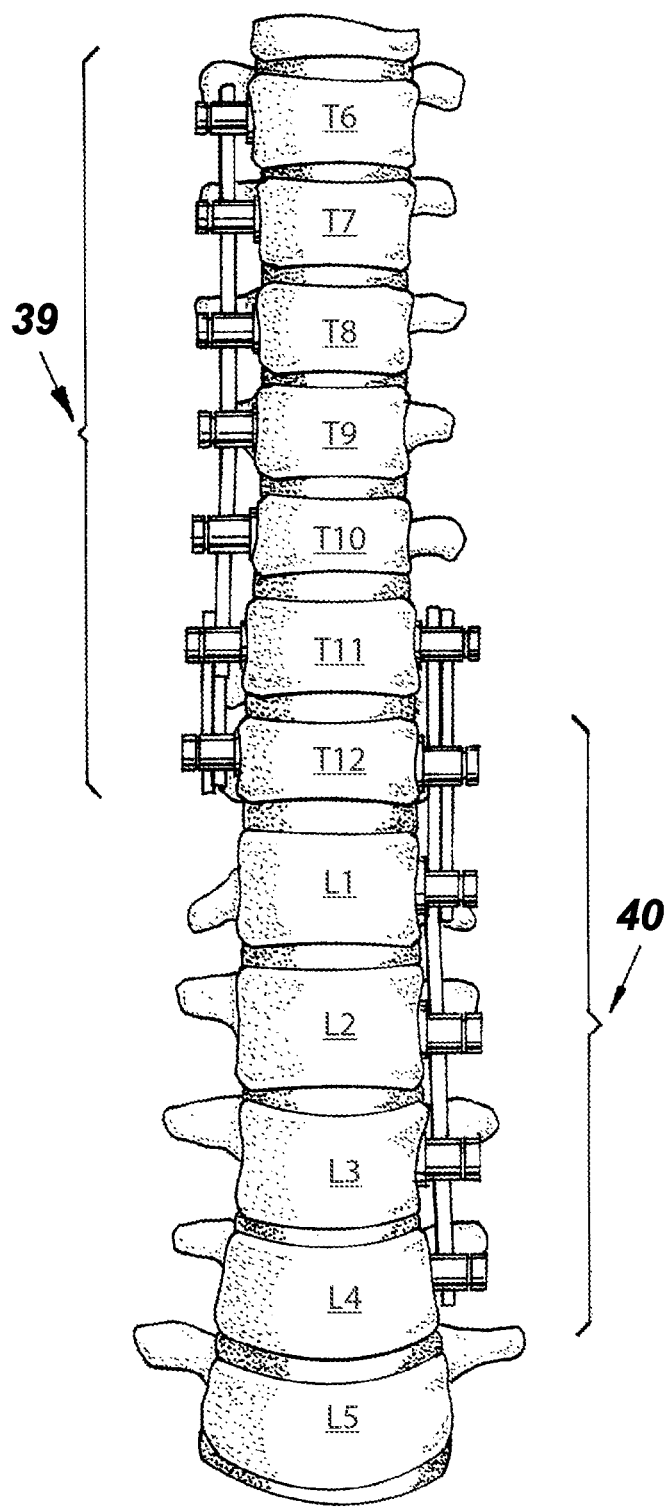
FIG. 38 illustrates an alternative embodiment of the correction of the double curve condition as in FIG. 25, but with two sets of anchor screws on each side of T11 and T12.
Figure 39:
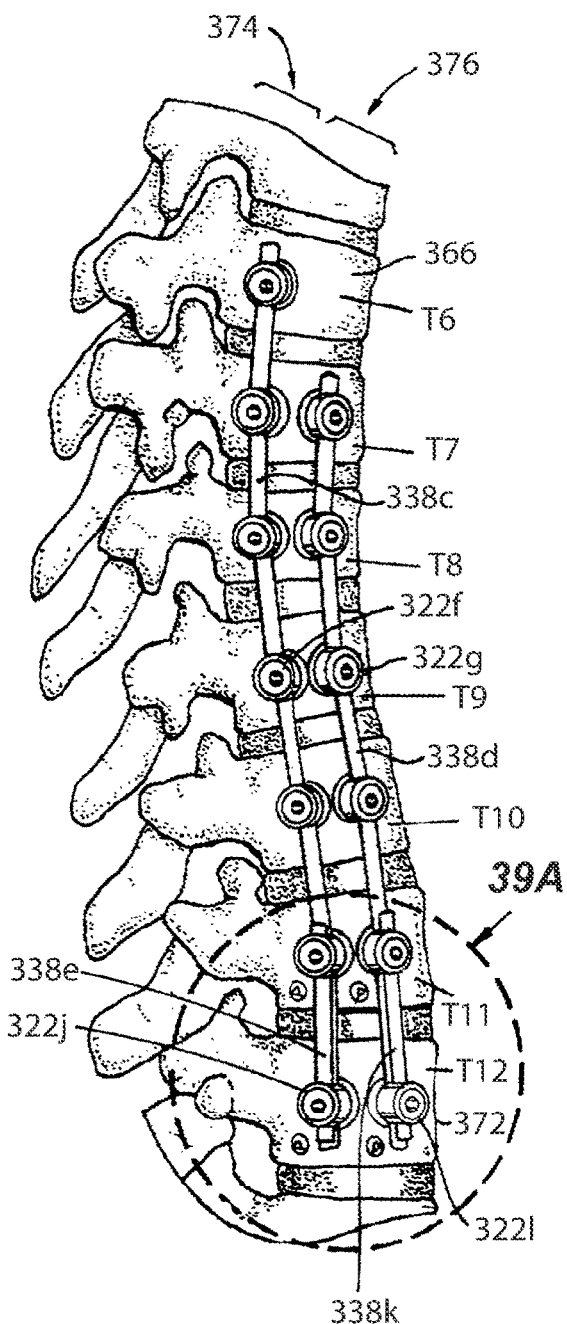
FIG. 39 is a is a thoracic side elevation, taken at arrow 39 of FIG. 38, showing the double screw/double cord set up in which two anchor screws are inserted into T12 as well as T11 on the thoracic side.
Figure 39A:
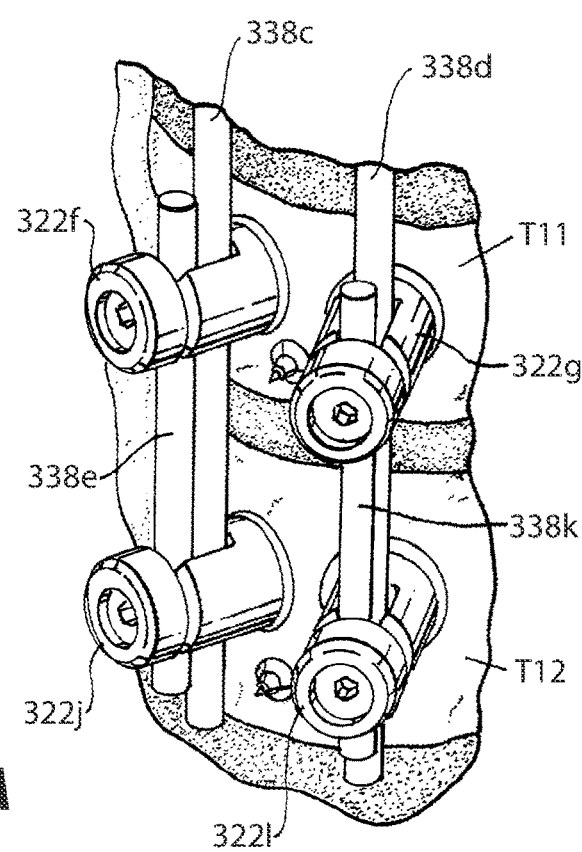
FIG. 39A is an enlarged perspective view, taken at arrow 39a of FIG. 39, showing the anchor screws and cord doubling in which two anchor screws are inserted into T12 as well as T11 on the thoracic side.

In certain cases, the vertebrae of the patient may have enough mass to support additional anchor screws at the neutral (i.e. transition) zone around T12. Referring now to an alternative embodiment in FIG. 38, illustrated is the correction of a double curve condition as in FIG. 25 above, but with two sets of anchor screws on each side of T11 and T12. Shown in further detail in FIG. 39, a thoracic side elevation taken at arrow 39 of FIG. 38 shows the double screw/double cord set up in which two anchor screws are inserted into T12 as well as T11 on the thoracic side. FIG. 39A is an enlarged perspective view, taken at arrow 39A of FIG. 39, showing the anchor screws and cord doubling in which the two anchor screws are inserted into T12 as well as T11 on the thoracic side. That is, in addition to the upper neutral posterior anchor screw 322*j* on T12, we have added an upper neutral anterior anchor screw 322*l*.

Figure 40:
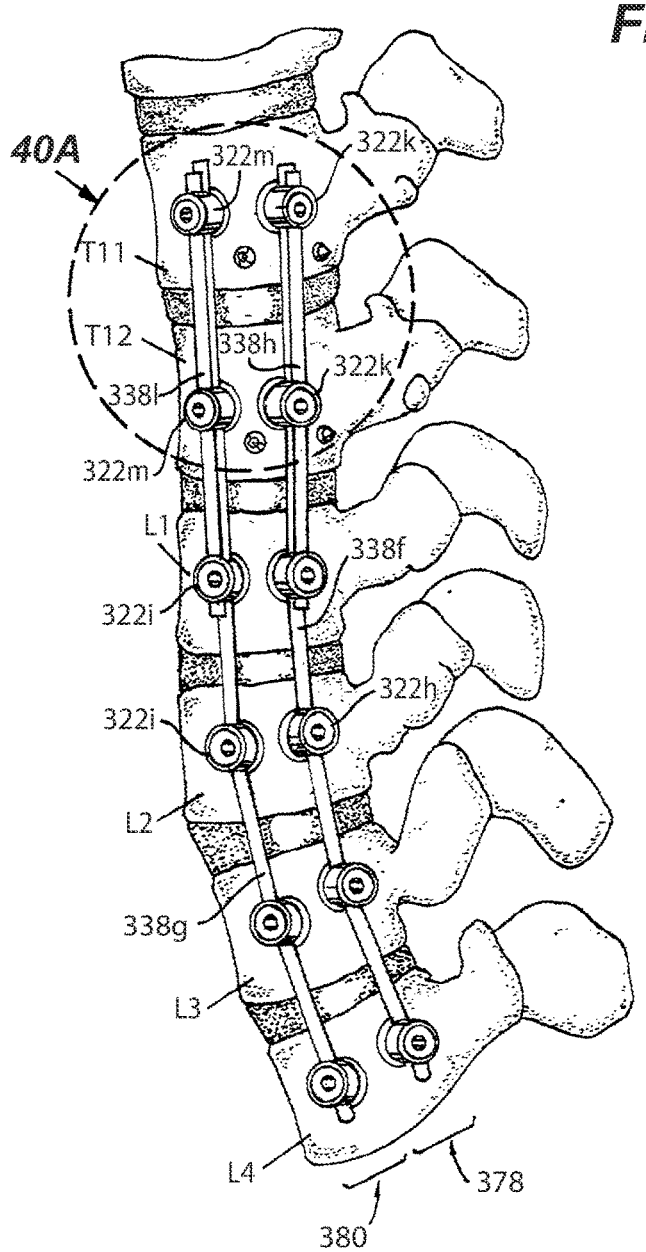
FIG. 40 is a lumbar side elevation, taken at arrow 40 of FIG. 38, showing the double screw/double cord set up in which T11 and T12 are provided with two anchor screws each on the lumbar side.
Figure 40A:
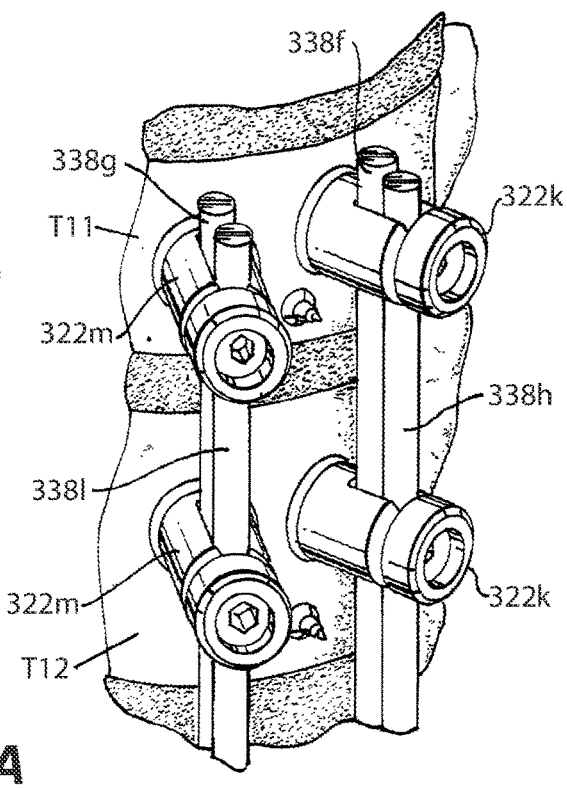
FIG. 40A is an enlarged perspective view, taken at arrow 40a of FIG. 40, showing the anchor screws and cord doubling in which T11 and T12 are provided with two anchor screws each on the lumbar side.

Similarly, FIG. 40 is a lumbar side elevation, taken at arrow 40 of FIG. 38, showing the double screw/double cord set up in which T11 and T12 are provided with two anchor screws each on the lumbar side, and FIG. 40A is an enlarged perspective view, taken at arrow 40A of FIG. 40, showing the anchor screws and cord doubling in which T11 and T12 are provided with two anchor screws each on the lumbar side in this alternative embodiment. That is, in addition to the lower neutral posterior anchor screw 322*k* on T12, we have added a lower neutral anterior anchor screw 322*m* to T12. On T11, we have added a second lower neutral posterior anchor screw 322*k* as well as a second lower neutral anterior anchor screw 322*m* onto T11, as shown.

Implementing four anchor screws (two on each side) of both T11 and T12, in cases where the bone mass is sufficient, provides the advantage of more control and support with respect to the primary embodiment described earlier.

Placement of tensioning cords in this alternative embodiment is now described. On the thoracic side shown in FIGS. 39 and 39A, the upper posterior tensioning cord 338*c* and the upper bridge posterior tensioning cord 338*e* are configured as in FIG. 26 described above, but now the upper anterior tensioning cord 338*d* is extended through the upper neutral anterior anchor screw 322*l* on T12, and an additional upper bridge anterior tensioning cord 338*k* has been added within the upper anterior anchor screw 322*g* on T11 and the newly added upper neutral anterior anchor screw 322*l*.

On the lumbar side shown in FIGS. 40 and 40A, the lower posterior tensioning cord 338*f* and the lower bridge posterior tensioning cord 338*h* are both now extended through the additional lower neutral posterior anchor screw 322*k* that has been inserted into T11. The lower anterior tensioning cord 338*g* is similarly extended through both of the lower neutral anterior anchor screws 322*m* located on T12 and T11, respectively. An additional cord, the lower bridge anterior tensioning cord 338*l*, is located through the lower anterior anchor screw 322*i* located on L1 and then through both of the lower neutral anterior anchor screws 322*m* located on T12 and T11, respectively.

The configuration of the various tensioning cords illustrated in this alternative embodiment of FIGS. 38, 39, 39A, 40 and 40A are exemplary and may be adapted and modified in various situations, depending on the tensioning desired by the surgeon for a given patient. For example, the surgeon may decide to use the lower bridge anterior tensioning cord 338*l* with the lower neutral anterior anchor screws 322*m* on T11 and T12 but not extend through the lower anterior anchor screw 322*i* on L1, and the like. Or, certain cords may be crossed over from anterior to posterior and/or posterior to anterior, as described further below in the alternative embodiments.

This alternative embodiment is advantageous since in some cases, with only a single cord in the neutral transition zone, if the single cord breaks in one location the vertebra could potentially shift from one curve into the other. This alternative arrangement can ameliorate such a potential problem by providing multiple screws and extended cords throughout the neutral transition area if the bone mass will support it.

Thus, in the improved method disclosed herein, a plurality of anchor screws are inserted into corresponding vertebrae to enable the spinal correction, wherein each of the anchor screws comprises a channel suitable for accepting a tensioning cord; the vertebrae forming a double scoliosis curve comprising an upper curve defined by an upper set of vertebrae disposed substantially in a first direction, a lower curve defined by a lower set of vertebrae disposed substantially in a second direction substantially opposite to the first direction, and a neutral vertebra located between the upper set of vertebrae and the lower set of vertebrae. In this improved method, for the upper set of vertebrae, a pair of anchor screws is inserted into each of the plurality of upper vertebrae and the neutral vertebra along the convexity of the upper curve, such that a substantially aligned upper posterior row of upper posterior anchor screws are formed along the upper vertebrae and the neutral vertebra next to a substantially aligned upper anterior row of upper anterior anchor screws formed along the upper vertebrae and the neutral vertebra.

For the lower set of vertebrae, a pair of anchor screws is inserted into each of the plurality of lower vertebrae and the neutral vertebra along the convexity of the lower curve which is substantially opposite the convexity of the upper curve, such that a substantially aligned lower posterior row of lower posterior anchor screws are formed along the lower vertebrae and the neutral vertebra next to a substantially aligned lower anterior row of lower anterior anchor screws formed along the lower vertebrae and the neutral vertebra.

An upper posterior tensioning cord is disposed within the channels of the upper posterior row of upper posterior anchor screws to enable an upper posterior adjustment procedure on the upper set of vertebrae and the neutral vertebra. An upper posterior vertebrae adjustment procedure is performed in which each of the set of upper vertebrae and the neutral vertebra is adjusted with respect to at least one other upper vertebra and the upper posterior tensioning cord is secured within the channel of the corresponding upper posterior anchor screw in order to maintain the upper posterior adjustment of the vertebrae.

An upper anterior tensioning cord is disposed within the channels of the upper anterior row of upper anterior anchor screws to enable an upper anterior adjustment procedure on the upper set of vertebrae and the neutral vertebra. An upper anterior vertebrae adjustment procedure is performed in which each of the set of upper vertebrae and the neutral vertebra is adjusted with respect to at least one other upper vertebra and the upper anterior tensioning cord is secured within the channel of the corresponding upper anterior anchor screw in order to maintain the upper anterior adjustment of the vertebrae.

A lower posterior tensioning cord is disposed within the channels of the lower posterior row of lower posterior anchor screws to enable a lower posterior adjustment procedure on the lower set of vertebrae and the neutral vertebra. A lower posterior vertebrae adjustment procedure is performed in which each of the set of lower vertebrae and the neutral vertebra is adjusted with respect to at least one other lower vertebra and the lower posterior tensioning cord is secured within the channel of the corresponding lower posterior anchor screw in order to maintain the lower posterior adjustment of the vertebrae.

A lower anterior tensioning cord is disposed within the channels of the lower anterior row of lower anterior anchor screws to enable a lower anterior adjustment procedure on the lower set of vertebrae and the neutral vertebra. A lower anterior vertebrae adjustment procedure is performed in which each of the set of lower vertebrae and the neutral vertebra is adjusted with respect to at least one other lower vertebra and the lower anterior tensioning cord is secured within the channel of the corresponding lower anterior anchor screw in order to maintain the lower anterior adjustment of the vertebrae.

In an optional embodiment, a second upper posterior tensioning cord is disposed within the channels of the upper posterior row of upper posterior anchor screws next to the upper posterior tensioning cord; a second upper anterior tensioning cord is disposed within the channels of the upper anterior row of upper anterior anchor screws next to the upper anterior tensioning cord; a second lower posterior tensioning cord is disposed within the channels of the lower posterior row of lower posterior anchor screws next to the lower posterior tensioning cord; and a second lower anterior tensioning cord is disposed within the channels of the lower anterior row of lower anterior anchor screws next to the lower anterior tensioning cord.

Optionally, the upper posterior vertebrae adjustment procedure is a de-rotation procedure comprising the steps of locating a stationary tower on a first upper posterior anchor screw of a first upper vertebra, locating a de-rotation tower on a second upper posterior anchor screw of a second upper vertebra, performing a de-rotation maneuver by applying a downwards translational force vector to the de-rotation tower, applying a lateral force vector to the de-rotation tower, and simultaneously applying a lateral counterforce vector to the stationary tower in opposition to the lateral force vector being applied to the de-rotation tower, tensioning the upper posterior tensioning cord in the channel of the second upper posterior anchor screw, securing the upper posterior tensioning cord in the channel of the second upper posterior anchor screw in order to maintain the de-rotation of the upper vertebrae, re-locating the de-rotation tower to the upper posterior anchor screw of a subsequent upper vertebra, and repeating the de-rotation maneuver until all of the upper vertebrae and the neutral vertebra have been de-rotated as desired.

Further optionally, the upper anterior vertebrae adjustment procedure is a de-rotation procedure comprising the steps of locating a stationary tower on a first upper anterior anchor screw of a first upper vertebra, locating a de-rotation tower on a second upper anterior anchor screw of a second upper vertebra, performing a de-rotation maneuver by applying a downwards translational force vector to the de-rotation tower, applying a lateral force vector to the de-rotation tower, and simultaneously applying a lateral counterforce vector to the stationary tower in opposition to the lateral force vector being applied to the de-rotation tower, tensioning the upper anterior tensioning cord in channel of the second upper anterior anchor screw, securing the upper anterior tensioning cord in the channel of the second upper anterior anchor screw in order to maintain the de-rotation of the upper vertebrae, re-locating the de-rotation tower to the upper anterior anchor screw of a subsequent upper vertebra, and repeating the de-rotation maneuver until all of the upper vertebrae and the neutral vertebra have been de-rotated as desired.

Still further optionally, the lower posterior vertebrae adjustment procedure is a de-rotation procedure comprising the steps of locating a stationary tower on a first lower posterior anchor screw of a first lower vertebra, locating a de-rotation tower on a second lower posterior anchor screw of a second lower vertebra, performing a de-rotation maneuver by applying a downwards translational force vector to the de-rotation tower, applying a lateral force vector to the de-rotation tower, and simultaneously applying a lateral counterforce vector to the stationary tower in opposition to the lateral force vector being applied to the de-rotation tower, tensioning the lower posterior tensioning cord in channel of the second lower posterior anchor screw, securing the lower posterior tensioning cord in the channel of the second lower posterior anchor screw in order to maintain the de-rotation of the lower vertebrae, re-locating the de-rotation tower to the lower posterior anchor screw of a subsequent lower vertebra, and repeating the de-rotation maneuver until all of the lower vertebrae and the neutral vertebra have been de-rotated as desired.

Finally, the lower anterior vertebrae adjustment procedure may be a de-rotation procedure comprising the steps of locating a stationary tower on a first lower anterior anchor screw of a first lower vertebra, locating a de-rotation tower on a second lower anterior anchor screw of a second lower vertebra, performing a de-rotation maneuver by applying a downwards translational force vector to the de-rotation tower, applying a lateral force vector to the de-rotation tower, and simultaneously applying a lateral counterforce vector to the stationary tower in opposition to the lateral force vector being applied to the de-rotation tower, tensioning the lower anterior tensioning cord in channel of the second lower anterior anchor screw, securing the lower anterior tensioning cord in the channel of the second lower anterior anchor screw in order to maintain the de-rotation of the lower vertebrae, re-locating the de-rotation tower to the lower anterior anchor screw of a subsequent lower vertebra, and repeating the de-rotation maneuver until all of the lower vertebrae and the neutral vertebra have been de-rotated as desired.

ALTERNATIVE EMBODIMENTS

Several alternative embodiments may be implemented, alone or in conjunction with each other, as now described below.

Non-Centered Anchor Screws

In the main embodiments described above, the anchor screws 322 are inserted in substantially the center of the side(s) of the vertebrae in order to provide enough surrounding bone mass for the anchor screw to maintain its placement and not plow through or out of the bone. However, in some instances, it may be possible to offset the anchor screws either horizontally and/or vertically off-center of the side(s) of the vertebrae in order to provide certain biomechanical advantages that will aid in the vertebrae adjustment procedures, as now further described.

Figure 28:
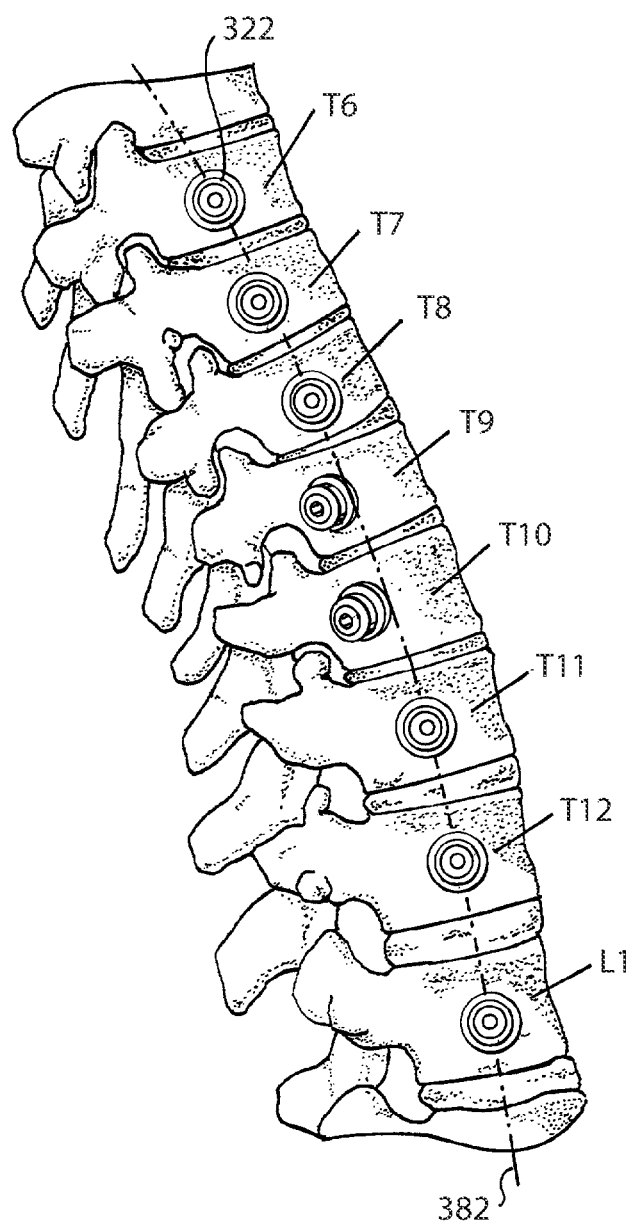
FIG. 28 is a side elevation of a kyphotic spine in which the anchor screws at T9, T10 are offset horizontally from the center of the side of the vertebrae.

FIG. 28 illustrates the same side elevation of a kyphotic spine of FIG. 20, but with a subset of the anchor screws 322 offset horizontally from the approximate vertical center line 382 of the side of the vertebrae. In particular, the anchor screws 322 on T9 and T10 are offset posteriorly from the approximate vertical center line 382. As a result of this horizontally offset placement of the anchor screws 322 on T9 and T10, the tensioning cord 338 will be offset horizontally and located more towards the posterior in the middle of the spine at T9, T10 during de-rotation. The surgeon is able to select which, if any, of the anchor screws 322 are located posterior or anterior of the center line 382, and the distance from the center line. By varying the posterior/anterior location of the anchor screws, the surgeon can manipulate the tensioning cord to achieve optimal tensioning angles and degree, based on the needs of the patient.

Figure 29A:
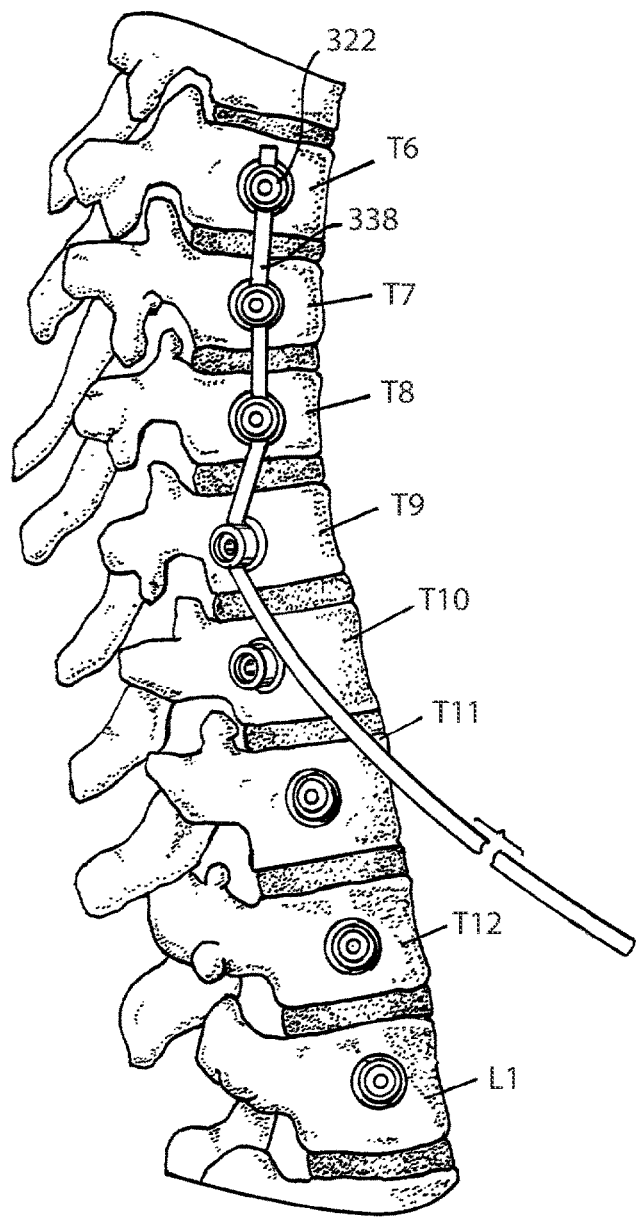
FIG. 29A illustrates the tensioning cord inserted through the horizontally offset anchor screw at T9, prior to de-rotation of T9.
Figure 29B:
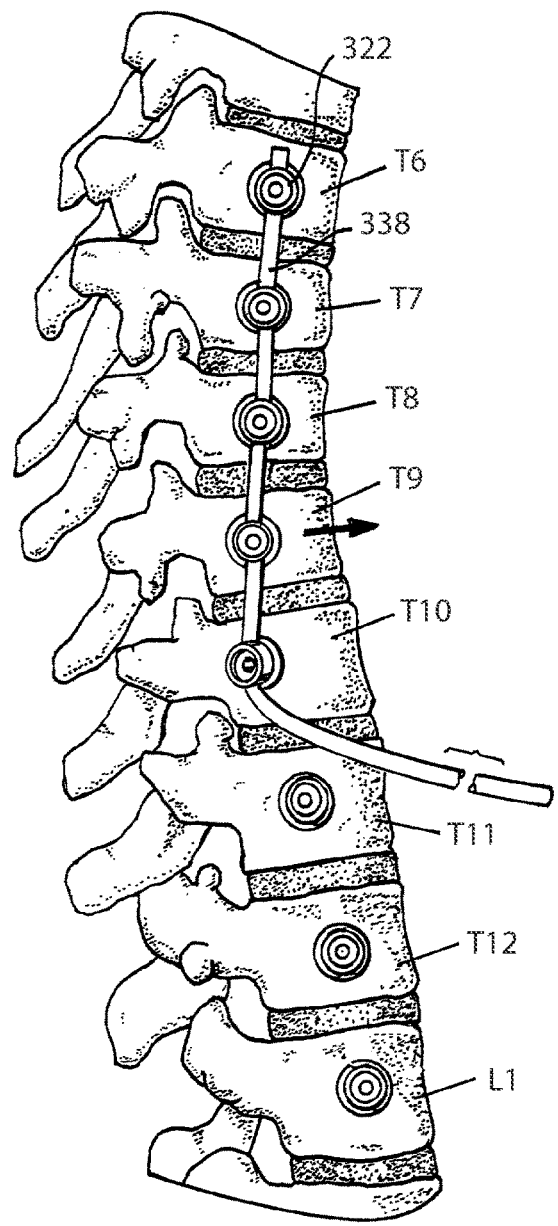
FIG. 29B illustrates the tensioning cord inserted through the horizontally offset anchor screw at T10, after de-rotation of T9 but prior to de-rotation of T10.

FIGS. 29a-29d illustrate the vertebrae at various stages of the corrective de-rotation of the spine in this embodiment. The vertebrae T7 and T8 are in initially de-rotated as previously described, and then the tensioning cord 338 is inserted into the horizontally offset anchor screw 322 on T9 as shown in FIG. 29a. Vertebra T9 is then de-rotated, and the tensioning cord 338 is then inserted through the horizontally offset anchor screw at T10, prior to de-rotation of T10, as shown in FIG. 29b.

Figure 29C:
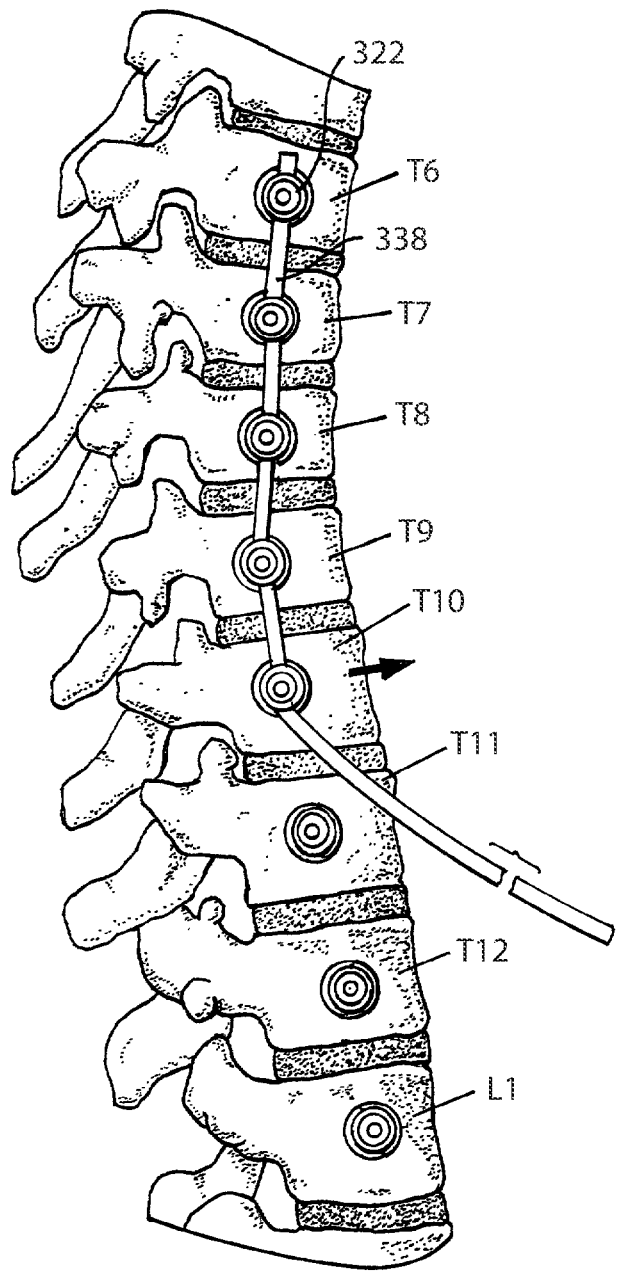
FIG. 29C illustrates the tensioning cord inserted through the anchor screws at T9 and T10 after de-rotation of T9 and T10.
Figure 29D:
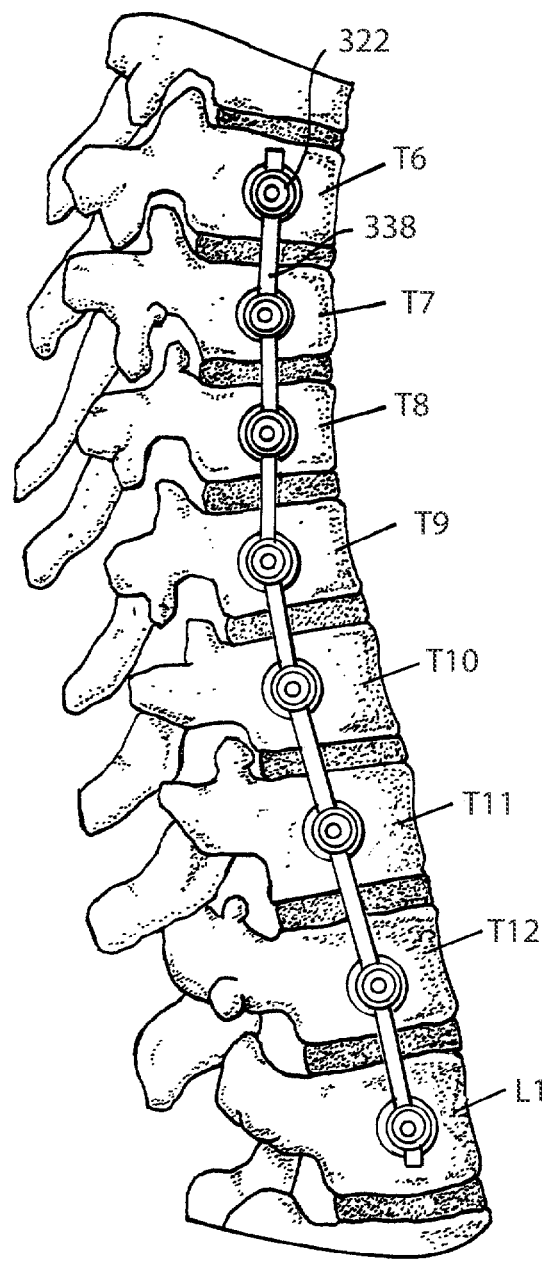
FIG. 29D illustrates the tensioning cord inserted through all of the anchor screws and after de-rotation of all the vertebrae T6 through L1.

Vertebra T10 is then de-rotated, and FIG. 29c illustrates the tensioning cord inserted through the anchor screws at T9 and T10 after de-rotation of T9 and T10. FIG. 29d illustrates the tensioning cord inserted through all of the anchor screws and after de-rotation of all the vertebrae T6 through L1. It is noted that the anchor screws at T9 and T10 may still be slightly off-center, even after their de-rotation.

This alternative posterior offset placement of the anchor screws 322 provides the surgeon with biomechanical advantages and increased leverage as he or she performs the de-rotation maneuvers discussed above. In a further alternative embodiment (not shown), the anchor screws 322 may be inserted into each vertebrae gradually more posteriorly from the approximate vertical center line 382 along the horizontal axis from T6 through T9, then gradually more anteriorly along the horizontal axis from T10 through L1.

In another alternative embodiment shown in FIGS. 30 and 31, a subset of the anchor screws 322 are offset vertically (superior and inferior) from the approximate horizontal center line 384 of the side of the vertebrae. That is, the anchor screws 322 are inserted gradually more towards the upper end of each vertebrae (and offset from the approximate horizontal center line 384) going from T10 upwards towards T6, and likewise gradually more towards the lower end of each vertebrae (and offset from the approximate horizontal center line 384) going from T11 downwards towards L1. FIG. 31 illustrates the tensioning cord 338 when located through the anchor screws 322 of FIG. 30, and after corrective de-rotation of all vertebrae. This alternative vertical offset placement of the anchor screws also provides the surgeon with biomechanical advantages of bone screw strength in the vertebral body and increased leverage as he or she performs the de-rotation maneuvers discussed above. This alternate placement of the anchor screws also provides better bone fixation and resistance to plowing of the screw in the vertebral body during tensioning. Note that this vertical offset methodology may be combined with the horizontal offset shown in FIG. 28 if desired.

This anchor screw offset approach may also be used with double screw embodiments described herein. Reference is made to FIG. 43, which illustrates the anchor screws inserted posterior and/or anterior to the center lines 382, and FIG. 44, which illustrates the anchor screws inserted superior and/or inferior to the center lines 384. Both embodiments may be combined if desired such that an anchor screw may be offset vertically and horizontally.

Thus, the anchor screws may be horizontally and/or vertically offset from center, in both a single row and double row embodiment. In the single row embodiment, provided is an improved method of performing spinal correction surgery on a patient in which a plurality of vertebrae are adjusted with respect to each other, comprising the steps of creating a vertical mini-opening in a side of the patient to enable the surgeon to access directly the plurality of the vertebrae without use of a portal; inserting, via the mini-opening, an anchor screw into each of the plurality of vertebrae being operated on, each anchor screw comprising a channel suitable for accepting a flexible tensioning cord; disposing, via the mini-opening, a flexible tensioning cord within the channels of the anchor screws to enable an adjustment procedure on the plurality of vertebrae; and performing a vertebrae adjustment procedure which each of the plurality of vertebrae is adjusted with respect to at least one other vertebra and the flexible tensioning cord is secured within the channel of the corresponding anchor screw of the adjusted vertebra in order to maintain the adjustment of the vertebrae wherein (1) each of the plurality of anchor screws is inserted into substantially the center of the side of each of the vertebrae, or (2) at least some of the plurality of anchor screws are offset horizontally from the center of the side of the vertebrae whereby the tensioning cord is offset horizontally and located more towards the posterior in the middle of the spine, or (3) at least some of the plurality of anchor screws are offset horizontally from the center of the side of the vertebrae whereby the tensioning cord is offset horizontally and located more towards the anterior in the middle of the spine, or (4) at least some of the plurality of anchor screws are offset vertically from the center of the side of the vertebrae.

In the double row embodiment, provided is an improved method of performing spinal correction surgery on a patient in which a plurality of vertebrae are adjusted with respect to each other using a double screw/double cord methodology, comprising the steps of creating a vertical mini-opening in a side of the patient to enable the surgeon to access directly the plurality of the vertebrae without use of a portal; inserting a pair of anchor screws via the mini-opening into each of the plurality of vertebrae being operated on, each of the anchor screws comprising a channel suitable for accepting a flexible tensioning cord, such that a posterior row of posterior anchor screws are formed along the vertebrae next to an anterior row of anterior anchor screws formed along the vertebrae; disposing a flexible posterior tensioning cord within the channels of the posterior row of posterior anchor screws to enable a posterior adjustment procedure on each of the plurality of vertebrae; performing a posterior vertebrae adjustment procedure in which each of the plurality of vertebrae is adjusted with respect to at least one other vertebra and the flexible posterior tensioning cord is secured within the channels of the posterior anchor screws at a first tension in order to maintain adjustment of the vertebrae; disposing a flexible anterior tensioning cord within the channels of the anterior row of anterior anchor screws to enable an anterior adjustment procedure on the plurality of vertebrae; and performing an anterior vertebrae adjustment procedure in which each of the plurality of vertebrae is adjusted with respect to at least one other vertebra and the flexible anterior tensioning cord is secured within the channels of the anterior anchor screws at a second tension that is different from the first tension in order to maintain adjustment of the vertebrae; wherein (1) at least some of the plurality of anchor screws in the posterior row are offset horizontally from other anchor screws in the posterior row; or (2) at least some of the plurality of anchor screws in the anterior row are offset horizontally from other anchor screws in the anterior row; or (3) at least some of the plurality of anchor screws in the posterior row are offset vertically from other anchor screws in the posterior row; or (4) at least some of the plurality of anchor screws in the anterior row are offset vertically from other anchor screws in the anterior row.

Depending on its placement, the anchor screw may extend through a relatively thinner vertebra such that the screw tip protrudes out of the opposite side, for example by up to 2 mm. This may affect the location chosen by the surgeon for the screw (i.e., centered, offset horizontally, and/or offset vertically). See, e.g., FIGS. 39, 39A, 40 and 40A.

Crossover Tensioning Cords

Figure 32:
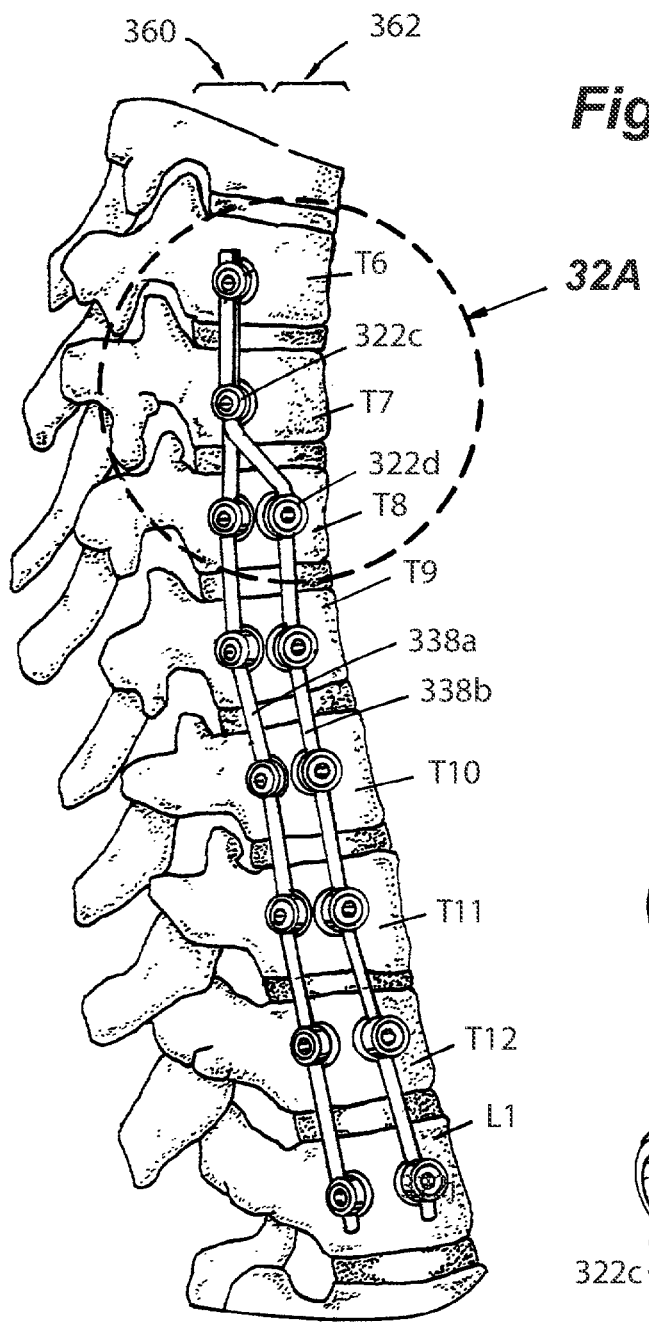
FIG. 32 illustrates an alternative embodiment in which one of the tensioning cords in the double screw/double cord application crosses over from one row of anchor screws into the second row of anchor screws.
Figure 32A:
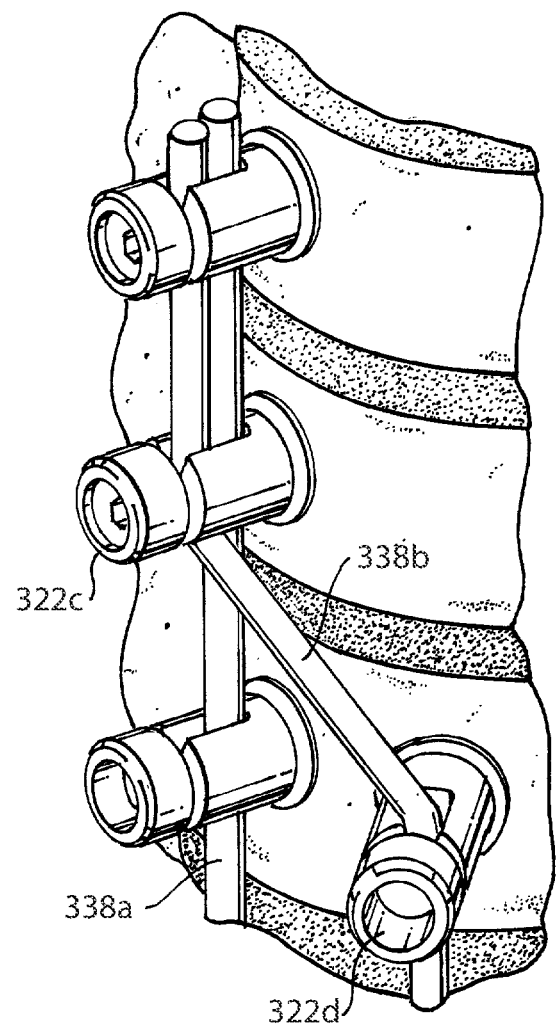
FIG. 32A is an enlarged perspective view, taken at arrow 32a of FIG. 32, showing the anchor screws and tensioning cord that crosses over from one row of anchor screws into the second row of anchor screws.

Shown in FIG. 32 is an alternative embodiment in which one of the tensioning cords in the double screw/double cord application crosses over from one row of anchor screws into the other row of anchor screws. As shown in this thoracic portion of the spine, a single posterior anchor screw 322c is inserted into T6 and T7 as shown, and both the posterior tensioning cord 338a and the anterior tensioning cord 338b are disposed within the channels of those posterior anchor screws during de-rotation of T7 with respect to T6. Then, the posterior tensioning cord 338a is disposed within the posterior anchor screw 322c on T8, while the anterior tensioning cord 338b crosses over and is disposed within the anterior anchor screw 322d on T8. This is shown in closeup detail in FIG. 32a. Vertebra T8 is then de-rotated with respect to T6 and T7 using the posterior anchor screws 322c, and the posterior tensioning cord 338a continues along the posterior anchor screws 322c. De-rotation proceeds along the remaining vertebrae using the posterior anchor screws 322c and the posterior tensioning cord 338a. Similarly, the anterior tensioning cord 338b is located through the anterior anchor screw 322d on T8, which is de-rotated with respect to T7. De-rotation proceeds along the rest of the vertebrae, now using the anterior anchor screws 322d and the anterior tensioning cord 338b. The corrected spine is shown in FIG. 32. This procedure is particularly useful in situations in which two tensioning cords are desired for the de-rotation maneuvers, but certain vertebrae have only enough mass to hold a single screw.

Figure 33:
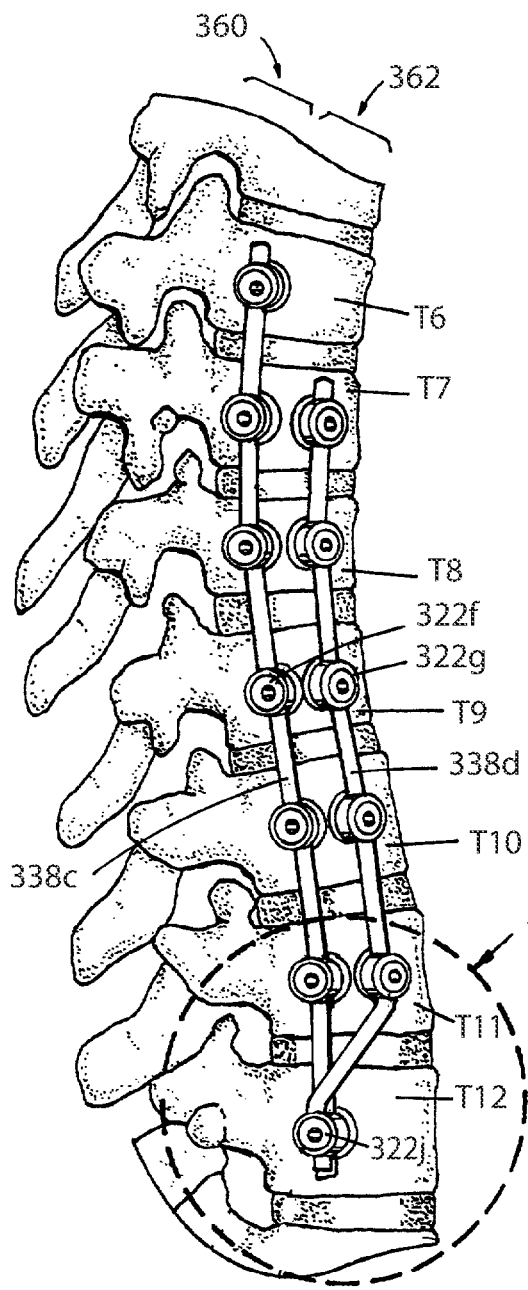
FIG. 33 illustrates an alternative embodiment in which one of the tensioning cords in the double screw/double cord application for a double curve crosses over from one row of anchor screws into the second row of anchor screws and wherein the use of the upper bridge tensioning cord is eliminated.
Figure 33A:
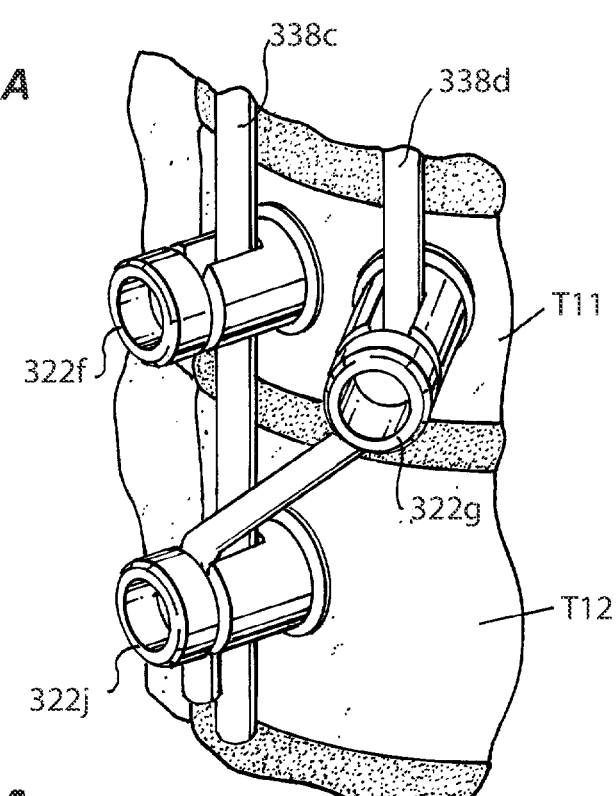
FIG. 33A is an enlarged perspective view, taken at arrow 33a of FIG. 33, showing the anchor screws and tensioning cord that crosses over from one row of anchor screws into the second row of anchor screws.

In the more complex case of a double scoliosis curve, a similar cross-over technique may also be implemented. FIG. 33 shows the same thoracic side elevation as in FIG. 26, but where the use of the upper bridge posterior tensioning cord 338e is eliminated, and the upper anterior tensioning cord 338d extends through the upper anterior screw 322g and over to and through the upper neutral posterior anchor screw 322j. FIG. 33a shows this modification in closeup detail. Likewise (although not shown), at the lumbar portion, the lower bridge tensioning cord may be eliminated and the lower anterior tensioning cord 338g may extend through the lower anterior screw 322i and over to and through the lower neutral posterior anchor screw 322k.

Crisscrossed Tensioning Cords

Several alternative embodiments are provided that utilize one or more crisscrossed tensioning cords in a double screw/double cord application. In general, in these embodiments, a tensioning cord crosses over from one row of anchor screws to the other row of anchor screws and back, one or more times, in a crisscross or weaved type of pattern. Either or both of the tensioning cords may crisscross in this manner, thus providing further advantages in de-rotation of the spine by providing greater strength and control of the corrected vertebrae, for example. These crisscrossed tensioning cords may be implemented alone or in conjunction with single or double straight tensioning cords, as now described with more particularity.

FIG. 34a illustrates an alternative embodiment in which the thoracic portion of the spine has a double screw/double cord embodiment with a pair of linear tensioning cords and a (single) posterior crossover tensioning cord. Shown in FIG. 34a is the spine in the final, corrected position, with all tensioning cords secured in place. In particular, a posterior crossover tensioning cord 338i is added to the thoracic portion of the spine having a double screw/double cord embodiment with a pair of straight tensioning cords 338a, 338b, similar to what is shown in FIG. 22. That is, in addition to the posterior tensioning cord 338a and anterior tensioning cord 338b, the posterior crossover tensioning cord 338i is added at the posterior anchor screw 322c on T8, which then crosses over to the anterior anchor screw 322d on T9, then over to the posterior anchor screw 322c on T10, then over to the anterior anchor screw 322d on T11, where the posterior crossover tensioning cord 338i terminates, thus forming a crisscross pattern. Thus, FIG. 34a illustrates the thoracic portion of the spine after all relevant vertebrae have been corrected through de-rotation in accordance with this invention.

This modification may provide increased de-rotational correction stability in certain cases, meaning the prevention of loss of rotational correction that may sometimes occur after the de-rotation. It is noted that this is an example of this tensioning crisscross embodiment; the specific crisscross pattern may vary in accordance with the particular effect the surgeon is attempting to accomplish. For example, the crossover pattern may start on a different vertebra than T8, and/or begin on the anterior row of anchor screws 322d rather than the posterior row of screws 322c, or it may implement less crossovers, or more crossovers, if desired.

FIG. 34b illustrates the same thoracic spine as in FIG. 34a, but with a fourth tensioning cord added to provide a shoelace type pattern. Shown in FIG. 34b is the spine in the final, corrected position, with all tensioning cords secured in place. In particular, an anterior crossover tensioning cord 338j is interwoven with the other tensioning cords 338a, 338b and 338i. As shown in this example, in addition to the posterior tensioning cord 338a, anterior tensioning cord 338b, and posterior crossover tensioning cord 338i, the anterior crossover tensioning cord 338j is added at the anterior anchor screw 322d on T8, which then crosses over to the posterior anchor screw 322c on T9, then over to the anterior anchor screw 322d on T10, then over to the posterior anchor screw 322c on T11, where the anterior crossover tensioning cord 338j terminates, thus forming a crisscross pattern with the posterior crossover tensioning cord 338i. Together, the posterior crossover tensioning cord 338i and anterior crossover tensioning cord 338j crisscross (similar to a pair of shoelaces), and interoperate with the posterior tensioning cord 338a and anterior tensioning cord 338b, to provide increased de-rotational correction stability in certain cases, and also helps to prevent the loosening of the cords that may sometimes occur after the de-rotation correction. Again, this is an example of this tensioning crisscross embodiment; the specific crisscross pattern may vary in accordance with the particular effect the surgeon is attempting to accomplish. For example, the crossover pattern may start on a different vertebra, or it may implement less crossovers, or more crossovers, if desired.

Figure 35:
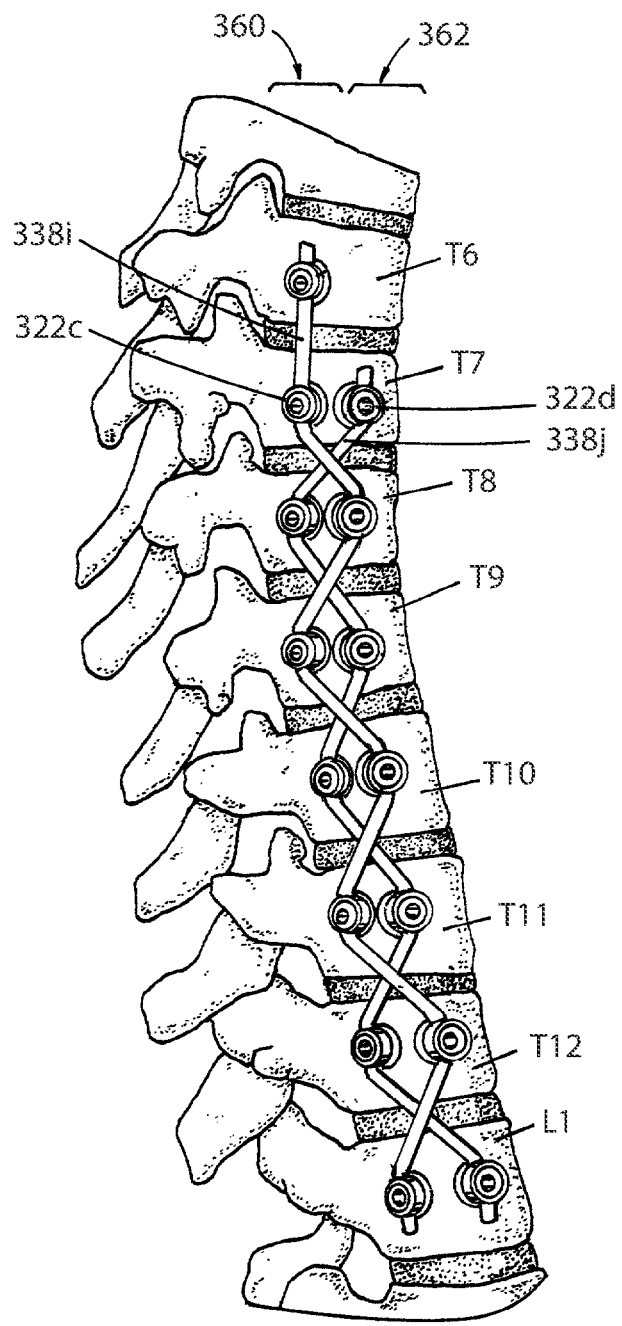
FIG. 35 illustrates an alternative embodiment in which the thoracic portion of the spine has a double screw/double cord embodiment with only a posterior crossover tensioning cord and an anterior crossover tensioning cord.

FIG. 35 illustrates an alternative embodiment in which the thoracic portion of the spine has a double screw/double cord embodiment with a pair of crisscrossed tensioning cords 338i, 338j but no straight tensioning cords as in FIG. 34b. As shown in this example, a posterior crossover tensioning cord 338i and anterior crossover tensioning cord 338j are located through the various anchor screws similarly to what was described above with respect to FIG. 34b. That is, the posterior crossover tensioning cord 338i is located through the posterior anchor screws 322c at T6 and T7, then crosses over to the anterior anchor screw 322d on T8, then over to the posterior anchor screw 322c on T9, then over to the anterior anchor screw 322d on T10, then over to the posterior anchor screw 322c on T11, then over to the anterior anchor screw 322d on T12, then over to the posterior anchor screw 322c on L1 where the posterior crossover tensioning cord 338i terminates.

Similarly, the anterior crossover tensioning cord 338j is located on the anterior anchor screw 322d on T7, which then crosses over to the posterior anchor screw 322c on T8, then over to the anterior anchor screw 322d on T9, then over to the posterior anchor screw 322c on T10, then over to the anterior anchor screw 322d on T11, then over to the posterior anchor screw 322c on T12, then over to the anterior anchor screw 322d on L1, where the anterior crossover tensioning cord 338j terminates, thus forming a crisscross pattern with the posterior crossover tensioning cord 338i. Together, the posterior crossover tensioning cord 338i and anterior crossover tensioning cord 338j crisscross (similar to a pair of shoelaces) to provide increased de-rotational correction stability in certain cases, and also helps to prevent the loosening of the cords that may sometimes occur after the de-rotation correction. Again, this is an example of this tensioning crisscross embodiment; the specific crisscross pattern may vary in accordance with the particular effect the surgeon is attempting to accomplish. For example, the crossover pattern may start on a different vertebra, or it may implement less crossovers, or more crossovers, if desired.

Figure 36:
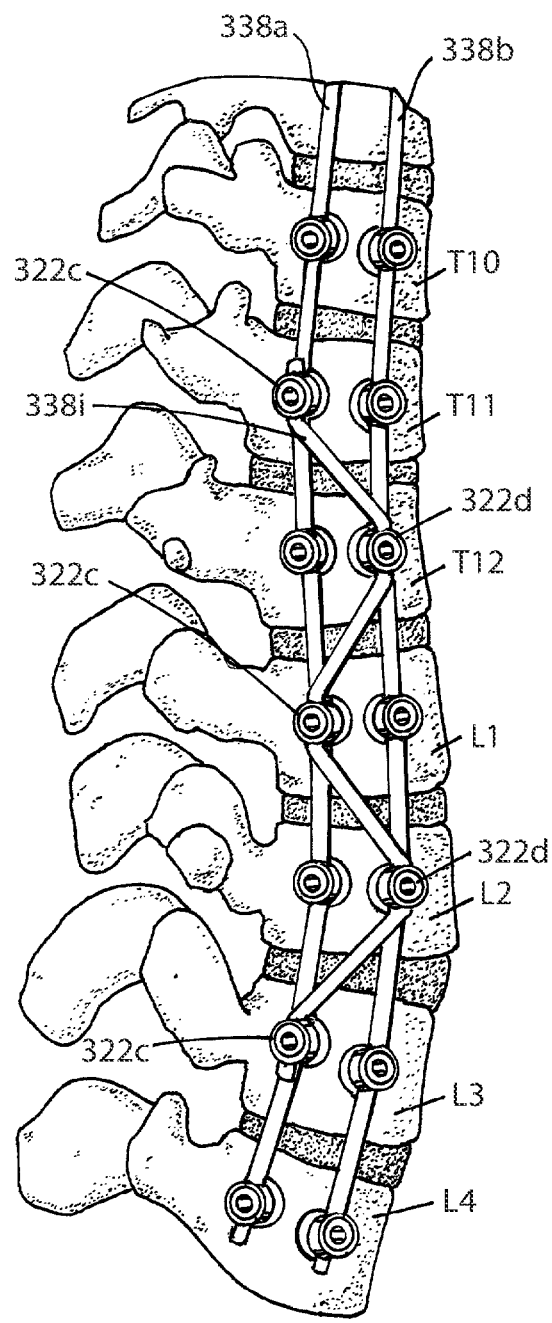
FIG. 36 illustrates an alternative embodiment in which the lumbar portion of the spine has a double screw/double cord embodiment with a pair of straight tensioning cords and a posterior crossover tensioning cord.

FIG. 36 illustrates an alternative embodiment in which the lumbar portion of the spine has a double screw/double cord embodiment with a pair of linear tensioning cords and a posterior crossover tensioning cord, similar to what is shown for the thoracic spine in FIG. 34a. As shown in FIG. 36, in addition to the posterior tensioning cord 338a and anterior tensioning cord 338b, the posterior crossover tensioning cord 338i is added at the posterior anchor screw 322c on T11, which then crosses over to the anterior anchor screw 322d on T12, then over to the posterior anchor screw 322c on L1, then over to the anterior anchor screw 322d on L2, then over to the posterior anchor screw 322c on L3, where the posterior crossover tensioning cord 338i terminates, thus forming a crisscross pattern. Of course, the tensioning cords 338a, 338b, and 338i are inserted through the anchor screws 322c, 322d on each particular vertebra as that vertebra is corrected with respect to the prior vertebrae, as explained previously. Thus, FIG. 36 illustrates the lumbar portion of the spine after all relevant vertebrae have been corrected through de-rotation in accordance with this invention.

This modification may provide increased de-rotational correction stability in certain cases, and also helps to prevent the loosening of the cords that may sometimes occur after the de-rotation correction. It is noted that this is an example of this tensioning crisscross embodiment; the specific crisscross pattern may vary in accordance with the particular effect the surgeon is attempting to accomplish. For example, the crossover pattern may start on a different vertebra than T11, and/or begin on the anterior row of anchor screws 322d rather than the posterior row of screws 322c, or it may implement less crossovers, or more crossovers, if desired.

Figure 37:
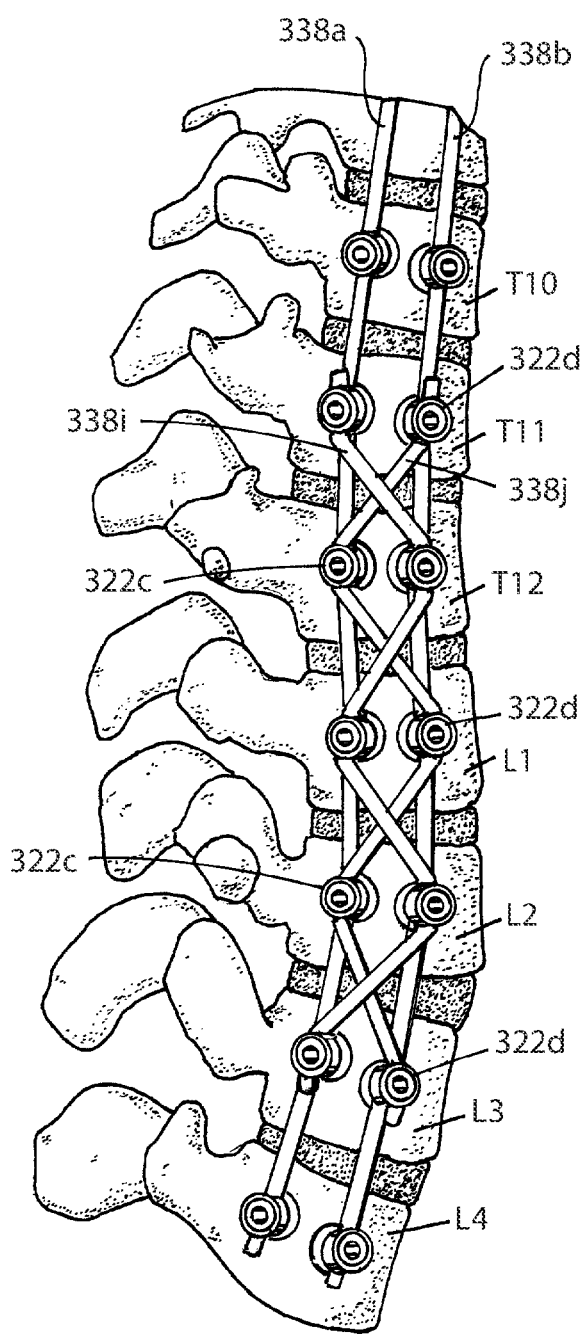
FIG. 37 illustrates the alternative embodiment of FIG. 36 in which the lumbar portion of the spine has a double screw/double cord embodiment with a pair of straight tensioning cords, a posterior crossover tensioning cord, and an anterior crossover tensioning cord.

FIG. 37 illustrates the same lumbar spine as in FIG. 36, but with a fourth tensioning cord added to provide a shoelace type pattern. Thus, an anterior crossover tensioning cord 338j is interwoven with the other tensioning cords 338a, 338b and 338i. As shown in this example, in addition to the posterior tensioning cord 338a, anterior tensioning cord 338*b*, and posterior crossover tensioning cord 338*i*, the anterior crossover tensioning cord 338*j* is added at the anterior anchor screw 322*d* on T11, which then crosses over to the posterior anchor screw 322*c* on T12, then over to the anterior anchor screw 322*d* on L1, then over to the posterior anchor screw 322*c* on L2, then over to the anterior anchor screw 322*d* on L3 where the anterior crossover tensioning cord 338*j* terminates, thus forming a crisscross pattern with the posterior crossover tensioning cord 338*i*. Together, the posterior crossover tensioning cord 338*i* and anterior crossover tensioning cord 338*j* crisscross (similar to a pair of shoelaces), and interoperate with the posterior tensioning cord 338*a* and anterior tensioning cord 338*b*, to provide increased de-rotational correction stability in certain cases, and also helps to prevent the loosening of the cords that may sometimes occur after the de-rotation correction. Again, this is an example of this tensioning crisscross embodiment; the specific crisscross pattern may vary in accordance with the particular effect the surgeon is attempting to accomplish. For example, the crossover pattern may start on a different vertebra, or it may implement less crossovers, or more crossovers, if desired.

Auxiliary Tensioning Cords

Figure 41:
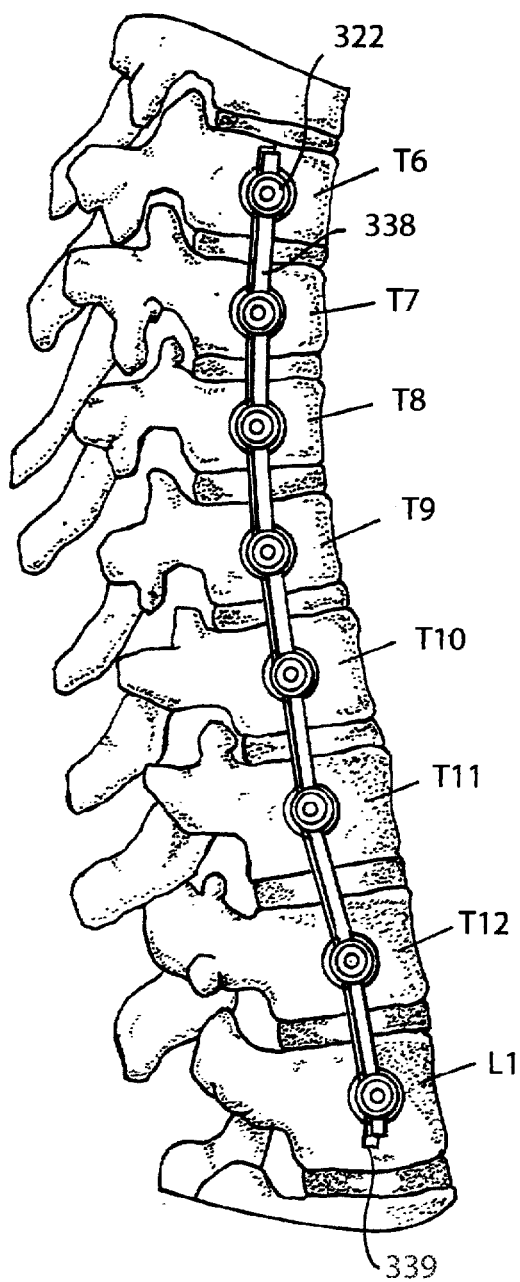
FIG. 41 illustrates an alternative embodiment in which an auxiliary tensioning cord is added such that two tensioning cords are used in the alignment procedures.

In further alternative embodiments, an auxiliary tensioning cord(s) is/are added to provide redundancy and further control over tensioning of the anchor screws. For example, in FIG. 41, an auxiliary tensioning cord 339 has been added alongside tensioning cord 338. Use of this second, auxiliary tensioning cord 339 provides redundancy in the event that the tensioning cord 338 breaks or is otherwise compromised as a result, e.g., of rubbing against an anchor screw. The tensioning procedure occurs in the same fashion as in the single cord examples described above, except that after the tensioning cord 338 is tensioned with the tensioner, the anchor screws are not yet tightened, and the auxiliary tensioning cord 339 is tensioned by hand by the surgeon. Then, the anchor screws are tightened, thus securing both cords within the screws.

Figure 42:
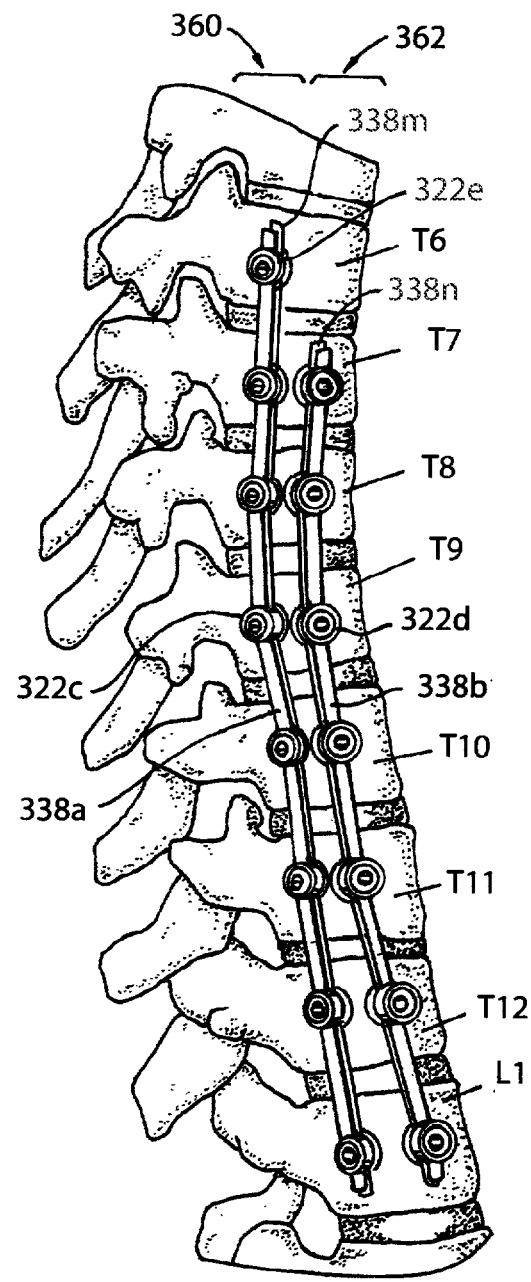
FIG. 42 illustrates an alternative embodiment in which a pair of auxiliary tensioning cords are added to the double screw/double cord embodiment(s) such that four tensioning cords are used in the alignment procedures.

The use of auxiliary tensioning cords may be extended to all embodiments discussed herein, including the double screw/double cord embodiments described above. For example, FIG. 42 illustrates the use of an auxiliary posterior tensioning cord 338*m* and an auxiliary anterior tensioning cord 338*n*, which are tensioned in the same manner as described above. Similarly, the crossover tensioning cord embodiments shown in FIGS. 32 and 33 and the crisscrossed tensioning cord embodiments shown in FIGS. 34A, 34B, 35, 36 and 37 can in the alternative implement the additional auxiliary tensioning cords as well.

Thus, two tensioning cords may be used instead of a single tensioning cord, which provides redundancy in the event one of the cords breaks over time. In this respect, provided is an embodiment using a single row of anchor screws and dual cords, in particular an improved method of performing spinal correction surgery on a patient in which a plurality of vertebrae are adjusted with respect to each other, comprising the steps of: creating a vertical mini-opening in a side of the patient to enable the surgeon to access directly the plurality of the vertebrae without use of a portal; inserting, via the mini-opening, an anchor screw into each of the plurality of vertebrae being operated on, each anchor screw comprising a channel suitable for accepting a pair of flexible tensioning cords; disposing, via the mini-opening, a pair of flexible tensioning cords, comprising a first flexible tensioning cord and a second flexible tensioning cord, within the channels of the anchor screws to enable an adjustment procedure on the plurality of vertebrae; and performing a vertebrae adjustment procedure by tensioning with a tensioner the first flexible tensioning cord in the channel of a first anchor screw; tensioning by hand the second flexible tensioning cord in the channel of the first anchor screw; and securing the first flexible tensioning cord and the second flexible tensioning cord in the channel of a second anchor screw in order to maintain the adjustment of the vertebrae.

Similarly, dual cords may be used in each row of a double row embodiment (four cords total). Here, provided is an improved method of performing spinal correction surgery on a patient in which a plurality of vertebrae are adjusted with respect to each other, comprising the steps of: creating a vertical mini-opening in a side of the patient to enable the surgeon to access directly the plurality of the vertebrae without use of a portal; inserting, via the mini-opening, a pair of anchor screws into each of the plurality of vertebrae being operated on, each of the anchor screws comprising a channel suitable for accepting a pair of flexible tensioning cords, such that a substantially aligned posterior row of posterior anchor screws are formed along the vertebrae next to a substantially aligned anterior row of anterior anchor screws formed along the vertebrae; disposing a first pair of flexible tensioning cords, comprising a first flexible tensioning cord and a second flexible tensioning cord, within the channels of the posterior row of posterior anchor screws to enable a posterior vertebrae adjustment procedure on the plurality of vertebrae; performing a posterior vertebrae adjustment procedure by tensioning with a tensioner the first flexible tensioning cord in the channel of a first posterior anchor screw; tensioning by hand the second flexible tensioning cord in the channel of the first posterior anchor screw; and securing the first flexible tensioning cord and the second flexible tensioning cord in the channel of a second posterior anchor screw in order to maintain the adjustment of the vertebrae; disposing a second pair of flexible tensioning cords, comprising a third flexible tensioning cord and a fourth flexible tensioning cord, within the channels of the anterior row of anterior anchor screws to enable an anterior vertebrae adjustment procedure on the plurality of vertebrae; performing an anterior vertebrae adjustment procedure by tensioning with the tensioner the third flexible tensioning cord in the channel of a first anterior anchor screw; tensioning by hand the fourth flexible tensioning cord in the channel of the first anterior anchor screw; and securing the third flexible tensioning cord and the fourth flexible tensioning cord in the channel of a second anterior anchor screw in order to maintain the adjustment of the vertebrae.

Interplay of Disc Release, De-Rotation, and Double Screw/Double Cord Methodologies As taught herein, various major aspects of the invention are the releasing of discs, the use of de-rotation maneuvers, and the use of double screws/double cords. Each of these three major aspects of the invention may be used independently of the others, or if applicable a surgeon may use two of these techniques or all three of these techniques as desired. For example, the de-rotation methodologies described herein may be implemented with a single screw/single cord application, but if the patient's scoliosis is so severe that double screws/double cords are required, then the de-rotation may be implemented with double screws/double cords. In that case, the surgeon would preferably implement the de-rotation correction techniques with the first set of screws/cord (e.g. the posterior set), and then repeat the same maneuvers with the second set (the anterior set). Similarly, the disc release procedure may not be applicable or even advisable in certain situations, in which case would not be performed by the surgeon.

Since each of the three major methodologies described herein address different problems encountered by the surgeon as described, it is up to the surgeon using professional judgment and experience which of these methodologies, and in which combination, would be best suited for a given procedure.

What is claimed is:

1. An improved method of performing spinal correction surgery on a patient in which a plurality of vertebrae are adjusted with respect to each other using a double screw/double cord methodology, wherein a plurality of anchor screws are inserted into corresponding vertebrae to enable the spinal correction, wherein each of the anchor screws comprises a channel suitable for accepting a tensioning cord;
   the vertebrae forming a double scoliosis curve comprising
      an upper curve defined by an upper set of vertebrae disposed substantially in a first direction,
      a lower curve defined by a lower set of vertebrae disposed substantially in a second direction substantially opposite to the first direction, and
      a neutral vertebra located between the upper set of vertebrae and the lower set of vertebrae;
   the method comprising the steps of:
      creating a vertical mini-opening in a side of the patient to enable a surgeon to access directly the plurality of the vertebrae;
      for the upper set of vertebrae:
         inserting a pair of anchor screws into each vertebra in the upper set of vertebrae and the neutral vertebra along the convexity of the upper curve, such that a substantially aligned upper posterior row of upper posterior anchor screws are formed along the upper vertebrae and the neutral vertebra next to a substantially aligned upper anterior row of upper anterior anchor screws formed along the upper vertebrae and the neutral vertebra;
      for the lower set of vertebrae:
         inserting a pair of anchor screws into each vertebra in the lower set of vertebrae and the neutral vertebra along the convexity of the lower curve which is substantially opposite the convexity of the upper curve, such that a substantially aligned lower posterior row of lower posterior anchor screws are formed along the lower vertebrae and the neutral vertebra next to a substantially aligned lower anterior row of lower anterior anchor screws formed along the lower vertebrae and the neutral vertebra;
      disposing an upper posterior tensioning cord within the channels of the upper posterior row of upper posterior anchor screws to enable an upper posterior adjustment procedure on the upper set of vertebrae and the neutral vertebra;
      performing an upper posterior vertebrae adjustment procedure in which each of the set of upper vertebrae and the neutral vertebra is adjusted with respect to at least one other upper vertebra and the upper posterior tensioning cord is secured within the channels of the upper posterior anchor screws in order to maintain the upper posterior adjustment of the vertebrae;
      disposing an upper anterior tensioning cord within the channels of the upper anterior row of upper anterior anchor screws to enable an upper anterior adjustment procedure on the upper set of vertebrae and the neutral vertebra;
      performing an upper anterior vertebrae adjustment procedure in which each of the set of upper vertebrae and the neutral vertebra is adjusted with respect to at least one other upper vertebra and the upper anterior tensioning cord is secured within the channels of the upper anterior anchor screws in order to maintain the upper anterior adjustment of the vertebrae;
      disposing a lower posterior tensioning cord within the channels of the lower posterior row of lower posterior anchor screws to enable a lower posterior adjustment procedure on the lower set of vertebrae and the neutral vertebra;
      performing a lower posterior vertebrae adjustment procedure in which each of the set of lower vertebrae and the neutral vertebra is adjusted with respect to at least one other lower vertebra and the lower posterior tensioning cord is secured within the channels of the lower posterior anchor screws in order to maintain the lower posterior adjustment of the vertebrae;
      disposing a lower anterior tensioning cord within the channels of the lower anterior row of lower anterior anchor screws to enable a lower anterior adjustment procedure on the lower set of vertebrae and the neutral vertebra; and
      performing a lower anterior vertebrae adjustment procedure in which each of the set of lower vertebrae and the neutral vertebra is adjusted with respect to at least one other lower vertebra and the lower anterior tensioning cord is secured within the channels of the lower anterior anchor screws in order to maintain the lower anterior adjustment of the vertebrae.

2. The method of claim 1 wherein the upper posterior vertebrae adjustment procedure is a de-rotation procedure comprising the steps of
   locating a stationary tower on a first upper posterior anchor screw of a first upper vertebra,
   locating a de-rotation tower on a second upper posterior anchor screw of a second upper vertebra,
   performing a de-rotation maneuver by
      applying a downwards translational force vector to the de-rotation tower,
      applying a lateral force vector to the de-rotation tower, and
      simultaneously applying a lateral counterforce vector to the stationary tower in opposition to the lateral force vector being applied to the de-rotation tower,
   tensioning the upper posterior tensioning cord in the channel of the second upper posterior anchor screw,
   securing the upper posterior tensioning cord in the channel of the second upper posterior anchor screw in order to maintain the de-rotation of the upper vertebrae,
   re-locating the de-rotation tower to the upper posterior anchor screw of a subsequent upper vertebra, and
   repeating the de-rotation maneuver until all of the upper vertebrae and the neutral vertebra have been de-rotated as desired.

3. The method of claim 1 wherein the upper anterior vertebrae adjustment procedure is a de-rotation procedure comprising the steps of
   locating a stationary tower on a first upper anterior anchor screw of a first upper vertebra,
   locating a de-rotation tower on a second upper anterior anchor screw of a second upper vertebra,
   performing a de-rotation maneuver by
      applying a downwards translational force vector to the de-rotation tower,
      applying a lateral force vector to the de-rotation tower, and simultaneously applying a lateral counterforce vector to the stationary tower in opposition to the lateral force vector being applied to the de-rotation tower, tensioning the upper anterior tensioning cord in channel of the second upper anterior anchor screw, securing the upper anterior tensioning cord in the channel of the second upper anterior anchor screw in order to maintain the de-rotation of the upper vertebrae, re-locating the de-rotation tower to the upper anterior anchor screw of a subsequent upper vertebra, and repeating the de-rotation maneuver until all of the upper vertebrae and the neutral vertebra have been de-rotated as desired.

4. The method of claim 1 wherein the lower posterior vertebrae adjustment procedure is a de-rotation procedure comprising the steps of locating a stationary tower on a first lower posterior anchor screw of a first lower vertebra, locating a de-rotation tower on a second lower posterior anchor screw of a second lower vertebra, performing a de-rotation maneuver by
  applying a downwards translational force vector to the de-rotation tower,
  applying a lateral force vector to the de-rotation tower, and
  simultaneously applying a lateral counterforce vector to the stationary tower in opposition to the lateral force vector being applied to the de-rotation tower, tensioning the lower posterior tensioning cord in channel of the second lower posterior anchor screw, securing the lower posterior tensioning cord in the channel of the second lower posterior anchor screw in order to maintain the de-rotation of the lower vertebrae, re-locating the de-rotation tower to the lower posterior anchor screw of a subsequent lower vertebra, and repeating the de-rotation maneuver until all of the lower vertebrae and the neutral vertebra have been de-rotated as desired.

5. The method of claim 1 wherein the lower anterior vertebrae adjustment procedure is a de-rotation procedure comprising the steps of locating a stationary tower on a first lower anterior anchor screw of a first lower vertebra, locating a de-rotation tower on a second lower anterior anchor screw of a second lower vertebra, performing a de-rotation maneuver by
  applying a downwards translational force vector to the de-rotation tower,
  applying a lateral force vector to the de-rotation tower, and
  simultaneously applying a lateral counterforce vector to the stationary tower in opposition to the lateral force vector being applied to the de-rotation tower, tensioning the lower anterior tensioning cord in channel of the second lower anterior anchor screw, securing the lower anterior tensioning cord in the channel of the second lower anterior anchor screw in order to maintain the de-rotation of the lower vertebrae, re-locating the de-rotation tower to the lower anterior anchor screw of a subsequent lower vertebra, and repeating the de-rotation maneuver until all of the lower vertebrae and the neutral vertebra have been de-rotated as desired.

6. An improved method of performing spinal correction surgery on a patient in which a plurality of vertebrae are adjusted with respect to each other using a double screw/double cord methodology, wherein a plurality of anchor screws are inserted into corresponding vertebrae to enable the spinal correction, wherein each of the anchor screws comprises a channel suitable for accepting a tensioning cord;

the vertebrae forming a double scoliosis curve comprising
  an upper curve defined by an upper set of vertebrae disposed substantially in a first direction,
  a lower curve defined by a lower set of vertebrae disposed substantially in a second direction substantially opposite to the first direction, and
  a neutral vertebra located between the upper set of vertebrae and the lower set of vertebrae;

the method comprising the steps of:
  creating a vertical mini-opening in a side of the patient to enable a surgeon to access directly the plurality of the vertebrae;
  for the upper set of vertebrae:
    inserting a pair of anchor screws into each vertebra in the upper set of vertebrae along the convexity of the upper curve, such that a substantially aligned upper posterior row of upper posterior anchor screws are formed along the upper vertebrae next to a substantially aligned upper anterior row of upper anterior anchor screws formed along the upper vertebrae;
  for the lower set of vertebrae:
    inserting a pair of anchor screws into each vertebra in the lower set of vertebrae along the convexity of the lower curve which is substantially opposite the convexity of the upper curve, such that a substantially aligned lower posterior row of lower posterior anchor screws are formed along the lower vertebrae next to a substantially aligned lower anterior row of lower anterior anchor screws formed along the lower vertebrae; and
  for the neutral vertebra:
    inserting an upper neutral posterior anchor screw and an upper neutral anterior anchor screw into the neutral vertebra on the same side as the convexity of the upper curve, and
    inserting a lower neutral posterior anchor screw and a lower neutral anterior anchor screw into the neutral vertebra on the same side as the convexity of the lower curve;
  disposing an upper posterior tensioning cord within the channels of the upper posterior row of upper posterior anchor screws and the upper neutral posterior anchor screw, and an upper bridge posterior tensioning cord within the channels of the upper neutral posterior anchor screw and the upper posterior anchor screw adjacent the upper neutral posterior anchor screw to enable an upper posterior adjustment procedure on the upper set of vertebrae;
  performing an upper posterior vertebrae adjustment procedure in which each of the set of upper vertebrae is adjusted with respect to at least one other upper vertebra and the upper posterior tensioning cord and upper bridge posterior tensioning cord are each secured within the channels of the upper posterior anchor screws in order to maintain the upper posterior adjustment of the vertebrae;
  disposing an upper anterior tensioning cord within the channels of the upper anterior row of upper anterior anchor screws and the upper neutral anterior anchor screw, and an upper bridge anterior tensioning cord within the channels of the upper neutral anterior anchor screw and the upper anterior anchor screw adjacent the upper neutral anterior anchor screw to enable an upper anterior adjustment procedure on the upper set of vertebrae;

performing an upper anterior vertebrae adjustment procedure in which each of the set of upper vertebrae is adjusted with respect to at least one other upper vertebra and the upper anterior tensioning cord and upper bridge anterior tensioning cord are each secured within the channels of the upper anterior anchor screws in order to maintain the upper anterior adjustment of the vertebrae;

disposing a lower posterior tensioning cord within the channels of the lower posterior row of lower posterior anchor screws and the lower neutral posterior anchor screw, and a lower bridge posterior tensioning cord within the channels of the lower neutral posterior anchor screw and the lower posterior anchor screw adjacent the lower neutral posterior anchor screw, to enable a lower posterior adjustment procedure on the lower set of vertebrae;

performing a lower posterior vertebrae adjustment procedure in which each of the set of lower vertebrae is adjusted with respect to at least one other lower vertebra and the lower posterior tensioning cord and lower bridge posterior tensioning cord are each secured within the channels of the lower posterior anchor screws in order to maintain the lower posterior adjustment of the vertebrae;

disposing a lower anterior tensioning cord within the channels of the lower anterior row of lower anterior anchor screws and the lower neutral anterior anchor screw, and a lower bridge anterior tensioning cord within the channels of the lower neutral anterior anchor screw and the lower anterior anchor screw adjacent the lower neutral anterior anchor screw to enable a lower anterior adjustment procedure on the lower set of vertebrae; and performing a lower anterior vertebrae adjustment procedure in which each of the set of lower vertebrae is adjusted with respect to at least one other lower vertebra and the lower anterior tensioning cord and lower bridge anterior tensioning cord are each secured within the channels of the lower anterior anchor screws in order to maintain the lower anterior adjustment of the vertebrae.

\* \* \* \* \*